(12) United States Patent
Chudner

(10) Patent No.: US 6,749,565 B2
(45) Date of Patent: Jun. 15, 2004

(54) METHOD FOR BLOOD INFRARED SPECTROSCOPY DIAGNOSING OF INNER ORGANS PATHOLOGY

(76) Inventor: Victor Chudner, 515 E. 7$^{th}$ St., Apt. #2B, Brooklyn, NY (US) 11218

(*) Notice: Subject to any disclaimer, the term of this patent is extended or adjusted under 35 U.S.C. 154(b) by 565 days.

(21) Appl. No.: 09/866,019

(22) Filed: May 25, 2001

(65) Prior Publication Data

US 2002/0027649 A1 Mar. 7, 2002

Related U.S. Application Data

(60) Provisional application No. 60/216,922, filed on Jul. 8, 2000.

(51) Int. Cl.$^7$ .................................................. A61B 5/00
(52) U.S. Cl. ..................... 600/300; 600/309; 600/310; 600/326; 600/322; 356/39; 250/338.1; 250/340
(58) Field of Search ................................. 600/300, 309, 600/310, 473, 160, 342, 549, 326, 323, 322; 348/77; 356/39, 40, 41, 42; 250/338.1, 339.01, 339.02, 339.06, 339.07, 339.11, 339.14, 340, 341.8

(56) References Cited

U.S. PATENT DOCUMENTS

| | | | |
|---|---|---|---|
| 4,975,581 A | 12/1990 | Robinson | |
| 5,168,162 A | 12/1992 | Oong | |
| 5,261,410 A | 11/1993 | Alfano | |
| 5,473,160 A | 12/1995 | Eysel | |
| 5,596,992 A | 1/1997 | Haaland | |
| 5,733,739 A | 3/1998 | Zakim | |
| 5,800,348 A * | 9/1998 | Kaestle | 600/322 |
| 5,830,133 A | 11/1998 | Osten | |
| 5,957,841 A * | 9/1999 | Maruo et al. | 600/473 |
| 6,223,069 B1 * | 4/2001 | Pfeiffer et al. | 600/310 |
| 6,393,310 B1 * | 5/2002 | Kuenstner | 600/322 |
| 6,587,701 B1 * | 7/2003 | Stranc et al. | 600/310 |
| 6,636,759 B2 * | 10/2003 | Robinson | 600/310 |

FOREIGN PATENT DOCUMENTS

| | | |
|---|---|---|
| SU | 1698775 | 12/1991 |
| WO | WO 97/14961 | 4/1997 |
| WO | WO 97/32194 | 9/1997 |

* cited by examiner

*Primary Examiner*—Henry Bennett
*Assistant Examiner*—Fadi H. Dahbour

(57) ABSTRACT

A rapid diagnosis method for organ specific disease state is based on obtaining an infrared absorbance spectra of a patient's blood at a frequency range from about 400 cm$^{-1}$ to about 2000 cm$^{-1}$ and further from about 3000 cm$^{-1}$ to about 3100 cm$^{-1}$. Comparing it with the predetermined normal infrared absorbance spectra of known healthy subjects for the presence or absence of predetermined features such as increase or decrease of infrared absorbance, peaks at particular frequencies allows for accurate diagnosis of a disease of an organ, including most major organs such as a heart, lungs, stomach, liver, kidneys, brain, etc.

85 Claims, 30 Drawing Sheets

METHOD FOR BLOOD INFRARED SPECTROSCOPY DIAGNOSING OF INNER ORGANS PATHOLOGY

This invention uses the transmission of my co-pending provisional patent application "Method for Blood Infrared Spectroscopy Diagnosing of Inner Organs Pathology" series No. 60/216922 filed Jul. 8, 2000.

BACKGROUND OF THE INVENTION

1. Field of the Invention

The present invention related generally to an infrared (IR) spectroscopy method for the diagnosis of a disease state of a mammal such as a human being. More particularly, the method of the invention allows for specific and quick diagnosis of a variety of pathological conditions by analyzing the IR spectra of the patient's blood.

2. Description of the Prior Art

Diagnosis of a disease state of a human being is done using a variety of laboratory techniques. That, in conjunction with the general medical assessment of the patient's condition and symptoms allows a modern medical practitioner to determine in most cases the accurate diagnosis of a patient. It is well known that the ease of treatment depends greatly on the speed of such diagnosis. Thus, the sensitivity and precise discriminatory nature of the early diagnostic methods is very important in the effective treatment of patients.

There is a variety of sources of biological information about the general medical state of a patient that is used in the laboratory analysis as various tissue and cell samples as well as biological fluids that may be taken from a human being. An example of a biological fluid is blood, saliva, sweat, urine, semen, various gland secretions, joint lubricant fluids, lymphatic fluids, and so on. Typically, these fluid or tissue samples come from a specific organ so that a further laboratory analysis can reveal a certain pathologic condition of that particular organ. Blood, however, represents a universal fluid circulating throughout the human body and as such provides an almost unique cumulative source of biological information about the body as a whole as well as about individual organs.

A number of laboratory techniques have been developed in the recent years to study blood and other biological fluids and tissues. Many of them are aimed specifically to identify a certain pathological condition. However, no universal technique exists today that would allow for a quick, minimally invasive broad diagnosis of various organ specific conditions.

Usually, a simple elevation of a certain particle count in blood (such as leukocytes) is indicative of some inflammation process. Also, in recent years physicians have used such serum enzymes as creatine phosphokinase, lactic dehydrogenase, and aminotransferases, which are released in large quantities into the blood from necrotic tissue, for diagnostic purposes (for example for diagnosis of myocardial infarction or hepatitis). However, elevation of the serum enzymes level, as well as an increased level of leukocytes, is not organospecific and can be used only as an additional method of diagnostics. In that case, it is up to a physician to determine the exact organ or a group of organs responsible for a pathologic condition based on the symptom analysis, which may be not present, misleading, or confusing at times.

Among methods other than IR spectroscopy the method of microparticle enzyme immunoassay technology is the closest one to the suggested by us method by its aim and problem solving. This technique is used primarily for diagnostics of acute myocardial infarction and based on determination of a cardiac form of Troponin-1, which is the regulatory submit of the troponin complex associated with the actin thin filament within muscle cells. This method also has numerous limitations because any conditions resulting in myocardial cell damage can potentially increase cardiac Troponin-1 levels. These conditions include, but are not limited to: angina, unstable angina, congestive heart failure, myocarditis, cardiac surgery or invasive testing. Thus, this method provides an opportunity to diagnose the pathology of the specific organ, in this particular case the heart, but does not allow for making the specific diagnosis, that is for determining the particular heart disease. This leads to an incorrect diagnosis or a complete misdiagnosis of a patient with obvious consequences.

IR spectroscopy is a very sensitive chemical analysis method, which is routinely used by organic chemists and biochemists as a molecular probe. When infrared light is passed through a sample of an organic compound, some of the frequencies are absorbed and some are transmitted through the sample without being absorbed. As a result, this selective light absorbance is recorded as a chart by the machine and can be further used to determine the exact chemical composition of the sample under investigation. The term "IR spectroscopy" is used here to include laser-Raman spectroscopy, Raman con-focal laser spectroscopy, Fourier Transform infrared spectroscopy, or any other infrared spectroscopy technique. Organic applications of IR spectroscopy are almost entirely concerned with frequencies in the range of 650–4000 $cm^{-1}$. Frequencies lower than 650 $cm^{-1}$ are called far infrared and those greater than 4000 $cm^{-1}$ are called near infrared.

There are several important advantages in using this technique: results are obtained relatively quickly with less labor input than many other diagnostic techniques; the use of IR spectroscopy may provide a more precise information on the exact nature of a disease based on sampling of blood or other biological fluid; the method also allows to monitor the dynamics of the characteristic change, which is important in determining the exact stage of the disease.

It has been established in the prior art that certain diseases such as cancer can substantially change the IR characteristic of blood and some other biological fluids. Therefore, IR can be used to determine the presence or absence of cancer cells and even to determine whether the tumor is malignant or not.

Several US and international patents contain a description of utilizing IR spectroscopy for cancer diagnosis. U.S. Pat. No. 5,261,410 by Alfano discloses a method of determining the cancerous state of a human tissue, particularly in breast tissue after exposing a sample of that tissue to IR light. This method has limitations due to the need for tissue biopsy and also since it does not allow for diagnosis of other organs.

U.S. Pat. No. 5,186,162 by Oong illustrates a method of using the IR spectroscopy of a tissue sample or a culture for differentiation between the presence of normal and cancerous cells. The specimen under investigation may be a Papanicolu smear, a cervical specimen, an endocervical specimen, or a vaginal or uterus specimen. This method allows only for cancer diagnosis and is limited to the particular organ under investigation, which has to be suspected to contain cancerous cells even before the test is done. Thus, early diagnosis, especially other than cancer, is not feasible with this technique.

PCT Patent Application No. WO 97/14961 by Antipov describes the use of IR spectroscopy means for cancer diagnosis of various organs by analyzing the IR spectra of blood. This method allows for diagnosis of malignant disorders using the method of multiple irregular total internal reflection in the IR range. It utilizes blood as a source of biological information and allows for limited determination of a specific organ that contains cancerous cells. At the same time, in addition to requiring some special IR tools and exotic evaluation technique (which are not routinely available or known in the medical laboratory community), this method is limited to the diagnosis of other cancer only and does not allow for diagnosis of other important diseases and conditions such as inflammation of a certain internal organ.

A multivariate classification techniques are applied to spectra from cell and tissue samples irradiated with IR light according to the U.S. Pat. No. 5,596,992 by Haaland in order to determine if the samples are normal or cancerous. Classification can be made using infrared spectroscopy and analysis tools such as partial least square technique (PLS), principal component regression (PCR), and linear discriminant analysis. These classifications can be used to distinguish normal, hyperplastic, and neoplastic cells. Lymphatic fluid and tissue samples are used as the object of evaluation. The important limitation of this invention is that it requires a complex apparatus and a special microscope to be used and, as described before, allows only for cancer diagnosis.

U.S. Pat. No. 5,733,739 by Zakim discloses yet another IR spectroscopy machine-based cancer diagnosis method that allows differentiating between normal and abnormal (cancerous) cells. It has all the same limitations as the patents described above such as the need for a difficult organ tissue sample collection procedure (biopsy), which can not be done routinely but rather is performed very rarely due to its traumatic nature. In addition, this method can not include other than cancer diseases of internal organs.

Other than cancer diagnostic methods have also been suggested in the prior art. PCT Patent Application No. WO 97/32194 by Ashdown discloses the use of IR spectroscopy of blood or its components for determination of cellular immunity. Fourier Transform infrared spectroscopy is a preferred method of analysis according to this invention. This invention can be used for the determination of cellular immunity in patients with immunodeficiency, autoimmunity, and contact with infectious diseases, allergies, hypersensitivity, and cancer. It is also claimed to be used for determination of tissue transplant compatibility. Although a useful technique, this method by itself does not allow for differentiation between various internal organs as being the source of the disease let alone diagnosing other inflammatory conditions.

Chemical composition of a biological fluid such as blood can be determined using a near IR spectroscopy method described in U.S. Pat. No. 4,975,581 by Robinson. This method can be used effectively to determine the glucose level in blood and thus is of interest to diabetic patients. However, a simple determination of glucose level cannot be used effectively in diabetic diagnosis and screening since no determination can be made as to whether the source of higher glucose levels is physiologically acceptable or pathologic. This method is also claimed as capable of determining other blood parameters such as alcohol presence, fatty acid content and others and as such can be used as a replacement method to the currently employed techniques used for such determinations. However, it cannot produce clinically important information about the presence of inflammatory processes in various internal organs and therefore cannot be used as a broad diagnostic tool. Hemoglobin and hematocrit concentration in blood can be determined by using a near IR spectroscopy technique suggested by Osten in U.S. Pat. No. 5,830,133. Although fast and reliable, this method is limited to just the claimed purpose of hemoglobin evaluation and does not allow for internal organ diagnosis.

Eysel in the U.S. Pat. No. 5,473,160 suggests another specific application of IR spectroscopy of synovial fluid for diagnosing arthritis disorders. Osteoarthritis is diagnosed by comparing the synovial fluid near IR spectra retrieved from the patient with that of either a known healthy or diseased spectra. The method described in the patent is limited to only arthritis diagnosis.

Finally, my Russian Patent # SU 1,698,775 describes a method of determining the level of septic state in children using IR spectra. The presence of a "waved"-shape peak in the range of about 1095 $cm^{-1}$ to about 1105 $cm^{-1}$ of the same elevation as the liver portion of the chart is used as an indicator of a presepsis condition. Same at about 1080 $cm^{-1}$ points out to the initial stage of sepsis. A peak at about 1040 $cm^{-1}$ points to a medium level of sepsis, and finally a peak at about 1010 $cm^{-1}$ is associated with extended sepsis. This method is very useful but applicable only in small children and cannot differentiate between specific internal organs.

All IR spectroscopy techniques suggested in the prior art have similar limitations: they allow for selective diagnosis of some global disorders, mostly cancer, and sometimes capable of pointing to a certain internal organ. However, no universal technique exists for a broad diagnosis of organ specific disorders and the stage of their development in various internal organs, for example, a variety of inflammation conditions. Therefore, the need exists for such a broad diagnosis method.

SUMMARY OF THE INVENTION

Accordingly, it is an object of the present invention to overcome these and other drawbacks of the prior art by providing a novel machine-based method for a broad and comprehensive diagnosis of various pathological conditions of the human being by using IR spectroscopy of blood.

It is another object of the invention to provide a method for diagnosis for a variety of organ specific disorders using the IR spectra of patient's blood.

It is another object of the present invention to provide a method for early stage diagnosis of such conditions in patients of any age when conventional chemical analysis techniques are not capable of determining the diagnosis and no or little clinical symptoms are present.

It is a further object of the present invention to provide a method of monitoring the progression of the disease; the progression and results of the treatment of that disease; the effectiveness of the treatment therapy including the effect of medication; and the determination of the final cure from the disease, such method based on IR spectroscopy of blood.

It is yet a further object of the present invention to provide a method of fast and comprehensive diagnosis of a variety of pathological conditions of a human being soon after the patient is first presented to the medical professional.

It is another object of the invention to provide a method for selecting especially healthy people for certain special needs such as fighter pilots, astronauts, and other professions requiring physical endurance.

The method of the invention is based on the discovery that various major organs and their disease state can affect the IR spectra of human blood in a very specific individual way. In other words, certain ranges of frequencies in the IR spectra are indicative of certain specific organs and their pathologies.

The physiological importance of blood flow is that it transports all necessary ingredients to the internal organs and then removes all the components that have to be discarded by these organs. Whole blood contains over 1000 chemical components. Although IR spectroscopy is a very sensitive analysis tool, it cannot pick up reliably the presence of components having less than about 5% of the total mass of the sample. In a dried blood sample, the distribution of mass is such that most of it is represented by hemoglobin ranging from about 64 to 87%. The next highest number is lipids occupying about 8.8% of the total mass. All other components are less than 5% and should not affect significantly the IR spectra of the whole blood. Of course, special techniques are available to separate certain components from the whole blood. Themselves may in turn, use their selective IR spectra for diagnostic purposes.

Hemoglobin has a very complex chemical protein structure capable of reacting to the presence in blood of a variety of compounds. Such compounds entering the blood stream may be the result of metabolic processes, sub-components of certain cells that have to be carried away from diseased organs, or some other products of pathological processes in the body. All of these complex compounds have the ability to attach to hemoglobin proteins or in some other way effect its chemical structure. Since most of pathological reactions are organ specific, it is suggested that the unique compounds released in the blood stream can be used as an organ specific diagnostic tool provided that the information can be properly extracted and analyzed. The similar process takes place by the interaction of the above-mentioned pathologic products with phospholipids of erythrocytes.

Thus, the basis of the suggested by us method of diagnostics is not the identification of products of pathological processes by their spectra. The basis of this method is the change of blood spectra of a healthy human being (frequency shift, changes in the intensity and shape of the absorbance band) under the influence of intermolecular forces, which are brought about by the interaction of the bonds found in the whole blood of a healthy human being with the bonds of the corresponding metabolites and/or the products of pathological processes, entering the blood, if a specific disorder is taking place in the body.

Whereat, the concentration of the above-mentioned metabolites and/or the products of the decay of the specific organs and tissues, not found in the normal blood, is, as a rule, significantly lower than the threshold concentration which is necessary to diagnose a disorder of a specific organ using routine biochemical methods. The method of IR spectroscopy suggested by us detects organ specific molecules that precede the appearance of a whole complex of organ specific antigens in the blood.

It is possible that the mentioned above decay products of the specific organs can be determined by using immunology or other spectroscopy methods, based on the diagnosis of specific antigens or substances. However, in variety of illnesses, some of which are appendicitis, cholecystitis, pancreatitis e.t.c. it is impossible to make a diagnosis using the antigens or substances because in most cases the nature of this antigens or substances is unknown.

Besides, it should be noted that in overwhelming majority of cases (if not in all of them), the specific substance characteristic to a certain disease enters the blood in concentrations that are significantly less than 5% of the sample specimen and can not be seen by themselves. We can see this substance only if it is involved in some kind of intermolecular interaction with the hemoglobin bonds or that of phospholipids, which make up the basis for the blood spectra of a healthy human being.

Apparently, the said changes can be observed in those parts of spectra where chemical bonds absorb, which are mostly typical of (mostly absorbing) the substance entering the blood. If in the particular region of spectra the vibrations of hemoglobin bonds and/or the bond of phospholipids of erythrocytes are not found or faintly pronounced, we will observe the appearance of new ranges of absorbance absent in the blood spectra of a healthy human being, as for example, in the case of kidney disorder. However if in the specific region of the spectra the vibrations of hemoglobin bonds and/or the bonds of erythrocyte phospholipids are well pronounced (peaks, bands), then the result of intermolecular interaction will depend on the chemical nature and the number of bonds of the substance entering the blood.

As a rule, when a small amount of the substance enters the blood, the intensity of the corresponding absorbance range will increase, as for example in the case of acute myocarditis. By contrast when a large amount of the substance enters the blood, the intensity of the absorbance range will reduce, as for example in case of myocardial infarction. If the band of absorbance in norm is well pronounced, as for example in the region in which nervous system diseases are diagnosed, then the appearance of the products of the organ decay with the similar chemical bonds will result in the reduction of the absorbance band. The larger the amount of the decay products that enter the blood, the more significant the reduction of the absorbance band will be. For example, the brain injury of different degree of the severity would correspond to the different degree of the intensity reduction.

If the absorbance of the bonds of pathological products entering the blood occurs beyond the region where the bonds of substances found in the normal blood absorb, namely, next to the said region, then we would observe the absorbance range shift, as it happens in case of allergy or hepatitis.

At the same time, it is possible that the complex molecule of hemoglobin can be a molecular system of correspondence of the body, on which the condition of internal organs and the small changes of their metabolism are represented. These changes can be detected by us due to conformational changes of hemoglobin structure. It is similar to such known correspondence systems as reflexogenic areas of skin or the iris of an eye.

According to the method of the invention, a sample of patient's blood is taken and processed in a known way to allow for recording of IR spectra. One common way to prepare the blood sample is to dry the blood on glass plate and then remove the dried particles from the glass, mix with a filler and compress into a tablet or, in case of a liquid filler, place the suspension in a shape allowing the use of an IR recording apparatus. That example of a preparation technique is described in greater detail in my Russian Patent No. SU 1,698,775 and allows for easy transportation of the sample to the IR laboratory as well as for subsequent easy handling and storage. Once in the lab, the IR light is passed through the sample, the IR spectra of the patient's blood is recorded and compared with the general norm from known healthy subjects as well as with the IR charts from known disease conditions. The presence or absence of certain graphical elements on the chart in comparison to the normal or known disease chart is used for a variety of organ specific diagnostic purposes described in greater detail below.

The importance of the method in the present invention is in utilization of a newly discovered fact that specific organs and their respective disease states have particular and distinct ranges of frequency in which the IR absorbance spectra changes (specific pictures). Therefore, once a change or deviation from an established norm is detected, the range of frequency where the change occurs points out to a specific organ in question. Most of the times, based on a particular frequency with a pronounced change, clinician would be able to diagnose a specific pathological condition for a particular organ. The regions responsible for individual organs and organ systems are described below progressing from lower frequencies towards higher frequencies (FIGS. 1 and 2).

REGION 1, with frequency ranging from about 600 $cm^{-1}$ to about 700 $cm^{-1}$ is indicative of various hypoxic conditions associated with reduction in oxygen availability in organism. Hypothetically, in this region out-of-plane deformation vibrations of NH-bonds of hemoglobin and OCN-turns of the peptide groups of hemoglobin are observed, which increase by lack of oxygen in blood as a result of activation of vibrations of the iron-containing group of hemoglobin's hem.

REGION 2, with frequency ranging from about 700 $cm^{-1}$ to about 800 $cm^{-1}$, is indicative of liver failure. Hypothetically, in this region we observe deformation rocking vibrations of $CH_2$-groups in lipids, when they enter the blood with concentration significantly exceeding the norm, which occurs only in case of liver failure.

REGION 3, with frequency ranging from about 800 $cm^{-1}$ to about 1000 $cm^{-1}$ is indicative of disorders of gastrointestinal tract, kidneys, endocrine glands, as well as some types of cancer. This region, depending on the structure of chemical compounds shown in the spectra, is divided into Subregion 3A with frequency ranging from about 800 $cm^{-1}$ to about 900 $cm^{-1}$ and Subregion 3B with frequency ranging from about 900 $cm^{-1}$ to about 1000 $cm^{-1}$.

Subregion 3A is indicative of the disorders of colon, kidneys and endocrine glands. Hypothetically, if a colon disorders exists, in the range of about 850 $cm^{-1}$ to about 900 $cm^{-1}$ we observe deformation vibrations of NH, CH and CH=CH bonds of some toxic products, developed in large intestine as a result of proteins putrefaction (indole, skatole, phenylpropeonic, phenylacetic, parahydroxylphenyllactic acids, etc.). These products are normally not found, but can enter blood in very low amounts as the result of colon disorders.

Hypothetically, in the case of kidney disorders, in the range of about 850 $cm^{-1}$ to about 860 $cm^{-1}$ we observe deformation vibrations of NH, CH and CH=CH bonds of the uric acid, urea and decay products of protein-lipids antigens from damaged kidneys cells. It happens, when the concentration of the specified above metabolites in the blood deviate from the conventional standard, determined by the IR spectra.

Hypothetically, when an endocrine disorders take place in the body, in the range of about 880 $cm^{-1}$ to about 900 $cm^{-1}$ we observe deformation vibrations of CH and CH=CH bonds of a number of hypophysiotropic and steroid hormones. The spectra of a healthy human being do not show these hormones.

Subregion 3B, is indicative of the disorders of stomach, pancreas, small intestine and some types of cancer. Hypothetically, if a patient suffers from stomach disorders, in the range of about 930 $cm^{-1}$ to 950 $cm^{-1}$ we observe deformation vibrations of NH and CH bonds of protein products, which are a result of stomach mucous membrane inflammation.

Hypothetically, in the area of about 940 $cm^{-1}$ we can observe deformation vibrations of NH and CH bonds of protein products, which form as a result of pancreas tissue inflammation.

Hypothetically, in case of duodenum, jejunum and ileum disorders, in the frequencies ranging from about 950 $cm^{-1}$ to about 1000 $cm^{-1}$ we observe deformation vibrations of CH and CH=CH bonds of phospholipid products, as well as NH and CH bonds of protein products formed by inflammation of these organs.

Hypothetically, if a patient suffers from certain types of cancer which correlate with immunodeficiency conditions, in the area of about 908 $cm^{-1}$ we observe deformation vibrations of CH and NH bonds of protein-lipid antigens and RNA from the cancerous tissue.

REGION 4, with frequency ranging from about 1000 $cm^{-1}$ to 1140 $cm^{-1}$, is indicative of the disorders of liver and immune system (different kinds of immunodeficiency and allergy). This region, depending on the functional characteristics, can be subdivided into Subregion 4A with frequency ranging from about 1100 $cm^{-1}$ to 1140 $cm^{-1}$ or more exactly the peak at a frequency of about 1130 $cm^{-1}$, and Subregion 4B with frequency ranging from about 1000 $cm^{-1}$ to 1100 $cm^{-1}$.

Subregion 4A, especially the peak at a frequency of about 1130 $cm^{-1}$, to be exact, is indicative of normal liver function. This subregion represents a spectra of SH-groups of hemoglobin, consisting of sulfur containing amino acids (cysteine, cystine and methionine) and responsible for respiratory function of hemoglobin. Also, sulfur-groups of hemoglobin determine its reactivity, that is its ability to react not only with oxygen but also with other compounds. In connection with this, when toxic metabolites, products of decay of organs and tissues enter the blood and/or the liver detoxification function is upset, the peak at a frequency of about 1130 $cm^{-1}$ disappears or modifies. This is a result of interaction between SH-groups of hemoglobin and the above-mentioned toxins, as well as of the formation of other compounds with a new conformation structure. We cannot also rule out that sulfa lipids of erythrocytes and possibly ether-sulfonic acids, which are associated with liver detoxification function, form the peak at about 1130 $cm^{-1}$. In view of this, the normal position of the peak in the range of about 1130 $cm^{-1}$ defines the normal liver condition, while its disappearance or changes in its conformation correlate with liver function disorders.

Subregion 4B is indicative of the disorders of the liver (hepatitis) and such immune disorders as allergy; T- and B-cells immunodeficiency; and nonspecific phagocytic immunodeficiency (sepsis: SU Patent No. 1,698,775).

Hypothetically, when hepatitis takes place in the frequency range of about 1030 $cm^{-1}$ to about 1000 $cm^{-1}$ we observe vibration modes of glycogen. In case of allergy in the range of about 1080 $cm^{-1}$ to about 1090 $cm^{-1}$ we observe the vibrations of C—O—P bonds of phospholipids from decayed cells, and P—O bonds of ADP and AMP. If a patient suffers from T- and B-cells immunodeficiency associated with a tumor, we observe vibrations of C—O—P bonds of DNA and RNA at frequencies of about 1030 $cm^{31}$ 1 and 1060 $cm^{-1}$.

Hypothetically, if nonspecific phagocyte immunodeficiency (sepsis) exists, we observe vibrations of C—O—P and P—OH bonds of all above-mentioned components, namely ADP, AMP, DNA, RNA, phospholipids, as well as vibrations of metal containing groups of cytochromes from decayed mitochondria of cells.

REGION 5, with frequency ranging from about 1140 $cm^{-1}$ to about 1350 $cm^{-1}$, is indicative of the disorders of the heart. Depending on the chemical compounds, revealed in this region of the spectrum, we subdivide this region into three subregions:

Subregion 5A, with frequency ranging from about 1140 cm$^{-1}$ to about 1200 cm$^{-1}$, primarily the peak at a frequency of about 1160 cm$^{-1}$, reflects the condition of a myocardial muscle in norm (FIG. 1);

Subregion 5B: the straight descendent under acute angle line in the range of about 1180 cm$^{-1}$ to about 1200 cm$^{-1}$, reflects the condition of the heart valves in norm and/or absence of heart insufficiency (FIG. 1), and Subregion 5C: the area ranging from about 1200 cm$^{-1}$ through about 1350 cm$^{-1}$, including a big peak at a frequency of about 1250 cm$^{-1}$, reflects the cardiac rhythm in norm (FIG. 1).

Changes of IR absorbance in these areas reflect the appropriate pathologies of myocardial muscle, disorders of heart valves and/or presence of heart insufficiency of different degree, and cardiac arrhythmia.

Hypothetically, the peak at about 1160 cm$^{-1}$ (Subregion 5A) normally is the spectra of C—O—C and P—O—C bonds of phospholipids of erythrocytes. When C—O—C and P—O—C bonds of phospholipids from the damaged heart cells, especially cardiolipin (serinephosphatide) appears in the blood and in the spectra, it allows for diagnosis of myocard diseases and heart valves disorders, including heart failure.

Hypothetically, the peak at about 1250 cm$^{-1}$ (Subregion 5C), normally and primarily represents amid III of the hemoglobin peptid chain (NH turn in-plane of peptide chain of hemoglobin), and to the lower extend, P=O and C—O—C bonds of phospholipids of erythrocytes. The appearance in the blood and in the spectra of P=O, P—OH and C—O—C bonds of phospholipids, and, probably, NH bonds of protein from the damaged myocard cells, in the range of about 1200 cm$^{-1}$ to about 1350 cm$^{-1}$ strictly correlates with the heart rhythm disorder, that is evident of the damage of the heart conductive system, and allows for diagnosis of various types of arrhythmia.

REGION 6 (MIXED), with frequency ranging from about 1100 cm$^{-1}$ to about 1200 cm$^{-1}$ includes confluence of Subregion 4A (which is indicative of the normal liver function) and Subregion 5A (which is indicative of the normal myocard function of the heart). Simultaneous increase of IR absorbance in this region, especially of the peaks at about 1130 cm$^{-1}$ and 1160 cm$^{-1}$, is indicative of the inflammation disorders of the upper respiratory tract and lungs. Hypothetically, that is because by the above-mentioned diseases one can see in this region P=O and P—OH vibrations of ATP; SS and SH vibrations of sulfolipids and also C—O—C and P—O—C vibrations of phospholipids, which appear in the blood as a result of lung cells damage and throw of ATP into the blood, which is necessary to provide energy for a general inflammation process.

REGION 7, with frequency ranging from about 1400 cm$^{-1}$ to about 1700 cm$^{-1}$, is indicative of the disorders of brain and central nervous system. Depending on the degree of severity of brain disorders, shown in the spectra, we subdivided this region into Subregion 7A, with frequency ranging from about 1400 cm$^{-1}$ to about 1500 cm$^{-1}$, or more definitely, the peaks at frequencies of about 1410 cm$^{-1}$ and 1460 cm$^{-1}$. And Subregion 7B, with frequency ranging from about 1500 cm$^{-1}$ to about 1700 cm$^{-1}$, or more definitely, the peaks at frequencies of about 1550 cm$^{-1}$ and 1650 cm$^{-1}$.

Hypothetically, the peak at a frequency of about 1410 cm$^{-1}$ (Subregion 7A) represents symmetric CO stretching vibrations and symmetric CH$_3$ bending vibrations of hemoglobin amino acids. The peak at a frequency of about 1460 cm$^{-1}$ (Subregion 7A) is probably indicative of CH$_2$ bending vibrations and asymmetric CH$_3$ bending vibrations of all components of the whole dry blood.

If a brain damage take place, the appearance in the blood of the protein products of the nerve tissue decay, namely, of neuroglobulin and neurostromin, containing CO bonds of amino acids, results in the changes of the peak conformation at a frequency of about 1410 cm$^{-1}$. And the appearance of even small amounts of products of nerve cell membranes decay, containing CH$_2$ and CH$_3$ bonds, results in the changes of peak conformation at a frequency of about 1460 cm$^{-1}$.

On the whole, the changes in spectra in the Subregion 7A are indicative of less severe, typical for early stage of central nervous system diseases and/or functional brain disorders, such as a minor degree of intracranial hypertension, neurosis or early stage of convulsion syndrome.

Hypothetically, in Subregion 7B the peak at a frequency of about 1550 cm$^{-1}$ represents primarily asymmetric CO stretching vibrations and, secondly, NH bending and CN bending vibrations of hemoglobin amino acids. The peak at a frequency of about 1650 cm$^{-1}$ represents primarily CO bonds of a-spiral of the hemoglobin peptide chain and, secondly, CO bonds of acetalphosphatides (plasmalogens) of erythrocyte lipids and N≡(CH$_3$)$_3$ bonds of cholinephosphatides (lecithins), which are part of erythrocyte lipids.

When brain is severely damaged, the blood shows not only the products of protein decay of brain tissues, containing asymmetric CO bonds with vibrations at a frequency of about 1590 cm$^{-1}$ and NH bending vibrations at a frequency of about 1570 cm$^{-1}$. Also one can see the products of a more severe brain damages, such as a sphingomyelin with asymmetric CO and CN bonds vibrations in the frequency range of about 1550 cm$^{-1}$–1655 cm$^{-1}$. These products consist of sphingomyelin, phosphatidylserine, phosphatidylcholine and other phosphoric acids with CC-cis bonds, vibration of which one can see at frequencies of about 1660 cm$^{-1}$ and 1670 cm$^{-1}$. Since phosphatidylcholine also contain with N≡(CH$_3$)$_3$ bonds, one can identify vibrations at a frequency of about 1630 cm$^{-1}$. On the whole, the changes in spectra in the Subregion 7B are indicative of more severe damages of brain and central nervous system, such as head trauma, hypoxic encephalopathy with hemorrhage, etc.

REGION 8, with frequency ranging from about 3000 cm$^{-1}$ to about 3100 cm$^{-1}$, especially the peak at a frequency of about 3060 cm$^{-1}$, is indicative of severe chronic infections, such as pulmonary tuberculosis. Hypothetically, the peak at a frequency of about 3060 cm$^{-1}$ primarily represents —NH$_3^+$ bond of associated molecules of secondary amids, constituting side chains and terminal groups of the hemoglobin protein molecules. Also, in the frequency range of about 3010 cm$^{-1}$ to about 3095 cm$^{-1}$ one can see =C—H stretching vibration of erythrocyte phospholipids.

In the case of severe chronic infections, including pulmonary tuberculosis, the intoxication of the body is strongly pronounced, which results in products of protein decay entering the blood. These products contain —NH$_3^+$ bond of associated molecules of secondary amids, constituting side chains and terminal groups of protein molecules. Besides, we cannot rule out the appearance in blood of great amounts of decay products of the tuberculosis bacillus itself, particularly, of the tuberculostearic acid, containing =C—H bonds, which absorb in the range of about 3010 cm$^{-1}$ to about 3095 cm$^{-1}$.

On the base of outlined above yet another application of the method is that it allows for monitoring the progression of the disease or the success of the treatment, by comparing subsequent blood samples spectra to the initial one.

Also, the use of the method is possible when selecting the healthiest men for the professions where extreme physical endurance is needed.

In addition the method of the invention allows for rapid and accurate early diagnosis, frequently pointing out to the initial stage of the disorder when no clinical manifestations are yet observed.

The method is also particularly useful when a physician cannot count on the patient's response, as for example, in case of a patient being unconscious after an accident or with a pediatric patient.

Another advantage is that the method of the present invention allows for a rapid differentiation between a number of likely medical conditions, all of them presenting with similar clinical symptoms. This method has real advantages because it gives us a chance to simultaneously diagnose different organs pathology in contrast to some well known diagnostic methods such as ECG or EEG, which can be used for diagnostic diseases of only one organ (heart or brain).

The method can be used in insurance medicine, military and space medicine, forensic and veterinary medicine, pharmacology and parasitology. It can also be helpful for diagnostics of some oncology (retroperitoneal lymphoma) and infectious diseases (HIV, hepatitis B, etc.) on the earliest stage, when no clinical manifestations and antibodies are present. Moreover, the method can be used in different branches of biology (zoology, entomology, ichthyology, ornithology) and botany.

BRIEF DESCRIPTION OF THE DRAWINGS

A more complete appreciation of the subject matter of the present invention and the various advantages thereof can be realized by reference to the following detailed description, in which reference is made to the accompanying drawings in which.

DETAILED DESCRIPTION OF THE PREFERRED EMBODIMENT OF THE INVENTION

A detailed description of the present invention follows with reference to accompanying drawings, in which like elements are indicated by like reference letters and numerals. Solid lines are used to illustrate normal, non-diseased conditions, while dashed lines are used to show how the solid line would change in case of a particular disorder. Dashed lines should be generally projected vertically upwards or downwards and substituted in place of corresponding solid lines to gain appreciation of the exact nature of the full chart. The following description is arranged along the IR spectra from the lower levels to the higher levels. One should appreciate that in this case various diseases for a particular organ may be described in different parts of the text due to the fact that different portions of the IR spectra may be affected.

Figure 1:
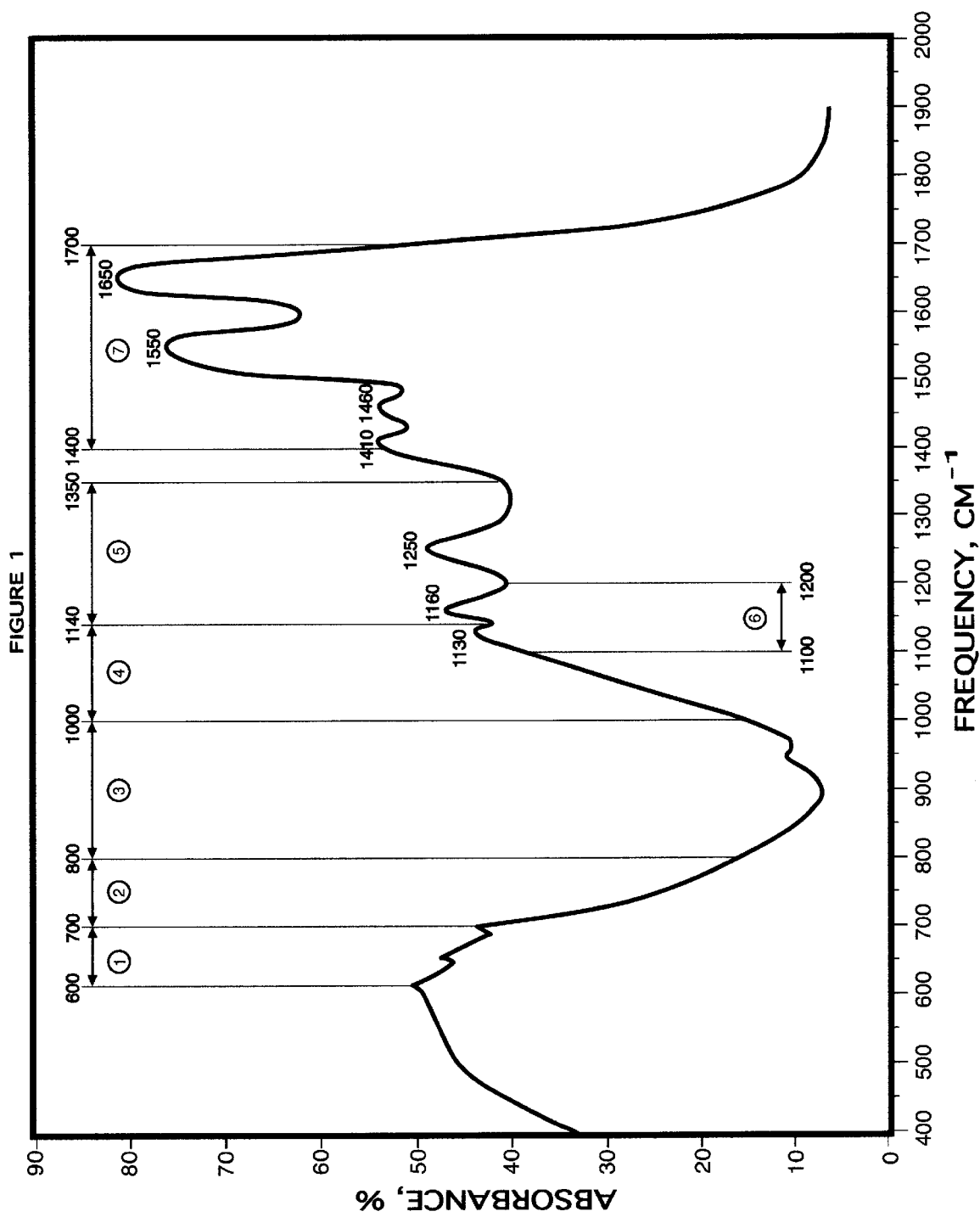
FIG. 1 is a normal chart of the blood IR absorbance spectra in the range of about 400 cm$^{-1}$ to about 2000 cm$^{-1}$.
Figure 2:
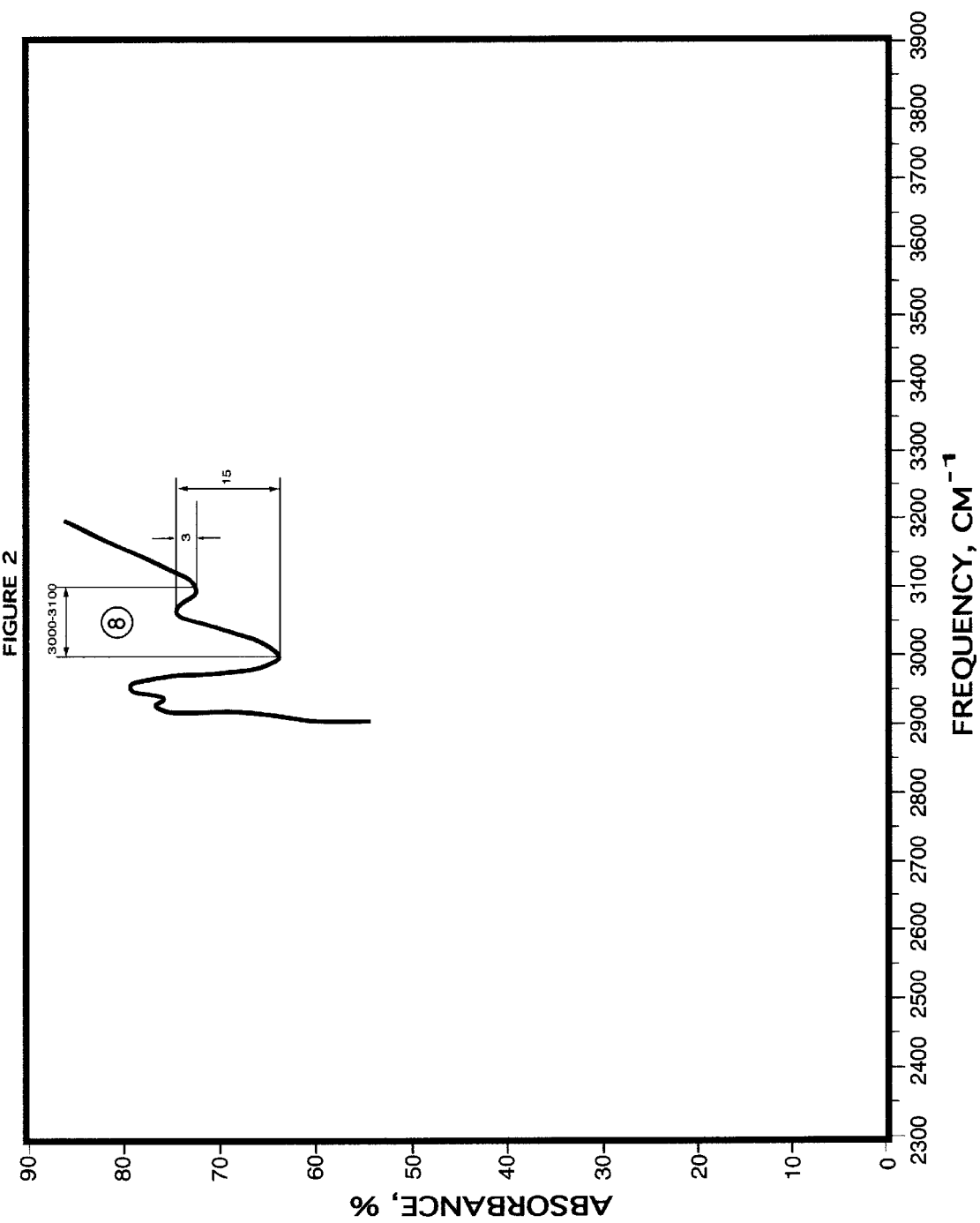
FIG. 2 is a normal chart of the blood IR absorbance spectra in the range of about 3000 cm$^{-1}$ to about 3100 cm$^{-1}$.

FIGS. 1 and 2 illustrate a normal IR absorbance spectra recorded accordingly in the range of about 400 $cm^{-1}$ to about 2000 $cm^{-1}$, and of about 3000 $cm^{-1}$ to about 3100 $cm^{-1}$. The mehod of the instant invention is based on the discovery that various groups of organs effect the normal chart in a different way and further that main organs have certain frequency "regions" on the chart that indicate their specific condition. FIGS. 1 and 2 illustrate such general regions of frequency ranges:

REGION 1, with frequency ranging from about 600 $cm^{-1}$ to about 700 $cm^{-1}$ is indicative of various hypoxic conditions, associated with reduction in oxygen availability.

REGION 2, with frequency ranging from about 700 $cm^{-1}$ to about 800 $cm^{-1}$ is indicative of hepatic failure (when blood lipids concentration is above norm). Normally, lipids do not affect this region. However, liver disorders may cause an excessive number of lipids, which would be reflected in this region of the IR spectra.

REGION 3, with frequency ranging from about 800 $cm^{-1}$ to about 1000 $cm^{-1}$ is indicative of disorders of stomach, intestinal tract, kidneys, endocrine glands, as well as some types of cancer.

REGION 4, with frequency ranging from about 1000 $cm^{-1}$ to about 1140 $cm^{-1}$ is indicative of disorders of liver and immune system, including different kinds of immunodeficiency and allergy.

REGION 5, with frequency ranging from about 1140 $cm^{-1}$ to about 1350 $cm^{-1}$ is indicative of the disorders of the heart.

REGION 6 (MIXED), with frequency ranging from about 1100 $cm^{-1}$ to about 1200 $cm^{-1}$, only in case of simultaneous increase of IR absorbance, especially of the peaks at about 1130 $cm^{-1}$ and 1160 $cm^{-1}$, is indicative of the disorders of lung and upper respiratory tract.

REGION 7, with frequency ranging from about 1400 $cm^{-1}$ to about 1700 $cm^{-1}$ is indicative of the disorders of brain and central nervous system.

REGION 8, with frequency ranging from about 3000 $cm^{-1}$ to about 3100 $cm^{-1}$, is indicative of severe chronic infections, such as pulmonary tuberculosis.

The following is the description of organ specific pathologic conditions and their effects on the IR spectra in the above-mentioned regions of frequency. As can be easily understood, with the underlying condition deterioration, the change on the chart becomes more pronounced. That can be used to determine not only the fact of the presence of a certain disorder, but also the degree of the disease progression, as well as the degree of treatment success. Dashed lines used in the drawings to illustrate certain pathologies are indicative of quite severe cases of these pathologies. A medical practitioner can use the method of the present invention even if the chart lines are initially approaching the dash-lined examples—this would be the indication of the initial stages of the disease.

Region 1: Frequency of 600 $CM^{-1}$ to 700 $CM^{-1}$

This region is indicative of hypoxia or the lack of proper tissue and organ oxygenation caused by various reasons.

Figure 3:
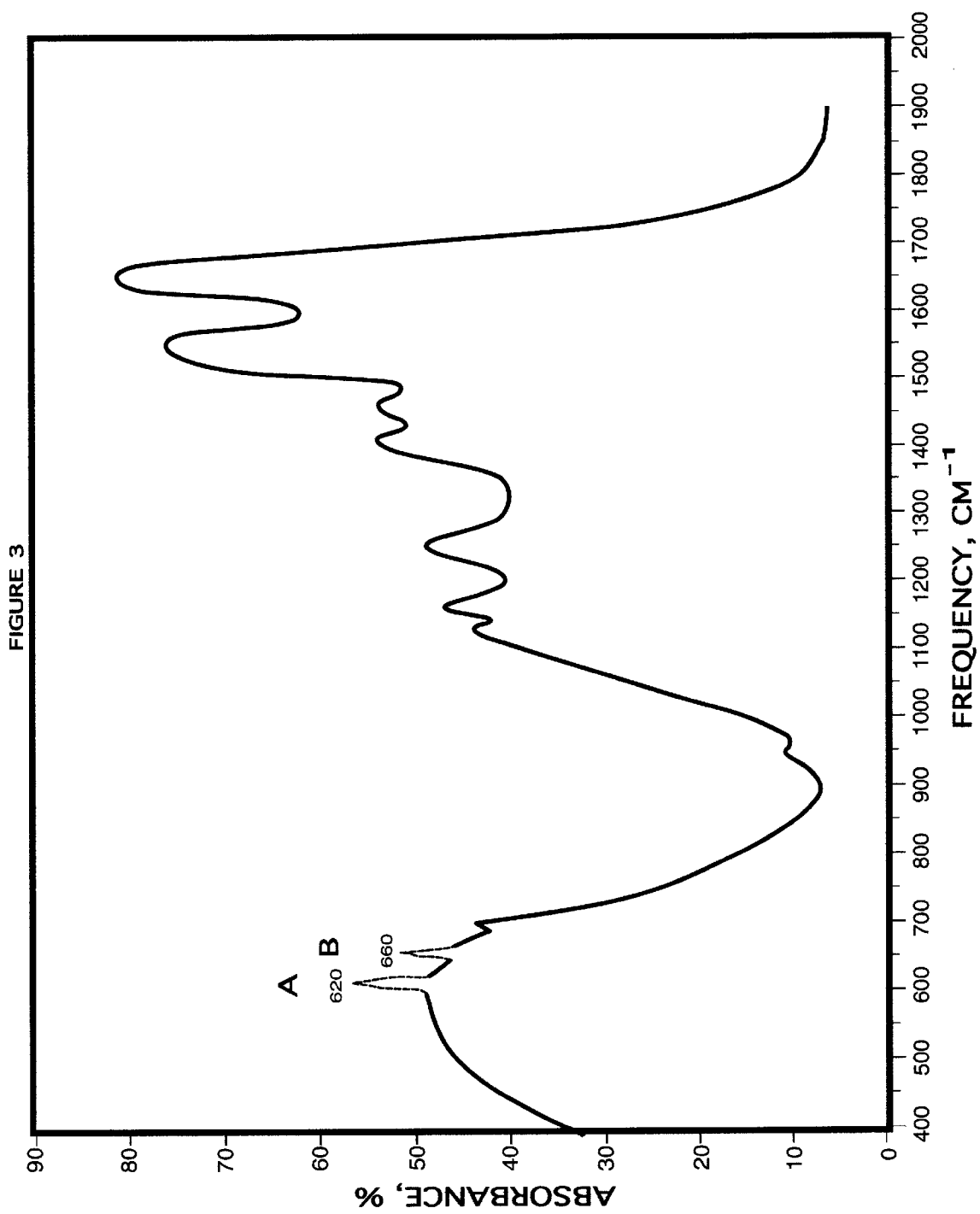
FIG. 3 is a chart illustrating the change from the normal chart (solid line) typical of various pathological hypoxic conditions of organism, such as hypoxia and asphyxia (shown in dashed lines).

FIG. 3 illustrates an example of the presence of two pronounced sharp peaks in the curve of the IR absorbance spectra, which normally contains just two small rounded peaks. One peak at the frequency of about 620 $cm^{-1}$ points of asphyxia of neonates or, in case of adult patients, indicates recent forceful strangling and as such can be used in forensic medicine. Another peak at the frequency of about 660 $cm^{-1}$ indicates hypoxia cause by heart failure such as cardiac asthma.

Region 2: Frequency of 700 $cm^{-1}$ to 800 $cm^{-1}$

Figure 4:
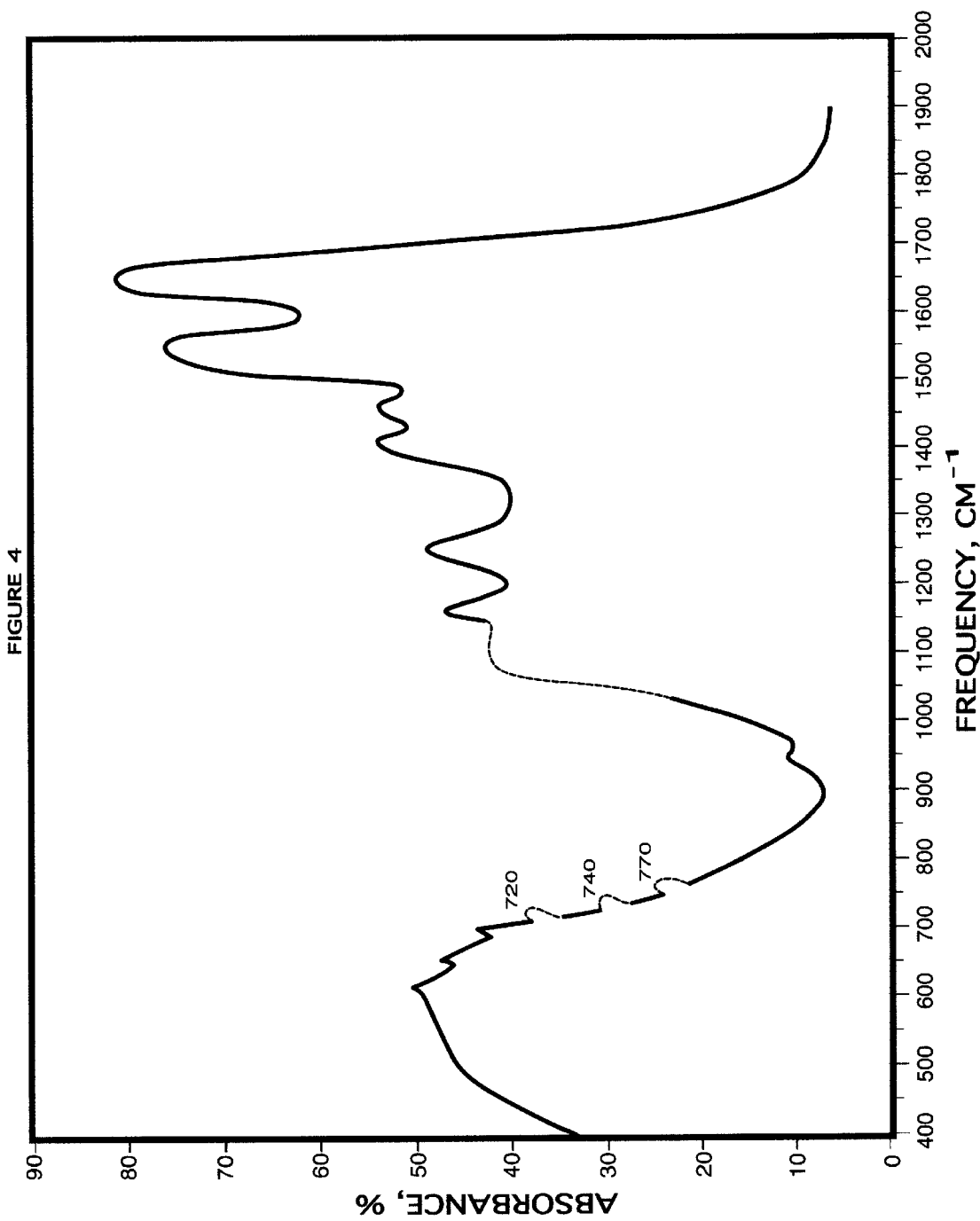
FIG. 4 is a chart illustrating the change from the normal chart (solid line) due to various pathological conditions of liver failure (shown in dashed lines).

This region is generally reflective of the liver failure. Lipids are usually not reflected on the normally smooth line of this part of the IR spectra. However, pathological fat infiltration of the liver can cause lipids to effect the IR spectra. Three wave-like peaks at the frequencies of about 720, 740, and 770 $cm^{-1}$ as illustrated on FIG. 4, are used to diagnose this condition. This phenomenon usually corresponds with increase in the IR absorbance in the area of frequency of about 1100 $cm^{-1}$ and the lack of a normally present peak in the area of about 1130 $cm^{-1}$. Other liver diseases are described below on FIG. 13.

Region 3: Frequency of 800 $CM^{-1}$ to 1000 $CM^{-1}$

Figure 5:
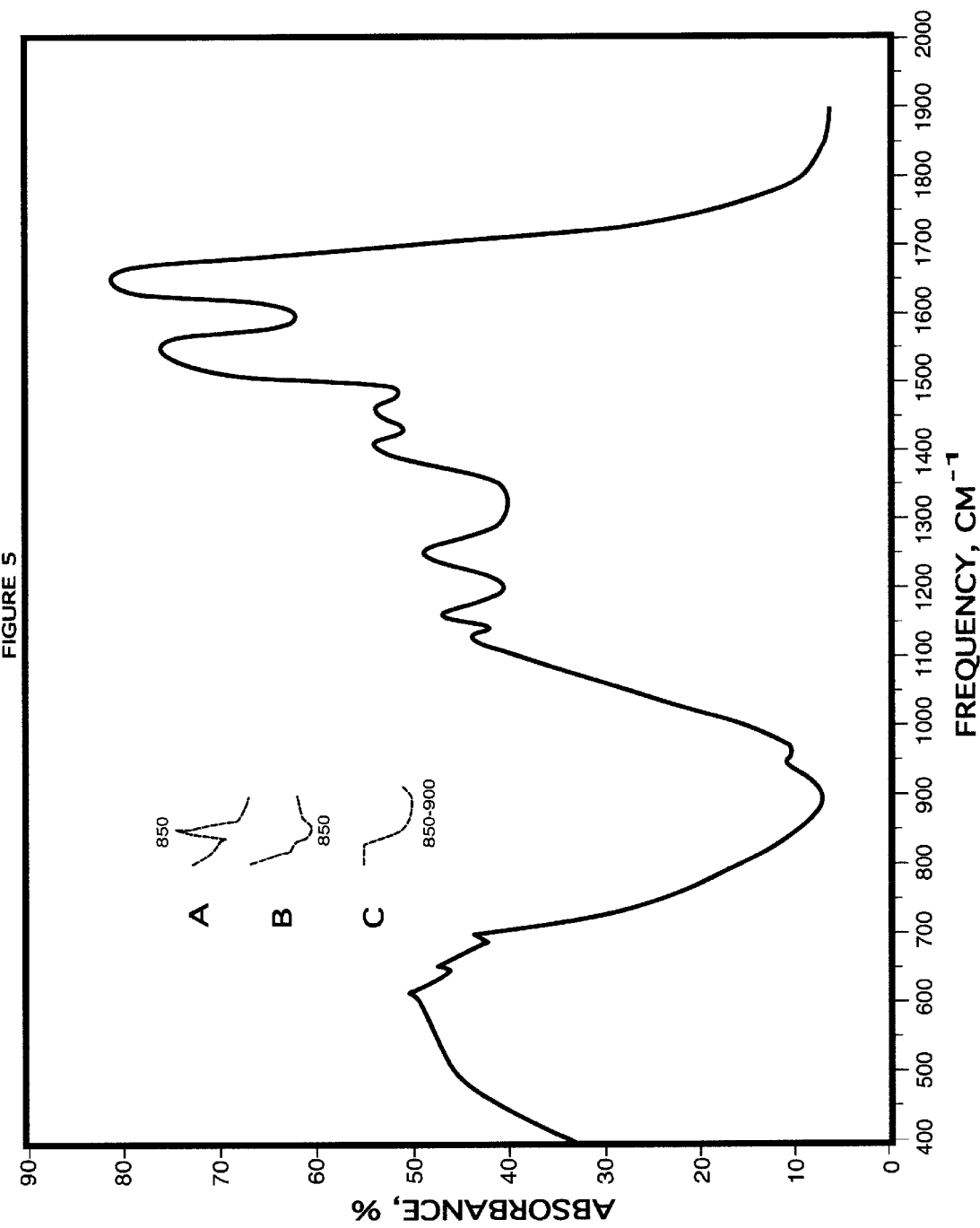
FIG. 5 is a chart illustrating the change from the normal chart (solid line) due to various pathological conditions of kidney and colon, such as acute and chronic nephritis and colitis (shown in dashed lines).

FIG. 5 illustrates possible line deviations A, B and C from the normally gradually declining line of that region of the IR spectra. The part of this region with frequencies ranging from 800 cm$^{-1}$ to 900 cm$^{-1}$ is generally indicative of the condition of colon, kidneys and endocrine glands.

More specifically, pathology of kidneys is determined in the range of about 850 cm$^{-1}$ to about 860 cm$^{-1}$, hypothetically, by the presence of uric acid in concentration more than normal (regarding IR normal absorbance) and/or with appearance in the blood of protein-lipid complexes from damaged renal cells, which is normally not there.

Acute nephritis or kidney inflammation is diagnosing by the sharp peak at the frequency of about 850 cm$^{-1}$ (line A). This condition in some cases (exacerbation of chronic recurrent pyelonephritis, for example) does not have clinical and/or laboratory symptoms initially and cannot be diagnosed by any other means. At the same time, it leads to renal failure, which is important to recognize as early as possible.

Chronic renal inflammation usually coinciding with kidney stones and/or so called "urinary sand" is recognized by the presence of a negative rounded indentation in the IR spectra in the range of about 850 cm$^{-1}$ to about 860 cm$^{-1}$ (as shown on line B). As previously mentioned, the more pronounced the feature of the chart, the more advanced is the stage of the disease.

Figure 9:
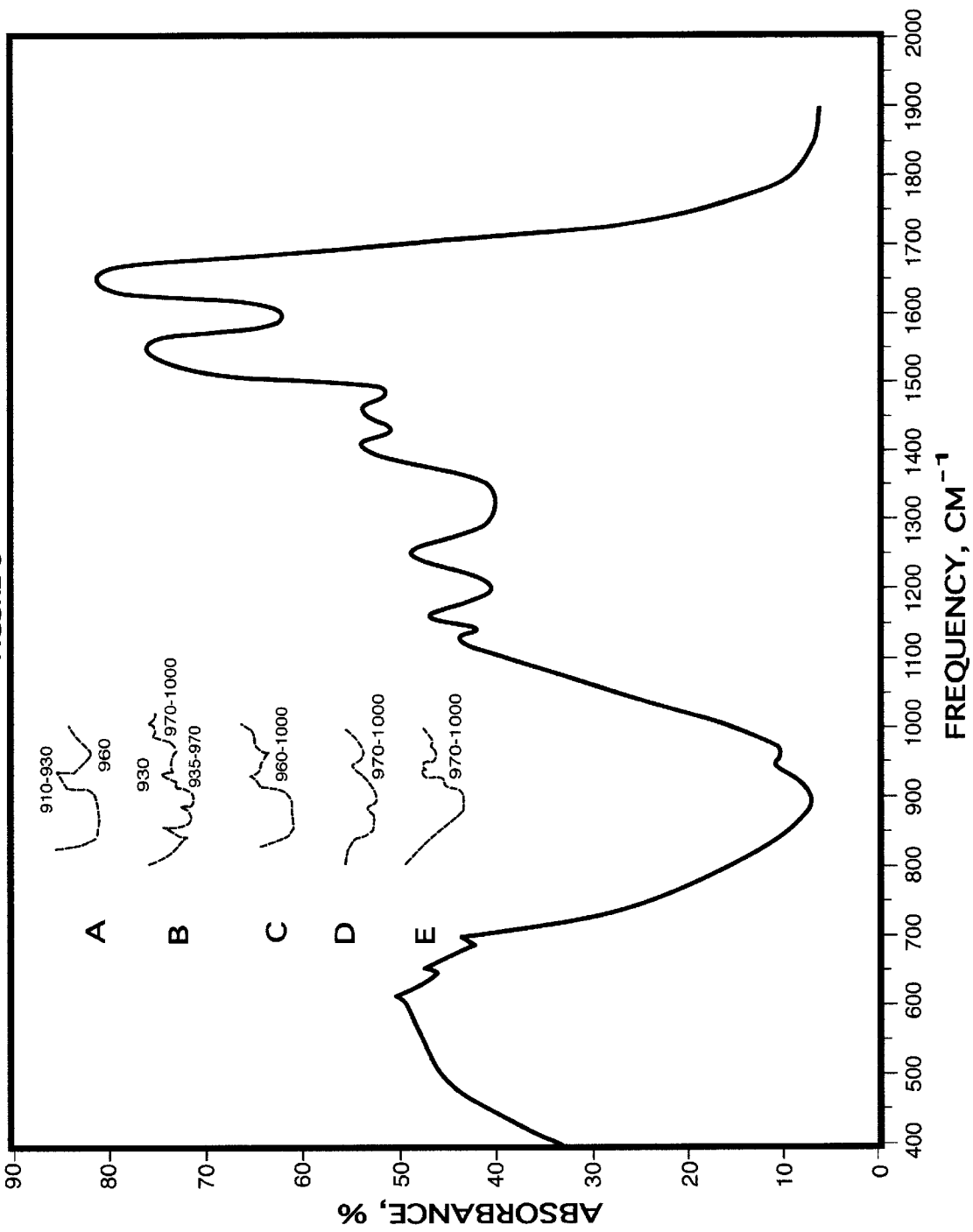
FIG. 9 is a chart illustrating the change from the normal chart (solid line) due to various pathological conditions of small and large bowel, such as different kinds of acute appendicitis, diverticulitis and pathologic conditions with similar clinical symptoms like paranephritis and acute mesenteric adenitis (shown in dashed lines).
Figure 10:
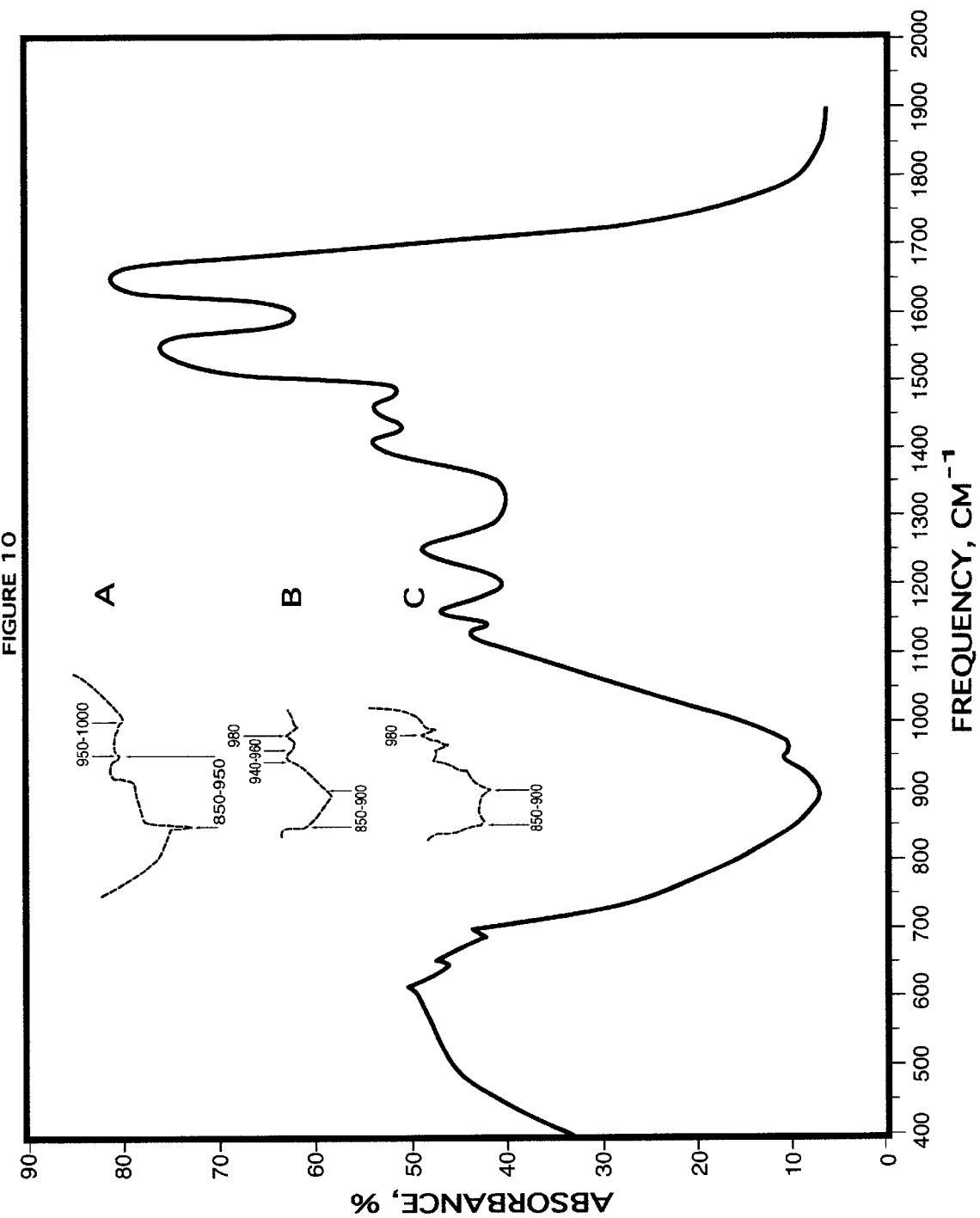
FIG. 10 is a chart illustrating the change from the normal chart (solid line) due to various infectious and parasitic pathological conditions of small and large bowel, such as brucellosis, lambliasis and enterobiasis (shown in dashed lines).

The general reduction in absorbance intensity in the frequency range of about 850 cm$^{-1}$ to about 900 cm$^{-1}$ (negatively rounded curve on line C) indicates large intestinal disorders such as chronic colitis or lack of or reduction in the normal number of naturally occurring bacteria. Yet lower levels of the curve of line C indicate the more advanced stages of this disorder. Reference is also made to FIG. 10, line A for a kind of acute colitis caused by brucellosis. Another reference is made to FIGS. 9 and 10 for other large intestine disorders.

Figure 6:
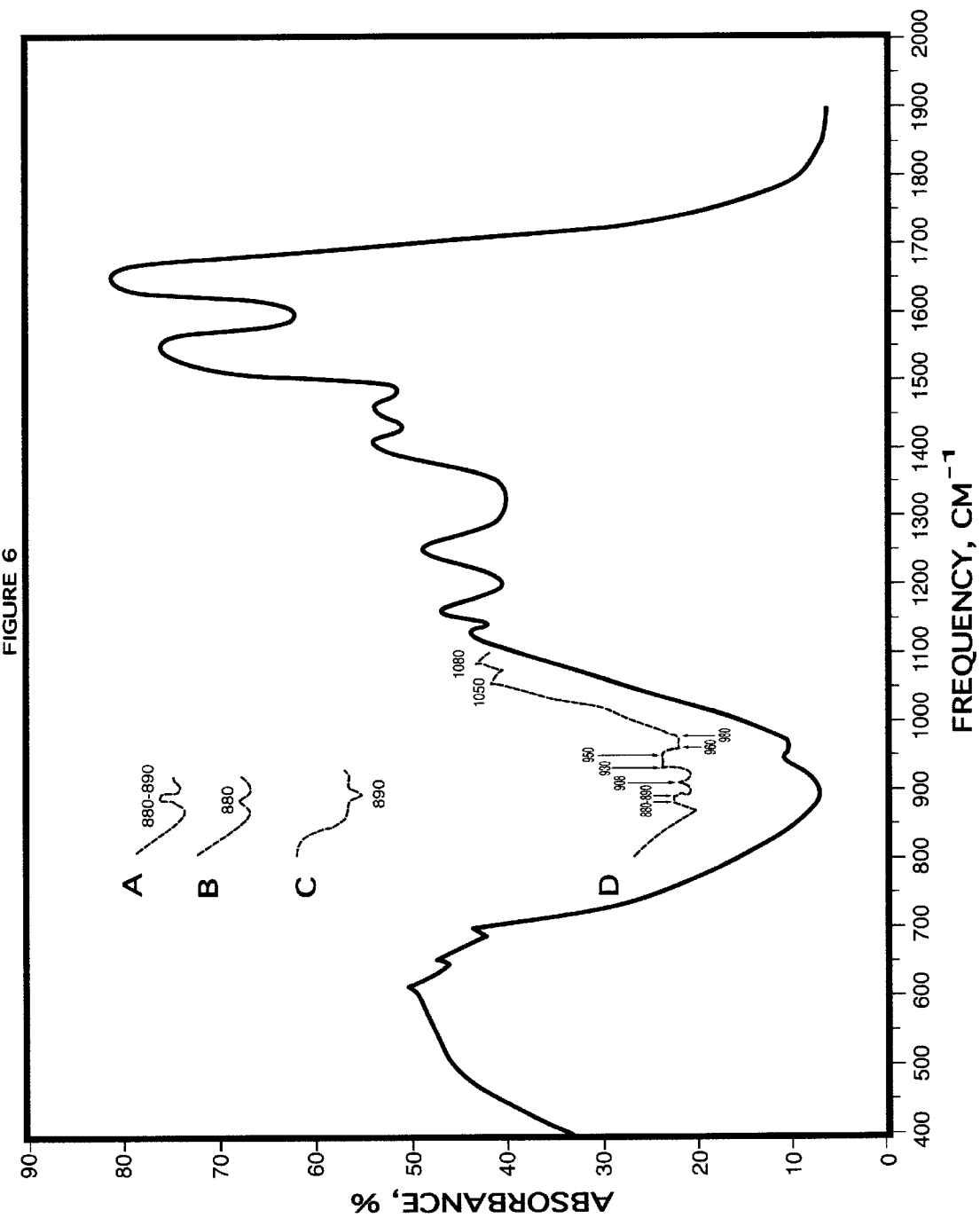
FIG. 6 is a chart illustrating the change from the normal chart (solid line) due to various pathological conditions of endocrine system, such as pituitary dwarfism, obesity, hyperthyroidism, as well as the condition of pigmented nevi (shown in dashed lines).

FIG. 6 illustrates the disorders of endocrine system in the range of about 880 cm$^{-1}$ to about 900 cm$^{-1}$. More specifically, a rounded peak on line A at a frequency of about 880 cm$^{-1}$–900 cm$^{-1}$ calls for the diagnosis of pituitary dwarfism.

A sharp small peak at a frequency of about 880 cm$^{-1}$ calls for the diagnosis of diencephalic syndrome, leading to obesity, shown on line B.

A wide based slightly rounded negative peak at a frequency of about 890 cm$^{-1}$ is indicative of a thyroid gland dysfunction hyperthyroidism (goiter) or decrease of 17-hydrocorticoid excretion as a result of increase in thyroid hormones level, shown on line C.

Separately, as shown on line D, a genetically determined tumor with endocrine disorders and immunodeficiency causing congenital pigmented nevi can be identified by a presence of a bulky "trapezium"-like peak with a flat top at a frequency of about 880 cm$^{-1}$–890 cm$^{-1}$. This peak with a wide base, ranging from about 870 cm$^{-1}$ to about 895 cm$^{-1}$ is indicative of endocrine disorders, correlated with congenital pigmented nevi. (REGION 3, Subregion 3A).

Since this disease is affecting other organs and systems of organs one can see an additional small sharp peak at a frequency of about 908 cm$^{-1}$, reflecting tumor disease, correlated with congenital pigmented nevi. (REGION 3, Subregion 3B).

Also dramatically change in shape of a peak at a frequency of about 930 cm$^{-1}$–950 cm$^{-1}$. When congenital pigmented nevi is occur, this peak is transformed into a descendent "step"-like line. Whereat there is the first step: at a frequency of about 930 cm$^{-1}$–950 cm$^{-1}$ and the second step: at a frequency of about 960 cm$^{-1}$–980 cm$^{-1}$, reflecting influence of this illness on stomach condition (REGION 3, Subregion 3B).

Figure 11:
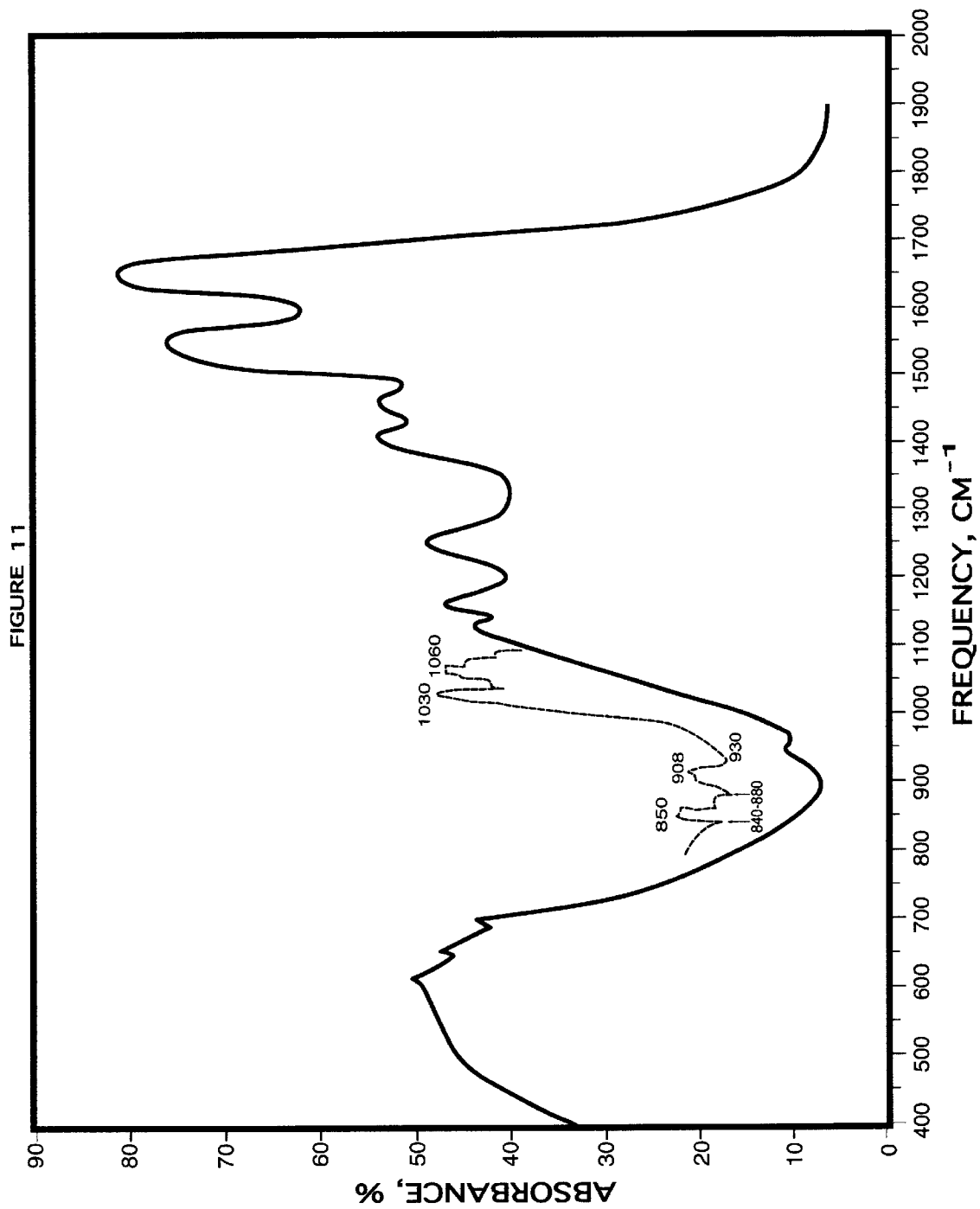
FIG. 11 is a chart illustrating the change from the normal chart (solid line) due to various pathological conditions associated with genetically determined tumors with immunodeficiecy such as retroperitionial lymphoma (shown in dashed lines).
Figure 14:
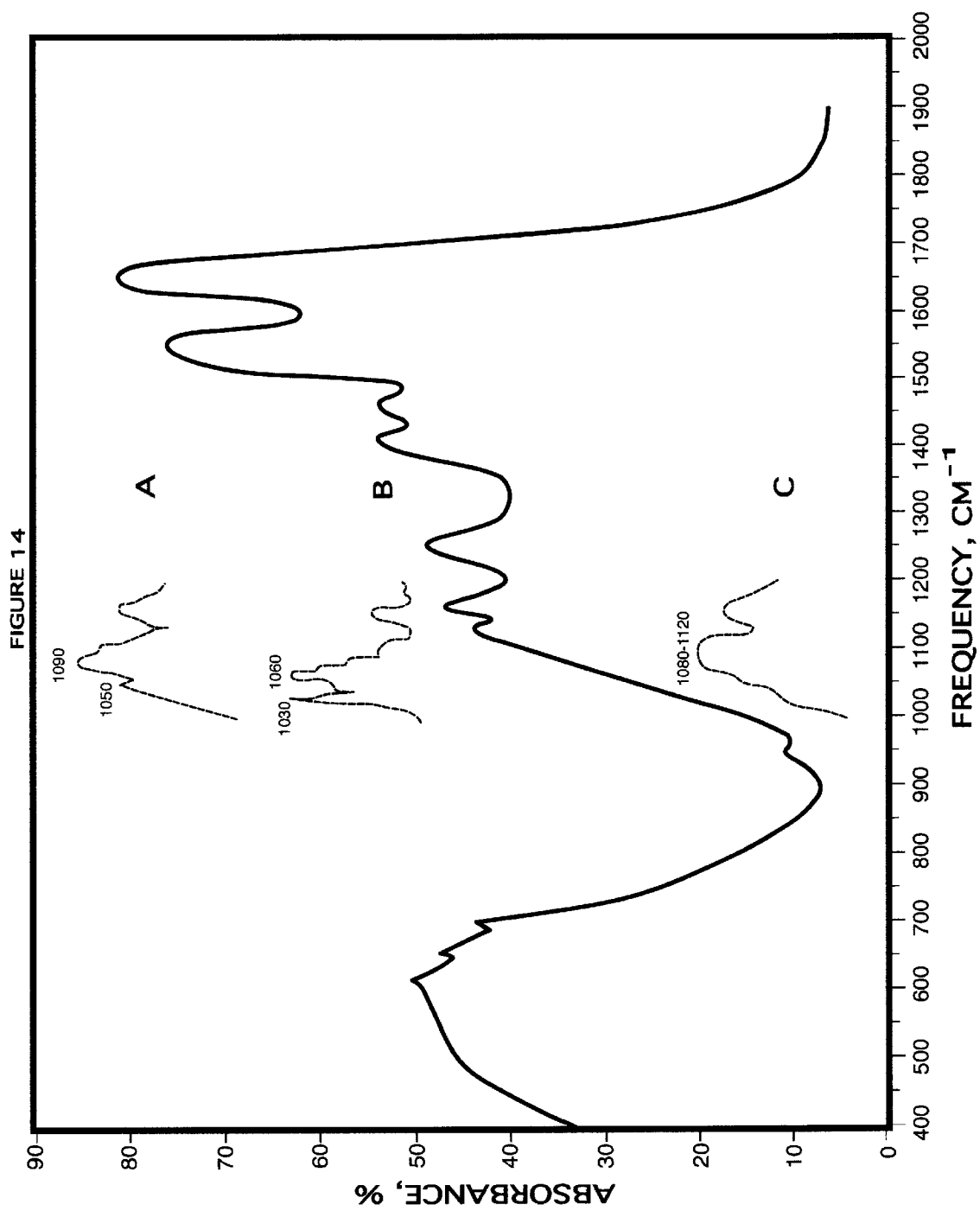
FIG. 14 is a chart illustrating the change from the normal chart (solid line) due to more disease conditions of congenital immunodeficiency, tumors with severe immunodeficiency and allergy, such as Wiscott-Aldrich syndrome, retroperitoneal lymphoma and bronchial asthma (shown in dashed lines).

In the same time one can see an "M"-like curve in the range of about 1000 cm$^{-1}$ to about 1100 cm$^{-1}$ with two peaks at the frequencies of about 1050 cm$^{-1}$ and 1080 cm$^{-1}$, reflecting severe immunodeficiency, correlated with congenital pigmented nevi (REGION 4, Subregion 4B). Reference is made also to FIGS. 11 and 14 for other endocrine and tumor disorders, correlated with immunodeficiency.

Figure 7:
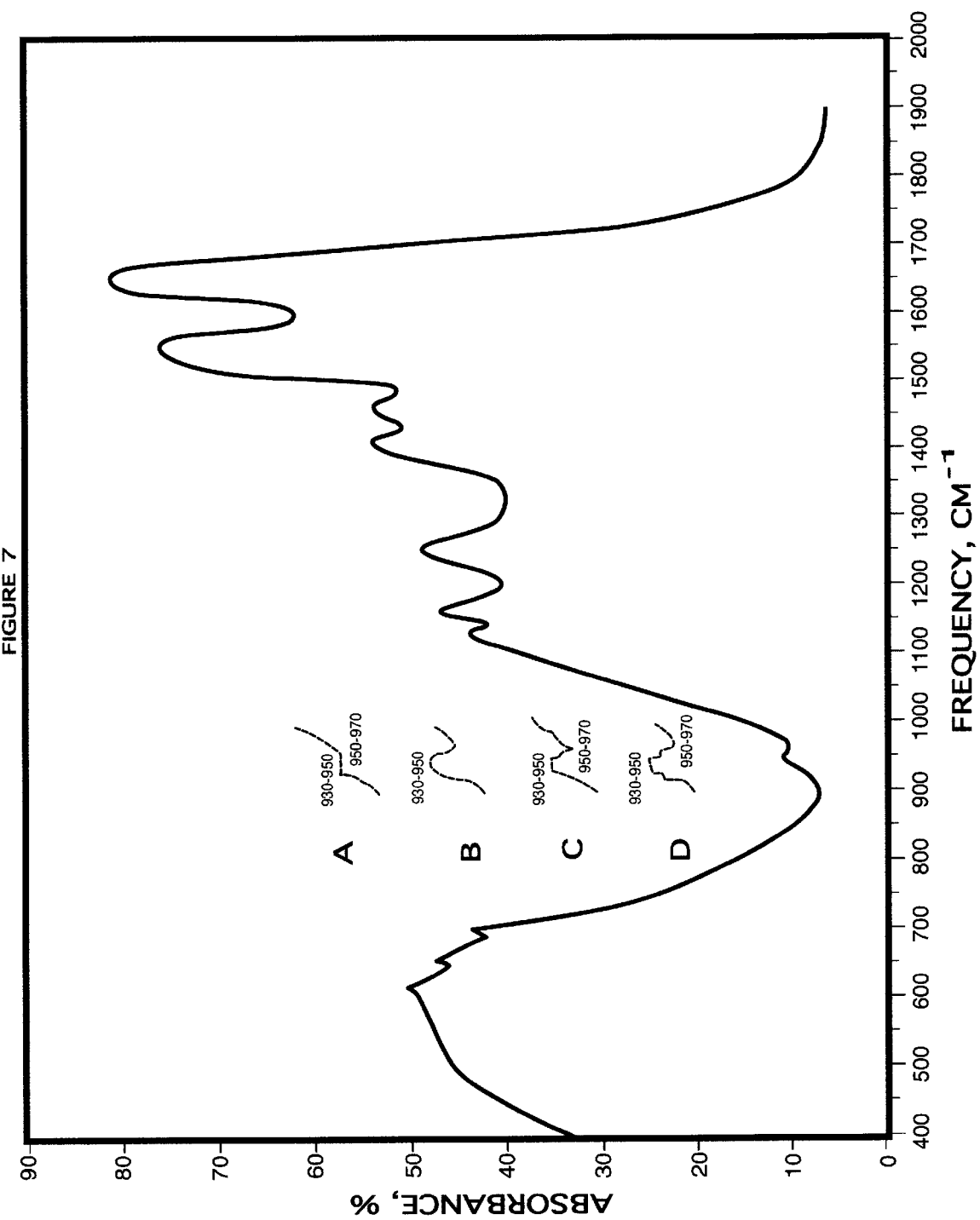
FIG. 7 is a chart illustrating the change from the normal chart (solid line) due to various pathological conditions of stomach and duodenum, such as acute and chronic gastritis and duodenitis (shown in dashed lines).

FIG. 7 illustrates the changes that may be caused in the IR absorbance spectra chart in the frequency range of about 900 cm$^{-1}$ to about 1000 cm$^{-1}$ by the disorders of stomach, pancreas, duodenum, jejunum, ileum, appendix and some types of tumor growth. This area of the chart is a small elliptical peak with a rounded top and is reflective of the compounds resulting from the normal digesting process in the gastrointestinal tract. Various pathologies damaging cells of gastrointestinal tract change that normally occurring process and add a number of additional chemical compounds, including specific protein-lipid complex from intestinal cells, reflecting in this area of the IR spectra in a number of specific ways.

More particularly, the area of the chart in the frequency range of about 930 cm$^{-1}$ to about 950 cm$^{-1}$ is normally an elliptical rounded peak and is reflective of the condition of the stomach. Any change in this area of the chart indicates disorders or diseases of the stomach.

Line A shows reduced peak with its transformation into a straight line, which is indicative of chronic hypoacidic gastritis.

On the other hand, line B shows a much higher and wider rounded peak than in the normal condition, indicating acute gastritis.

Line C illustrates a "trapezium"-like peak with a flat top indicating chronic hypertrophied gastritis, while line D having several peaks shaped steps indicates another gastritis variation called chronic atrophied gastritis.

Gastritis condition shown on lines A, C, and D are frequently associated with chronic duodenitis, which should be also suspected in these patients and can be seen in the area of about 950 cm$^{-1}$–970 cm$^{-1}$ typically as a straight line or a rounded (or sharp) negative peak.

Figure 8:
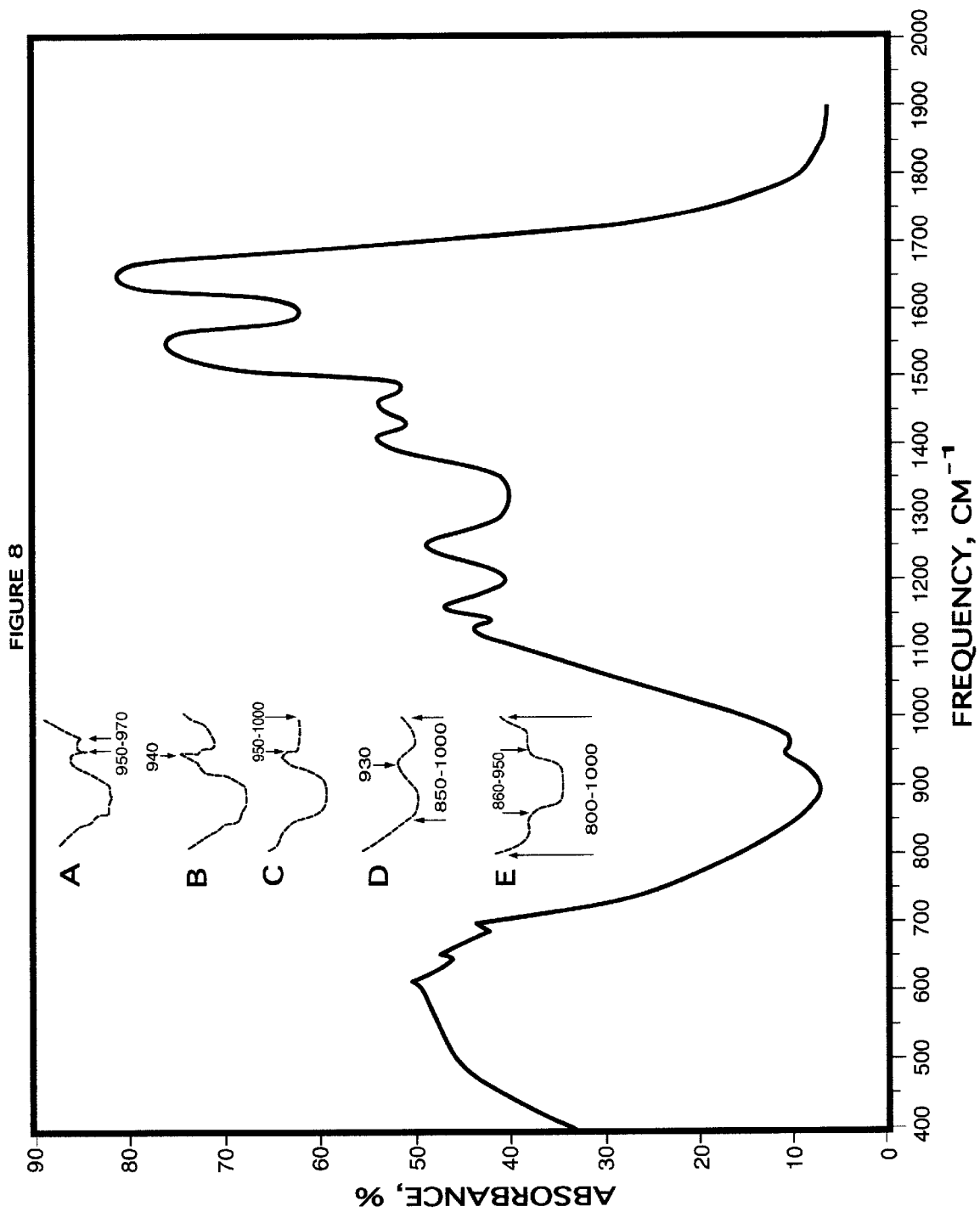
FIG. 8 is a chart illustrating the change from the normal chart (solid line) due to various pathological conditions of pancreas, duodenum, colon and ileum, such as duodenitis, pancreatitis, ileitis, insufficiency of ileocecal valve and celiac disease (shown in dashed lines).

FIG. 8 illustrates more disorders of the same group of organs that can be seen in the frequency range of about 900 cm$^{-1}$ to about 1000 cm$^{-1}$. More specifically, uprising elliptic line in the frequency range of about 970 cm$^{-1}$ to about 1000 cm$^{-1}$ is indicative of a normal condition of jejunum and ileum.

Line A contains a small rounded peak in the area of about 950 cm$^{-1}$ to 970 cm$^{-1}$ indicating acute duodenitis.

The presence of a sharp peak at a frequency of about 940 cm$^{-1}$ over the enlarged rounded peak at the frequency range of about 930 cm$^{-1}$ to about 950 cm$^{-1}$ is indicative of acute pancreatitis (line B).

Inflammation of jejunum and ileum, or enteritis with terminal ileitis (line C), is affecting the normally uprising line of the IR spectra in the range of about 970 cm$^{-1}$ to 1000 cm$^{-1}$ by reducing the rate of absorbance and flattening the line on the level of stomach condition. Reference is made also to FIGS. 9 and 10 for other small intestine disorders.

Some diseases, affecting both a small intestine and a large intestine at the same time, are shown on line D and line E.

Such illness as insufficiency of ileocecal valve can be diagnosed by significant reduction of the absorbance intensity at the frequency range of about 850 cm$^{-1}$ to about 1000 cm$^{-1}$ (line D). Also the absorbance band changes dramatically in such a way, that a small elliptical peak at the frequency of about 930 cm$^{-1}$–950 cm$^{-1}$ becomes much larger and shifts to the left to about 930 cm$^{-1}$, occupying the area of about 900 cm$^{-1}$ to about 950 cm$^{-1}$. In addition one can identify a sharp reduction in the IR absorbance in the area of about 850 cm$^{-1}$ to about 900 cm$^{-1}$ and gradual absorbance decrease at the frequency range of about 810 cm$^{-1}$ to about 850 cm$^{-1}$.

Another kind of malabsorption, shown on line E, is celiac sprue (or mucosal malabsorption, or glutein-sensitive enteropathy) the main symptom of which is osmotic diarrhea also affecting a small intestine and a colon. If such a condition is present, one can identify a powerful reduction in the absorbance intensity in the frequency range of about 800 cm$^{-1}$ to about 1000 cm$^{-1}$. Also, a significant change in shape of the absorbance band, which transforms into a "trough"-like line with a wide top in the frequency range of about 860 cm$^{-1}$ to about 950 cm$^{-1}$. Reference should be made here to other colon conditions described on FIGS. 5, 9, 10 and 12.

Appendicitis can also be diagnosed in this area of the chart. However, it should be noted that one can not see on the IR spectra chart the absorbance band correspondent to appendix. The conclusion about presence of appendicitis can be made only indirectly as a result of changes in the area of IR spectra reflecting small intestine (jejunum, ileum and stomach).

FIG. 9 shows various possible lines indicating appendicitis in the frequency range of about 910 cm$^{-1}$ to about 1000 cm$^{-1}$. Typically, normally rounded descending and uprising line in the frequency range of about 950 cm$^{-1}$ to about 980 cm$^{-1}$ becomes a combination of two straight lines forming a "V"-like line or a "step"-like line.

Line A presents a case of acute catarrhous appendicitis having a "V"-shaped line at a frequency of about 960 cm$^{-1}$. Also a small elliptical peak, reflecting stomach condition, shifts to the left from the area of frequencies ranging from about 930 cm$^{-1}$ to about 950 cm$^{-1}$ to the area of frequencies ranging from about 910 cm$^{-1}$ to about 930 cm$^{-1}$. Simultaneously it transforms into a "trapezium"-like peak with a squint cut top.

Line B illustrates a variation of acute phlegmonous appendicitis, having an ascendent "step"-like line with two steps: one—at the frequency range of about 935 cm$^{-1}$–970 cm$^{-1}$ and another—at the frequency range of about 970 cm$^{-1}$–1000 cm$^{-1}$. In addition, a small elliptical peak in the frequency range of about 930 cm$^{-1}$–950 cm$^{-1}$, reflecting stomach condition, transforms into a little peak at a frequency of about 930 cm$^{-1}$.

Line C shows a case of acute Meckel's diverticulitis having a "V"-shaped line at a frequency of about 960 cm$^{-1}$ and a small step in the range of about 960 cm$^{-1}$ to about 1000 cm$^{-1}$ 1.

For all kinds of appendicitis one can see changes in the area of about 850 cm$^{-1}$ I to about 900 cm$^{-1}$, which is typical for chronic colitis.

Clinical symptoms of appendicitis are similar to the symptoms of such conditions as paranephritis (line D) and acute mesenteric adenitis (line E). As shown on the drawings, these conditions do not have either a "V"-shaped or a "step"-shaped line and therefore are easily differentiated from appendicitis using the method of present invention, which allows avoiding unnecessary surgery. Reference is also made to FIGS. 5, 8, 10 and 12 for other small and large intestine conditions.

FIG. 10 illustrates some infectious disorders of gastrointestinal tract.

Line A presents a case of acute brucellosis with primarily gastrointestinal complications with a powerful increase in the IR absorbance in the area, ranging from about 850 cm$^{-1}$ to about 950 cm$^{-1}$, reflecting inflammation of a colon and a stomach. Then there is a decrease of absorbance intensity in the frequency range of about 950 cm$^{-1}$ to about 1000 cm$^{-1}$, reflecting inflammation of a small intestine. As a result, the shape of absorbance band in the area of about 850 cm$^{-1}$ to about 1000 cm$^{-1}$ damatically changes with transformation into a "large broken wave", reflecting a small and a large intestine lymph nodes inflammation (acute colitis and enteritis in case of brucellosis).

Line B can be useful in case of lambliasis. This condition is characterized with the presence of a peak at a frequency of about 980 cm$^{-1}$ (which is normally absent) on the same elevation as a stomach portion of the chart. Also a stomach portion of the chart makes a shift to the right into the area of about 940 cm$^{-1}$–960 cm$^{-1}$ followed by a decrease of absorbance intensity in the area of about 960 cm$^{-1}$–1000 cm$^{-1}$. In addition, it should be noted that a reduction in the IR absorbance in the area of about 850 cm$^{-1}$–900 cm$^{-1}$ transforms rounded elliptic angle at a frequency of about 900 cm$^{-1}$ into more sharp angle.

Line C illustrates a case of enterobiasis with a sharp peak at a frequency of about 980 cm$^{-1}$. This peak is higher than stomach portion of the chart, which also makes a shift to the right in the frequency range of about 940 cm$^{-1}$–960 cm$^{-1}$ and transforms into a "trapezium"-like line. Also, there is a reduction in the IR absorbance in the area of about 850 cm$^{-1}$ to about 900 cm$^{-1}$ with a simultaneous turn into the opposite side.

FIG. 11 shows the chart typical of malignant tumor, such as retroperitoneal lymphoma, occupying the area ranging from about 800 cm$^{-1}$ to about 1100 cm$^{-1}$.

This is a genetically determined tumor with very severe immunodefficiency. First of all it is characterized by the presence of a large peak at a frequency of about 908 cm$^{-1}$ with a wide base, ranging from about 880 cm$^{-1}$ to about 930 cm$^{-1}$. This peak is indicative of a malignant tumor and also is reflective of tumor influence on endocrine system (REGION 3, Subregion 3A and 3B).

Since this disease is affecting other organs, the changes can be seen in other areas of REGION 3 and also in other REGIONS.

For example the lack of a small elliptical peak at a frequency of about 930 cm$^{-1}$–950 cm$^{-1}$ reflects tumor influence on the stomach condition (Subregion 3B).

A powerful increase in the IR absorbance in the frequency range of about 840 cm$^{-1}$–880 cm$^{-1}$ with formation of an elongated "rectangular"-like peak at a frequency of about 850 cm$^{-1}$–860 cm$^{-1}$ reflects tumor influence on kidney (Subregion 3A).

Also a "terrace"-like descendent line in the area ranging from about 860 cm$^{-1}$ to about 880 cm$^{-1}$ reflects tumor affect on colon (Subregion 3A).

Since retroperitoneal lymphoma is also affecting the immune system, one can identify "M"-like curve in the area ranging from about 1000 cm$^{-1}$ to about 1100 cm$^{-1}$ with the peaks at frequencies of about 1030 cm$^{-1}$ and 1060 cm$^{-1}$, reflecting very severe immunodeficiency condition (REGION 4, Subregion B). Reference is also made to FIG. 6 (Line D) and FIG. 14 (Line A) for other tumors with endocrine disorders, correlated with immunodeficiency.

Figure 12:
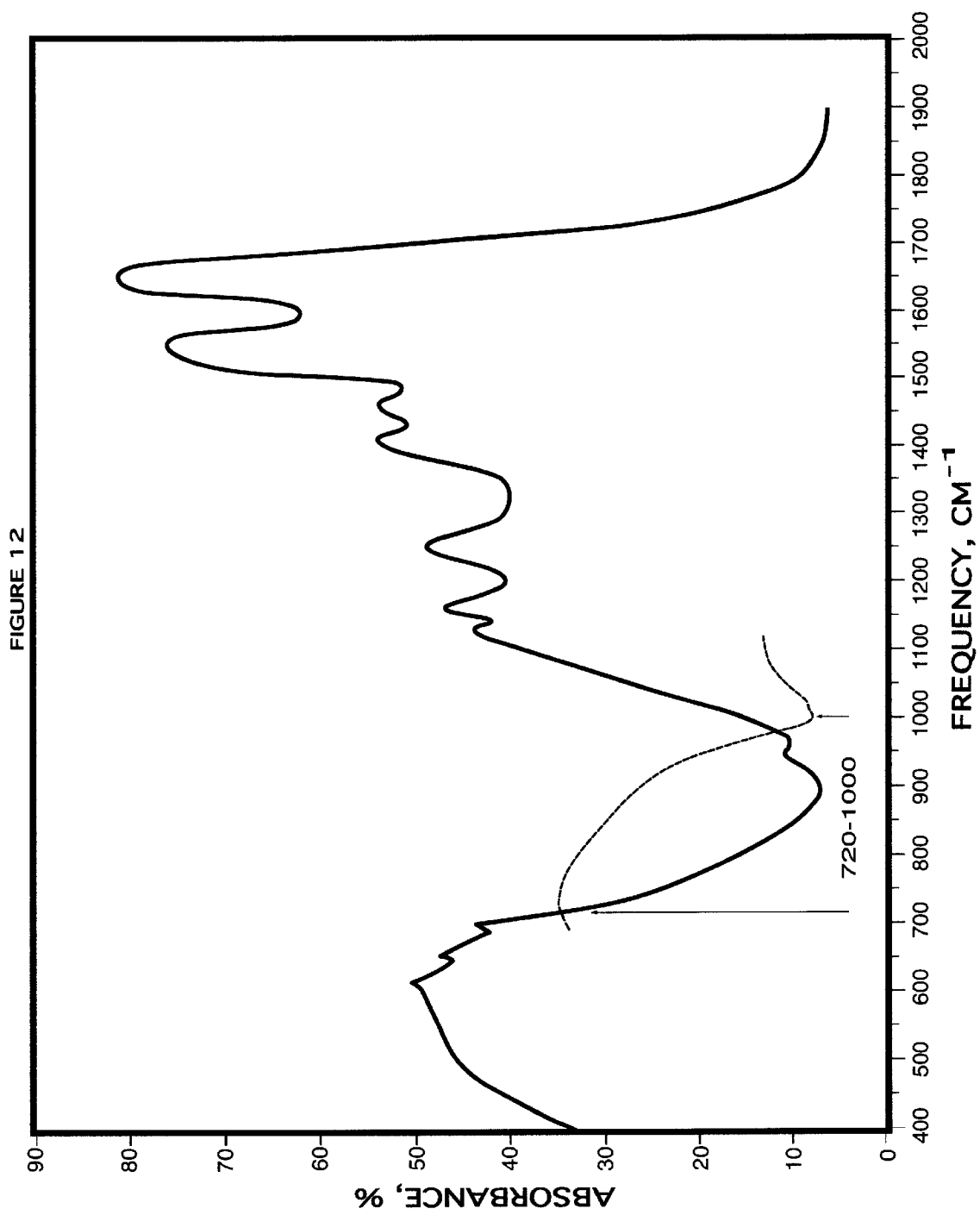
FIG. 12 is a chart illustrating the change from the normal chart (solid line) due to various other congenital diseases of colon such as dolichocolon (shown in dashed lines).

FIG. 12 illustrates a congenital colon disorder of dolichocolon (or elongated colon) in the range of about 720 cm$^{-1}$ to about 1000 cm$^{-1}$. Here one can see a sharp increase in the IR absorbance with a shift to the right and turn into the opposite side, fully covering the area ranging from about 720 cm$^{-1}$ to about 1000 cm$^{-1}$.

Region 4: Frequency of 1000 cm$^{-1}$ to 1140 cm$^{-1}$

This region is mostly indicative of a liver and immune system condition in norm and in pathology. Also this region may be helpful for diagnostics of sepsis (nonspecific phagocyte immunodeficiency) as it had been shown in our Patent # SU 1,698,775.

The peak at a frequency of about 1130 cm$^{-1}$ is indicative of normal liver function and the lack of this presence is indicative of liver disorders (FIG. 1).

Figure 13:
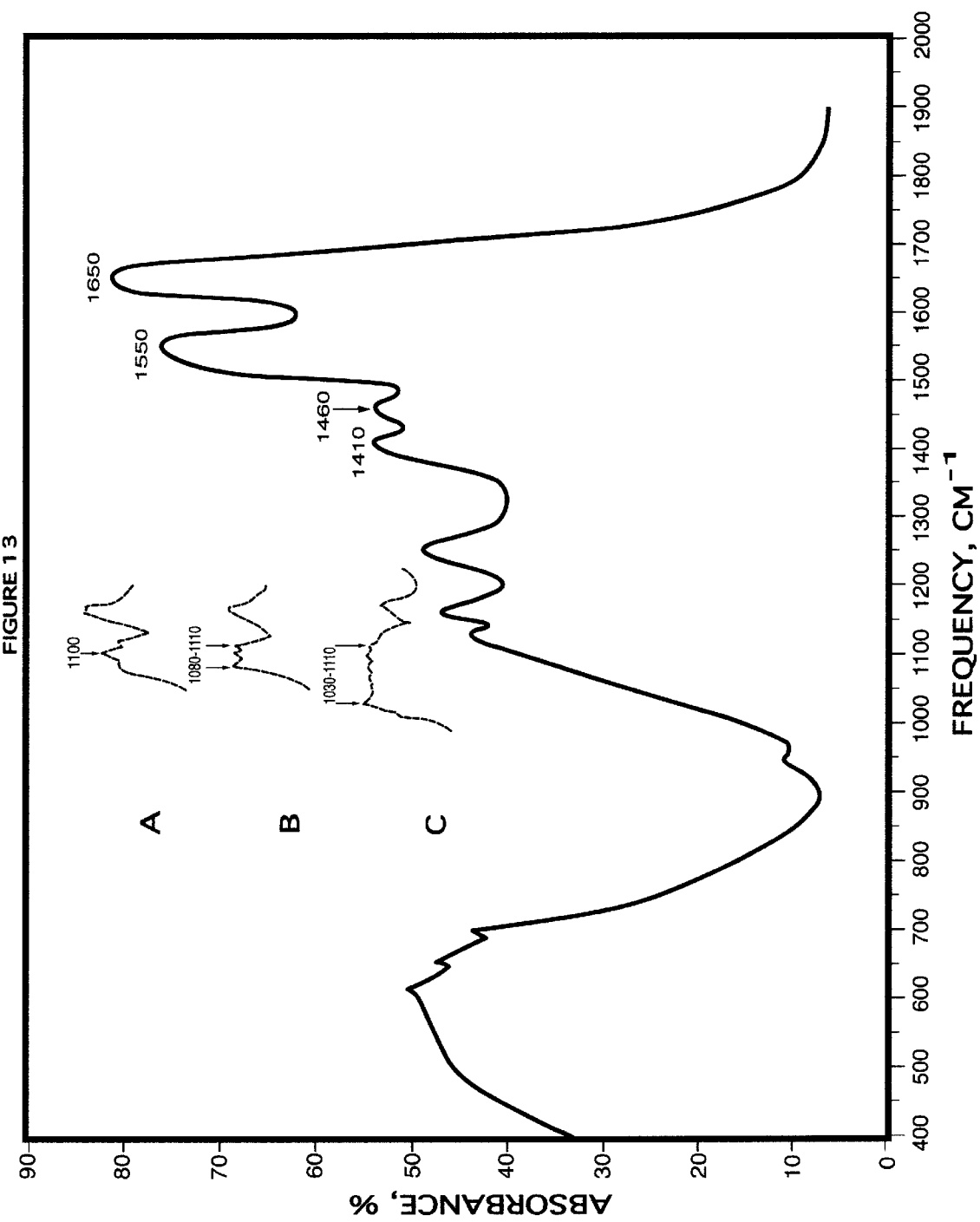
FIG. 13 is a chart illustrating the change from the normal chart (solid line) due to various pathologic conditions of gallbladder and liver, such as acute and chronic cholecystitis with cholangiohepatitis and acute viral hepatitis B (shown in dashed lines).

FIG. 13 represents changes in the normal IR spectra of blood caused by various disorders of liver and gallbladder.

Line A illustrates a typical case of acute cholecystitis, where there is a sharp small peak at a frequency of about 1100 cm$^{-1}$ with the simultaneous lack of a normal peak at a frequency of about 1130 cm$^{-1}$.

Line B represents the condition of chronic cholecystitis with cholangiohepatitis, in which one can identify a large "saw"-shaped band of absorption in the range of about 1080 cm$^{-1}$ to about 1110 cm$^{-1}$. Whereat, a normal peak at a frequency of about 1130 cm$^{-1}$ is not present. These changes are typical for any type of chronic hepatitis regardless of its etiology, such as for example, inflammation caused by microbes, viruses, toxins, metabolic disorders, etc.

Finally, line C is indicative of a condition of acute viral hepatitis. Whereat one can identify a significant increase in the IR absorbance in the range of about 1030 cm$^{-1}$ to about 1110 cm$^{-1}$ in shape of a long broken and almost horizontal line, covering this whole range of IR spectra. Also there is the lack of a peak at a frequency of about 1130 cm$^{-1}$ normally clearly visible and indicative of a normal liver function.

FIG. 14 shows a condition of Wiskott-Aldrich syndrome (line A), having a large rounded peak with a wide base at a frequency of about 1090 cm$^{-1}$ and a small peak at a frequency of about 1050 cm$^{-1}$. The immunodeficiency in these patients is associated with low levels of IgM. These patients form the antibodies poorly to certain antigens, especially to polysaccharide and small protein antigens, and show a progressive deficiency of T-cell numbers and function. They frequently succumb to infection from any of the various bacteria, viruses and fungi. Nearly 10% of these patients eventually die of cancer.

Line B represents a manifestation of very severe immunodeficiency in a patient with malignant tumor such as retroperitoneal lymphoma (see also FIG. 11). As one can identify, there is a more pronounced shift of the absorbance band into the area of low frequencies with an appearance of two prominence sharp peaks. These peaks at frequencies of about 1030 cm$^{-1}$ and 1060 cm$^{-1}$ form an "M"-shaped line (compare with line A, where the level of immunodeficiency is less than was shown on line B and peaks at frequencies of about 1050 cm$^{-1}$ and 1090 cm$^{-1}$ have a different shape).

Reference is made also to FIG. 6, line D, which shows the case of severe immunodeficiency with other kind of tumor, such as congenital pigmented nevi.

Line C is indicative of a variety of lung allergy conditions causing respiratory allergies, allergic bronchitis, or asthma, having a pronounced wide peak in the range of about 1080 cm$^{-1}$ to about 1120 cm$^{-1}$, which is higher than a peak at a frequency of about 1160 cm$^{-1}$, which is contrary to the norm.

Region 5: Frequency of 1140 CM$^{-1}$ to 1350 CM$^{31\ 1}$

FIGS. 15 through 20 illustrate various cardiac disorders and cover the range of about 1160 cm$^{-1}$ to about 1350 cm$^{-1}$. More specifically this area can be divided into three Subregions:

Subregion 5A: a peak at a frequency of about 1160 cm$^{-1}$ is indicative of a normal condition of myocardial muscle (FIG. 1);

Subregion 5B: the straight descendent under acute angle line in the range of about 1180 cm$^{-1}$ to about 1200 cm$^{-1}$ is reflective of a normal condition of the heart valves and/or the absence of the heart insufficiency (FIG. 1);

Subregion 5C: the area ranging from about 1200 cm$^{-1}$ to about 1350 cm$^{-1}$ with a peak at a frequency of about 1250 cm$^{-1}$ is indicative of a normal condition of the cardiac rhythm (FIG. 1).

Changes in the area of frequencies of about 1160 cm$^{-1}$ to about 1350 cm$^{-1}$ is indicative of the appropriate pathologies of myocardial muscle, disorders of the heart valves and/or presence of the heart insufficiency, and cardiac arrhythmia.

Figure 15:
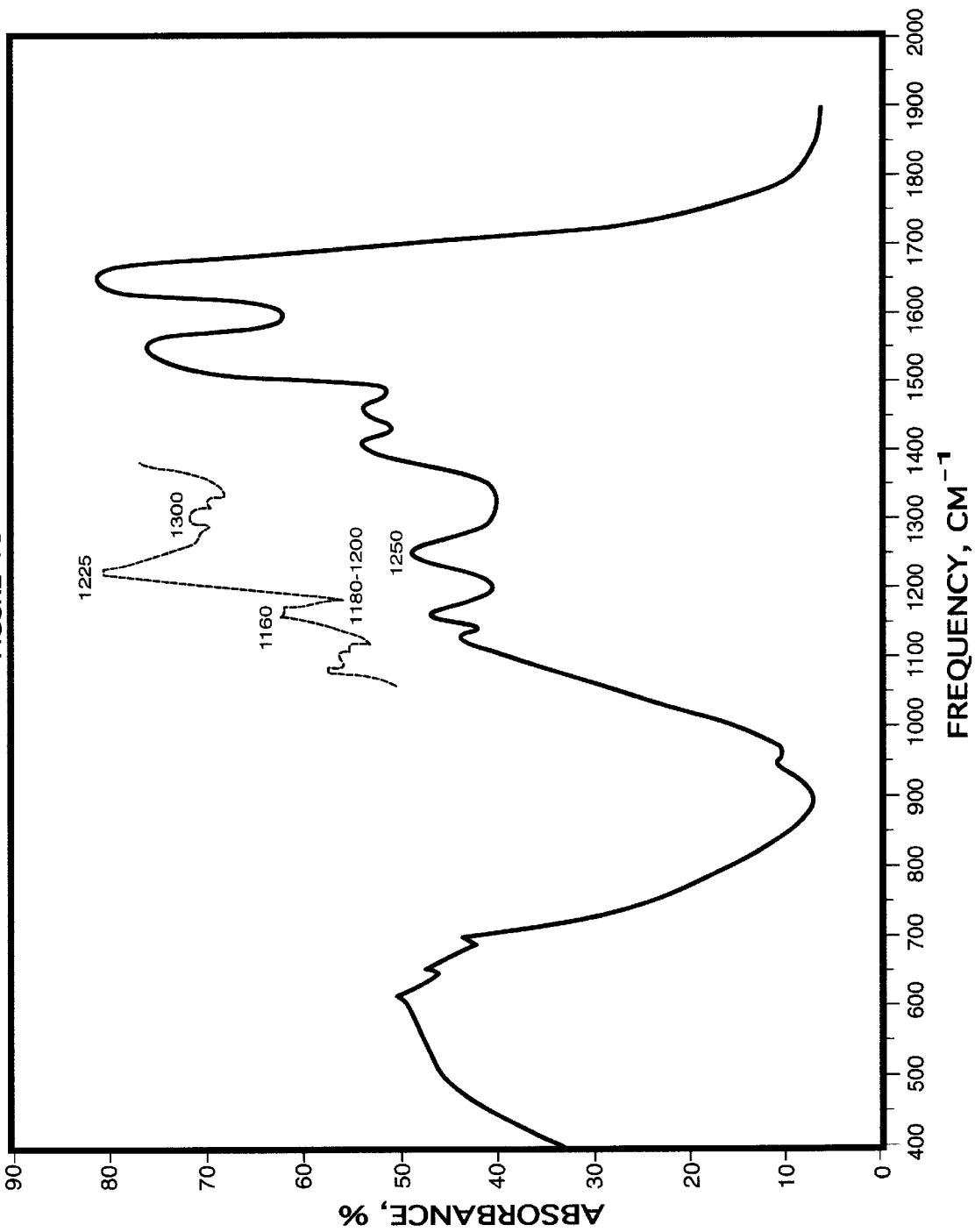
FIG. 15 is a chart illustrating the change from the normal chart (solid line) due to various cardiac conditions, such as acute myocarditis (shown in dashed lines).

FIG. 15 shows an example of such condition as acute toxic myocarditis in diabetic patients.

As one can identify there is a pronounced peak at a frequency of about 1160 cm$^{-1}$, having an elongated "trapezium"-shaped line with a cut top (reflecting an inflammation of myocardial muscle).

Then, one should note a sharp increase in the IR absorbance in the frequency range of about 1180 cm$^{-1}$ to about 1200 cm$^{-1}$ (reflecting the functional cardiac insufficiency).

Also, there is an increase in the IR absorbance of the peak at a frequency of about 1250 cm$^{-1}$ with a shift to the left to about 1225 cm$^{-1}$. In addition a new rounded small peak at a frequency of about 1300 cm$^{-1}$ is appearing, which is normally absent (these changes reflects the cardiac arrhythmia).

Figure 16:
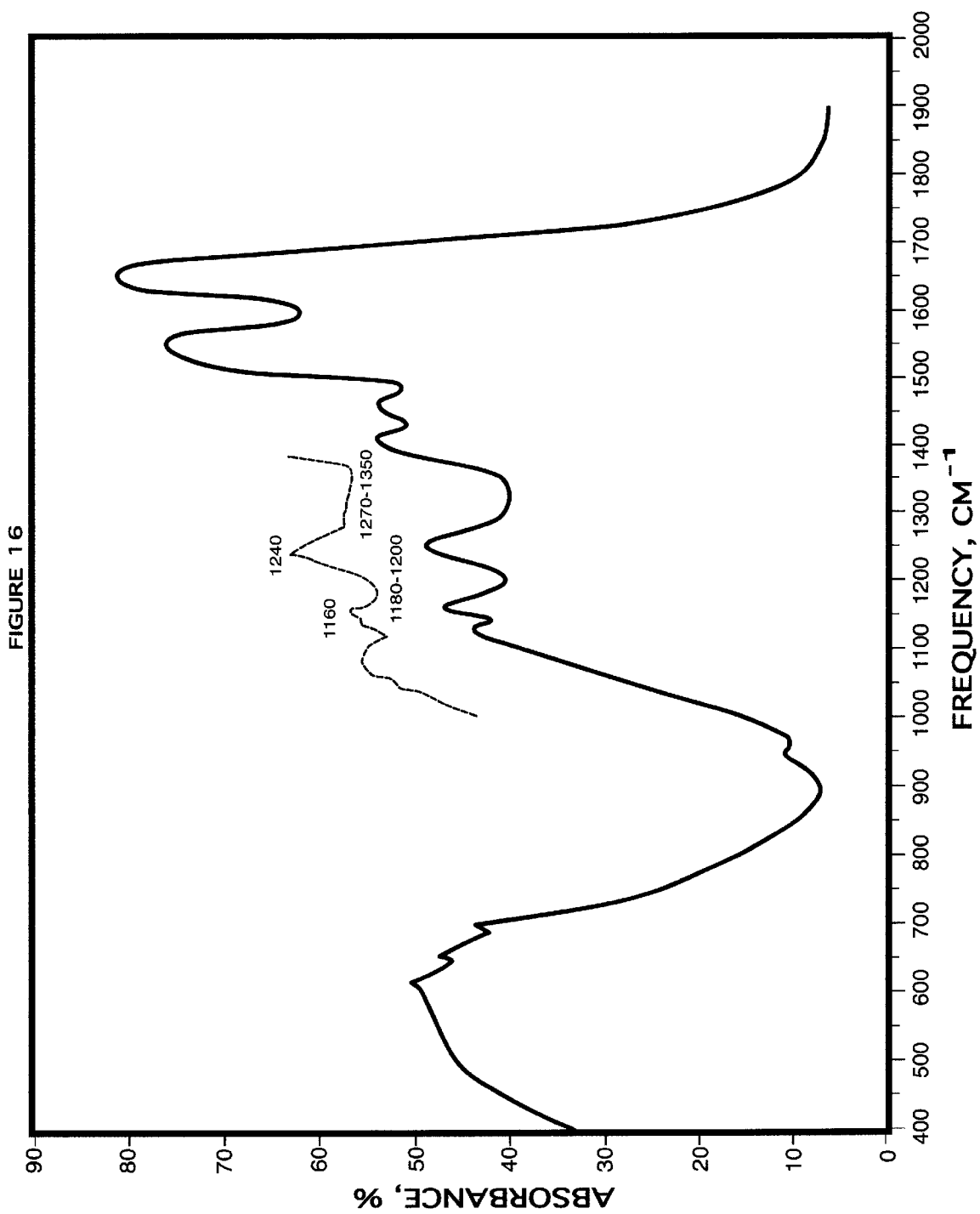
FIG. 16 is a chart illustrating the change from the normal chart (solid line) due to various other heart conditions, such as cardiomyopathy with heart rhythm disorders, ventricular hypertrophy and cardiosclerosis (shown in dashed lines).

FIG. 16 contains a dashed line indicative of various pathologic changes in a myocardium, such as cardiomyopathy (in patient with hypertension, ventricular hypertrophy, and coronary artery disease).

In that case, one can identify a reduction in the IR absorbance at a frequency of about 1160 cm$^{-1}$. Whereat, a shape of this peak changes dramatically in such a way that it becomes widened and flattened, occupying the area ranging from about 1140 cm$^{-1}$ to about 1160 cm$^{-1}$ with a split on the top at a frequency of about 1150 cm$^{-1}$ (metabolic changes in myocardial muscle).

Also, there is a small increase in the IR absorbance in the range of about 1180 cm$^{-1}$ to about 1200 cm$^{-1}$ (functional cardiac insufficiency).

Finally, one can see a decrease in the IR absorbance in the area of the peak at a frequency of about 1250 cm$^{-1}$ with a shift to the left to about 1240 cm$^{-1}$. And also an increase in the IR absorbance in the shape of a wide flat line in the frequency range of about 1270 cm$^{-1}$ to about 1350 cm$^{-1}$ (cardiac arrhythmia).

Figure 17:
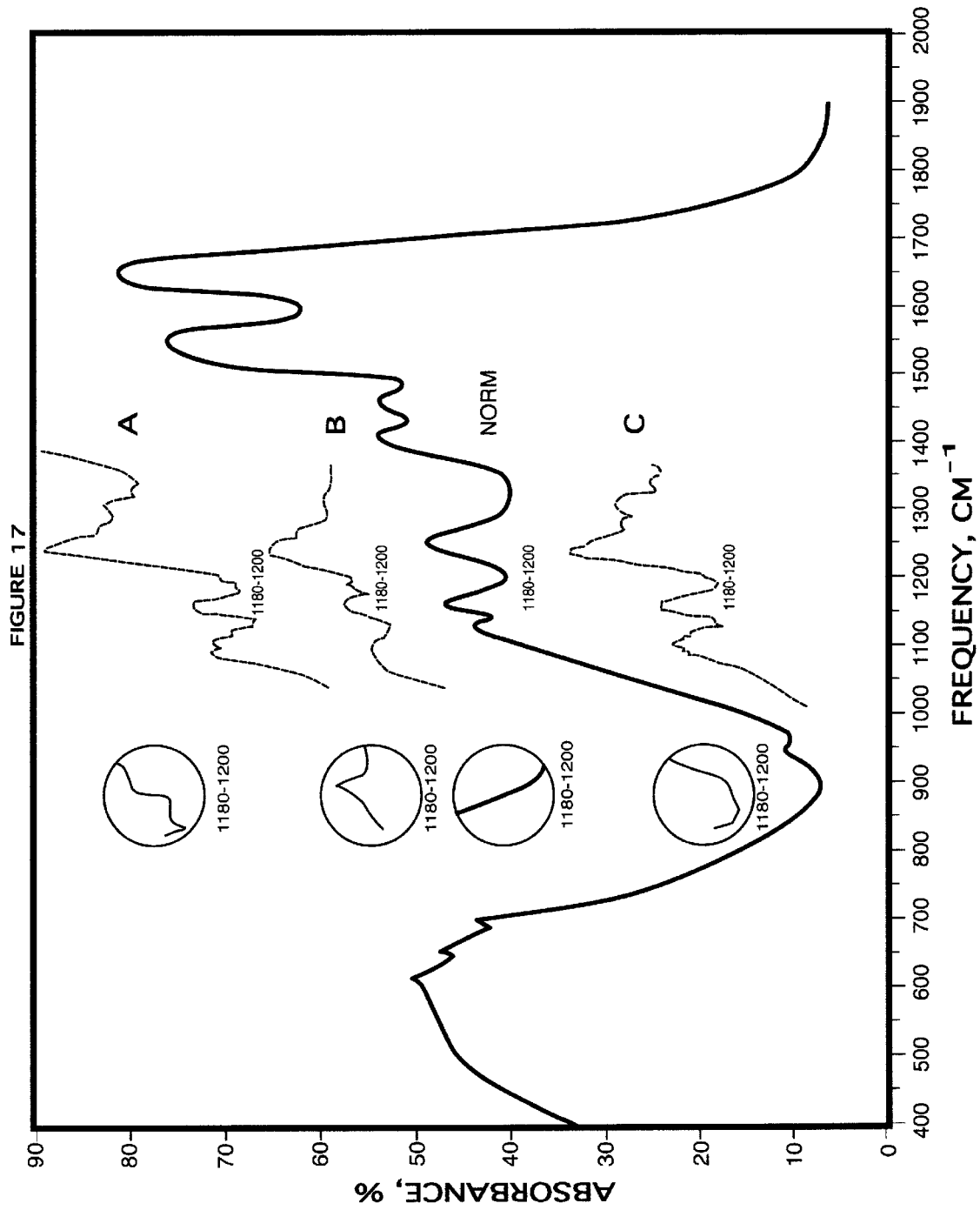
FIG. 17 is a chart illustrating the change from the normal chart (solid line) due to various pathologic conditions of heart and heart valves (shown in dashed lines), such as congenital atrial or ventricular septal defect, rheumatic mitral regurgitation and prolapse of mitral valve.

FIG. 17 illustrates further pathologic conditions of the heart.

Line A is indicative of congenital atrial and ventricular septal defect. Whereat, one can see an increase in the IR absorbance in the range of about 1180 cm$^{-1}$–1200 cm$^{-1}$. The absorbance band has the shape of an ascendent "step"-like line with two small steps. The first step, at the frequency ranging from about 1180 cm$^{-1}$ to about 1189 cm$^{-1}$, and the second high slighting step at the frequency ranging from about 1190 cm$^{-1}$ to about 1200 cm$^{-1}$ (organic cardiac insufficiency).

At the same time, the peak at the frequency of about 1160 cm$^{-1}$ shifts to the left to about 1150 cm$^{-1}$ (metabolic changes in myocardial muscle).

Line B represents rheumatic mitral regurgitation having a powerful increase in the IR absorbance in the frequency range of about 1180 cm$^{-1}$ to about 1200 cm$^{-1}$. This line is in the shape of a crown (mitra) with a little peak at a frequency of about 1192 cm$^{-1}$ (organic heart failure).

Whereat, the peak at a frequency of about 1160 cm$^{-1}$ transforms into an elliptical rounded peak at a frequency ranging from about 1150 cm$^{-1}$ to about 1170 cm$^{-1}$, which is much smaller than in normal condition (metabolic changes in myocardial muscle).

Line C shows a condition of mitral valve prolapse with a very small increase in the IR absorbance ranging from about 1180 cm$^{-1}$ to about 1200 cm$^{-1}$. The line is in the shape of a turned-over crown (turned-over mitra).

At the left, the detailed focus of the corresponding lines A, B, C is shown, which represents the range of about 1180 cm$^{-1}$ to about 1200 cm$^{-1}$, including the norm.

All three lines have non-specific changes in the area ranging from about 1200 cm$^{-1}$ to about 1350 cm$^{-1}$, corresponding to different types of arrhythmia.

Figure 18:
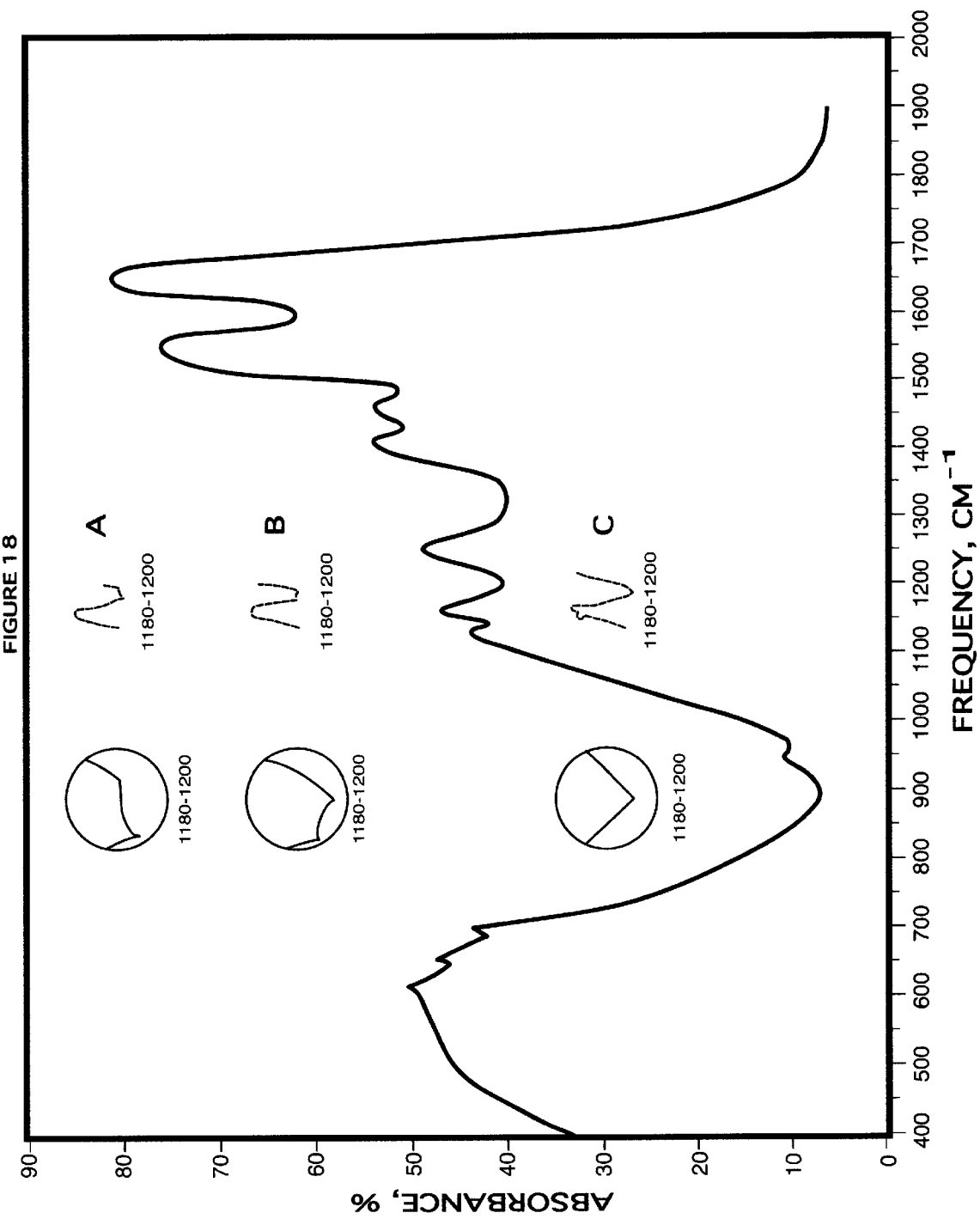
FIG. 18 is a chart illustrating the change from the normal chart (solid line) due to various other pathologic conditions of heart and heart valves, such as other kinds of prolapse of mitral valve, functional murmur and aortal stenosis.

FIG. 18 shows still further pathologic conditions of the heart valves.

Line A is indicative of another type of mitral valve prolapse with a very small increase in the IR absorbance in the frequency range of about 1181 cm$^{-1}$ to about 1188 cm$^{-1}$ coupled with almost horizontal line in the range of about 1188 cm$^{-1}$–1195 cm$^{-1}$.

Line B shows functional murmur with a very little increase in the IR absorbance in the frequency range of about 1180 cm$^{-1}$–1190 cm$^{-1}$, forming a shape of a semi-moon clipping.

Line C is indicative of aortic stenosis with an increase in the IR absorbance, ranging from about 1180 cm$^{-1}$ to about 1190 cm$^{-1}$ and from about 1190 cm$^{-1}$ to about 1200 cm$^{-1}$. Whereat, the shape of the line in this area converts into a turned-over equilateral triangle (organic heart insufficiency).

Also there is an increase in the IR absorbance in the area of about 1160 cm$^{-1}$ with transformation of a normal peak at a frequency of about 1160 cm$^{-1}$ into an elongated peak with a split top, resembling "a head of femur" (metabolic changes in myocardial muscle).

At the left, the detailed focus of the corresponding lines A, B, C is shown, which is representative for the frequency range from about 1180 cm$^{-1}$ to about 1200 cm$^{-1}$.

Figure 19:
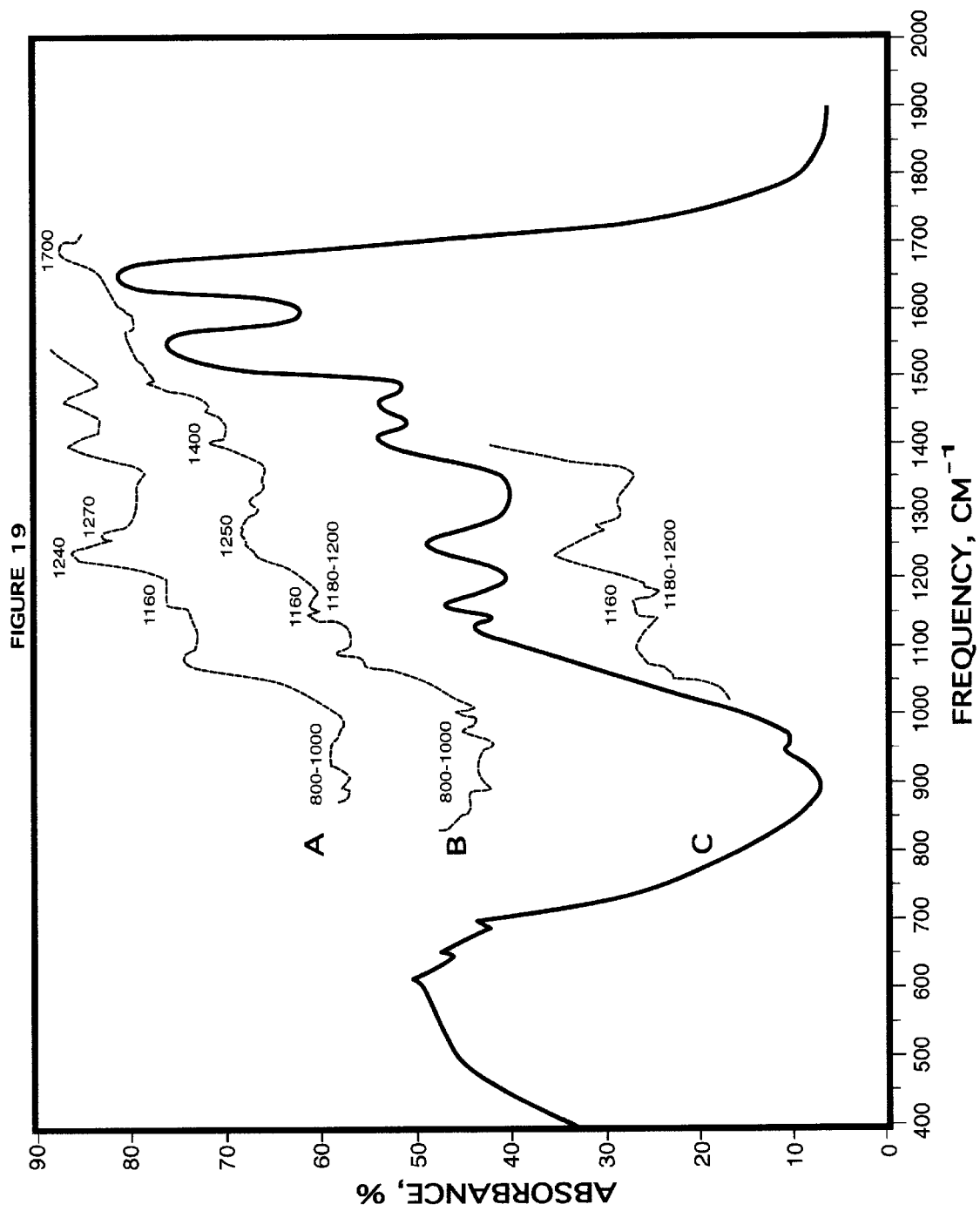
FIG. 19 is a chart illustrating the change from the normal chart (solid line) due to various further conditions of the heart, such as myocardial infarction and myocardial ischemia (shown in dashed lines).

FIG. 19 contains charts for myocardial infarction and myocardial ischemia.

Line A represents a typical case of myocardial infarction. In this case, one can see an abrupt reduction of the IR absorbance in the area of a frequency of about 1160 cm$^{-1}$ up until a complete disappearance of a peak in this area, which is normally present there. In addition, instead of a normal peak in this area, one can see a horizontal line at the frequency range of about 1160 cm$^{-1}$ to about 1200 cm$^{-1}$, reflecting severe disorders of a myocardial muscle.

Also, a peak at a frequency of about 1250 cm$^{-1}$ shifts to the left and splits into two peaks: the first peak at a frequency of about 1240 cm$^{-1}$ and the second at a frequency of about 1270 cm$^{-1}$, which typically reflects disorders of the heart conductive system. Sometimes, even three peaks are present in this area.

In addition there are the changes in the area of about 800 cm$^{-1}$–1000 cm$^{-1}$, reflecting disorders of gastrointestinal tract as a result of influence of myocardial infarction (REGION 3).

Line B shows another case of myocardial infarction with very severe damage of heart conductive system. In that situation once again one can recognize an abrupt reduction in the IR absorbance in the area of frequency of about 1160 cm$^{-1}$ and a possible appearance of two smaller peaks at about 1150 cm$^{-1}$ and 1160 cm$^{-1}$.

Also, there is an abrupt reduction of IR absorbance in the area of about 1250 cm$^{-1}$ up until a complete disappearance of a peak in this area, which is normally present (very severe damage of heart conductive system).

In addition, there are dramatic changes in the frequency range of about 800 cm$^{-1}$–1000 cm$^{-1}$ (REGION 3) and in the area of about 1400 cm$^{-1}$–1700 cm$^{-1}$ (REGION 7), reflecting corresponding severe disorders of the gastrointestinal tract and the brain as a result of myocardial infarction.

Finally, line C may be useful in diagnosis of myocardial ischemia, characterized by coronary artery disease with unstable angina in a patient with chronic pyelonephritis and diabetes mellitus.

In this case a peak at a frequency of about 1160 cm$^{-1}$ transforms into a wide "trapezium"-like line in the area ranging from about 1160 cm$^{-1}$ to about 1180 cm$^{-1}$, which is smaller and more rounded than in a normal condition (metabolic changes in myocardial muscle).

Also a sharp increase of IR absorbance is present in the area of about 1180 cm$^{-1}$–1200 cm$^{-1}$. Whereat, the absorbance band transforms into a "high step"-line at a frequency of about 1190 cm$^{-1}$ among other features (acute coronary-heart failure).

It is noteworthy that this patient developed myocardial infarction in 6 months later.

Figure 20:
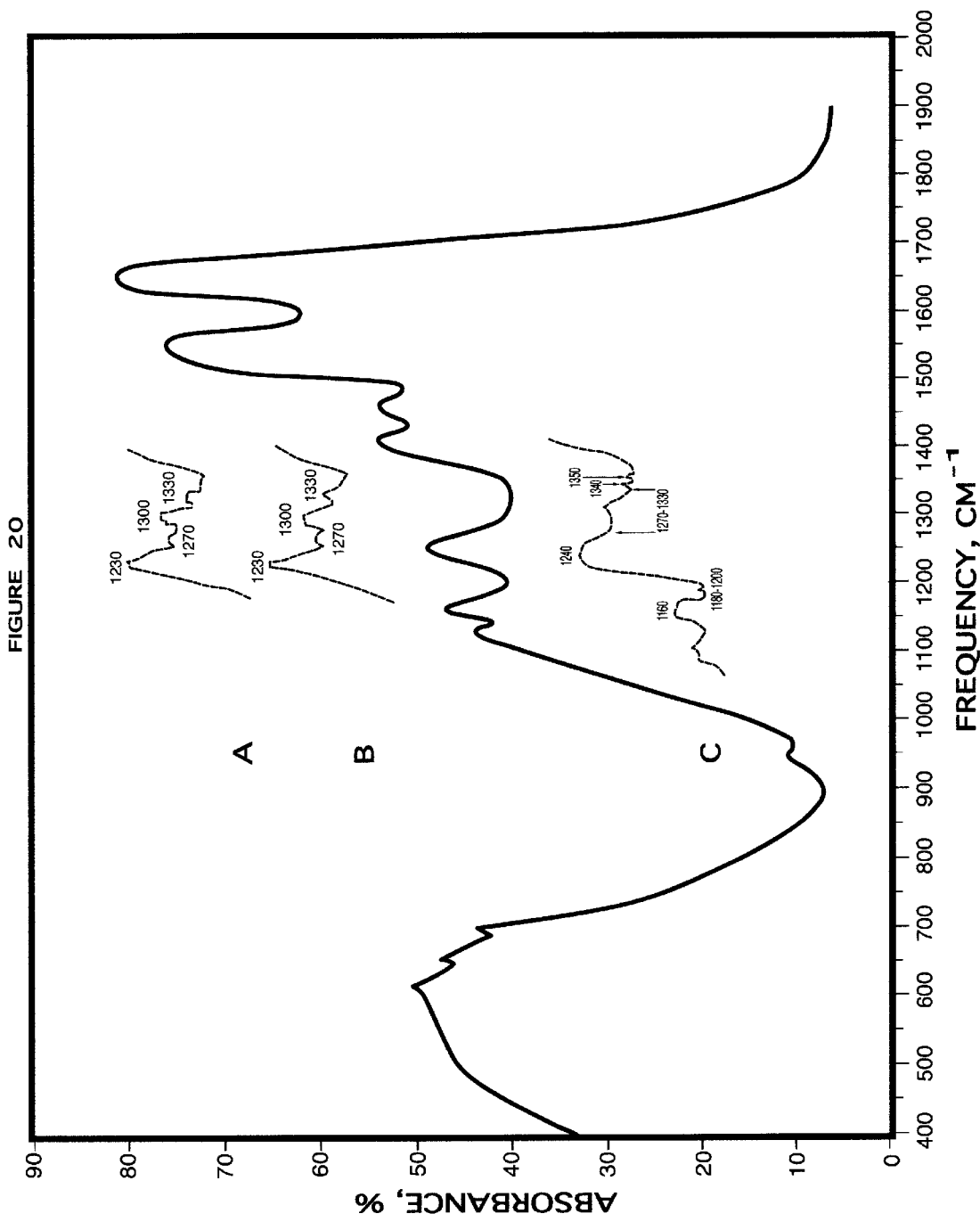
FIG. 20 is a chart illustrating the change from the normal chart (solid line) due to various pathologic heart rhythm disorders, such as bradicardia, tachicardia and Wolf-Parkinson-White syndrome (shown in dashed lines).

Other heart conditions also can be diagnosed in this area of the IR absorbance spectra, such as various rhythm disorders (arrhythmia) illustrated on FIG. 20.

Line A presents a typical case of severe bradicardia with a reduction of the IR absorbance in the area of a peak at a frequency of about 1250 cm$^{-1}$ with a shift to the left to about 1230 cm$^{-1}$. Also, one can see an appearance of three new peaks at the frequencies of about 1270 cm$^{-1}$, 1300 cm$^{-1}$ and 1330 cm$^{-1}$. A peak at a frequency of about 1330 cm$^{-1}$ has a shape of a rectangle and in the most cases of bradicardia it is absent.

Line B is indicative of severe tachycardia. In this situation one can identify the same changes like in the case of severe bradicardia, but in addition a peak at a frequency of about 1330 cm$^{-1}$ is usually present and has a "triangle"-like shape.

Finally, line C illustrates the case of Wolff-Parkinson-White syndrome, which is characterized by both ventricular preexitation and paroxysmal tachycardia. As it is well known, in the base of this pathologic condition lies atrio-ventricular (AV) bypass tracts that conduct in an antegrade direction. On a typical ECG pattern one can see a short PR interval (<0.12 s), a slurred upstroke of the QRS complex (delta wave), and a wide QRS complex. This pattern results from a fusion of activation of the ventricles over both the bypass tract and the AV nodal His-Purkinje system.

As one can see, there are unique corresponding changes with a powerful reduction in the IR absorbance in the area of a peak at a frequency of about 1250 cm$^{-1}$ with transformation into a "trapezium"-like line with rounded top band a shift to the left to about 1240 cm$^{-1}$.

Also, an increase in the IR absorbance in the range of about 1270 cm$^{-1}$–1330 cm$^{-1}$ with conversion of absorbance band into horizontal line instead normally presented descendent elliptical line. In addition one can see an appearance of two small peaks at the frequencies of about 1340 cm$^{-1}$ and 1350 cm$^{-1}$, which are not present in the chart in norm (paroxysmal tachycardia).

Whereat, there are changes in the area of Subregion 5A and 5B, reflecting metabolic changes in myocardial muscle and kind of heart insufficiency, which is characterized of this disease.

Region 6 (Mixed): Frequency of 1100 CM$^{-1}$ to 1200 CM$^{-1}$

The MIXED REGION 6 consists of Subregion 4A (which is indicative of a normal liver function) and Subregion 5A (which is indicative of a normal myocardial function of a heart). One can make conclusion about functional state of the upper respiratory tract and lungs only in case of simultaneous deviations of absorbance band in the range of about 1100 cm$^{-1}$ to about 1200 cm$^{-1}$, especially the peaks at frequencies of about 1130 cm$^{-1}$ and 1160 cm$^{-1}$, corresponding to a liver (in norm) and a heart (a myocardial muscle in norm). In this case one can make conclusion about respiratory tract and lungs condition indirectly.

Figure 21:
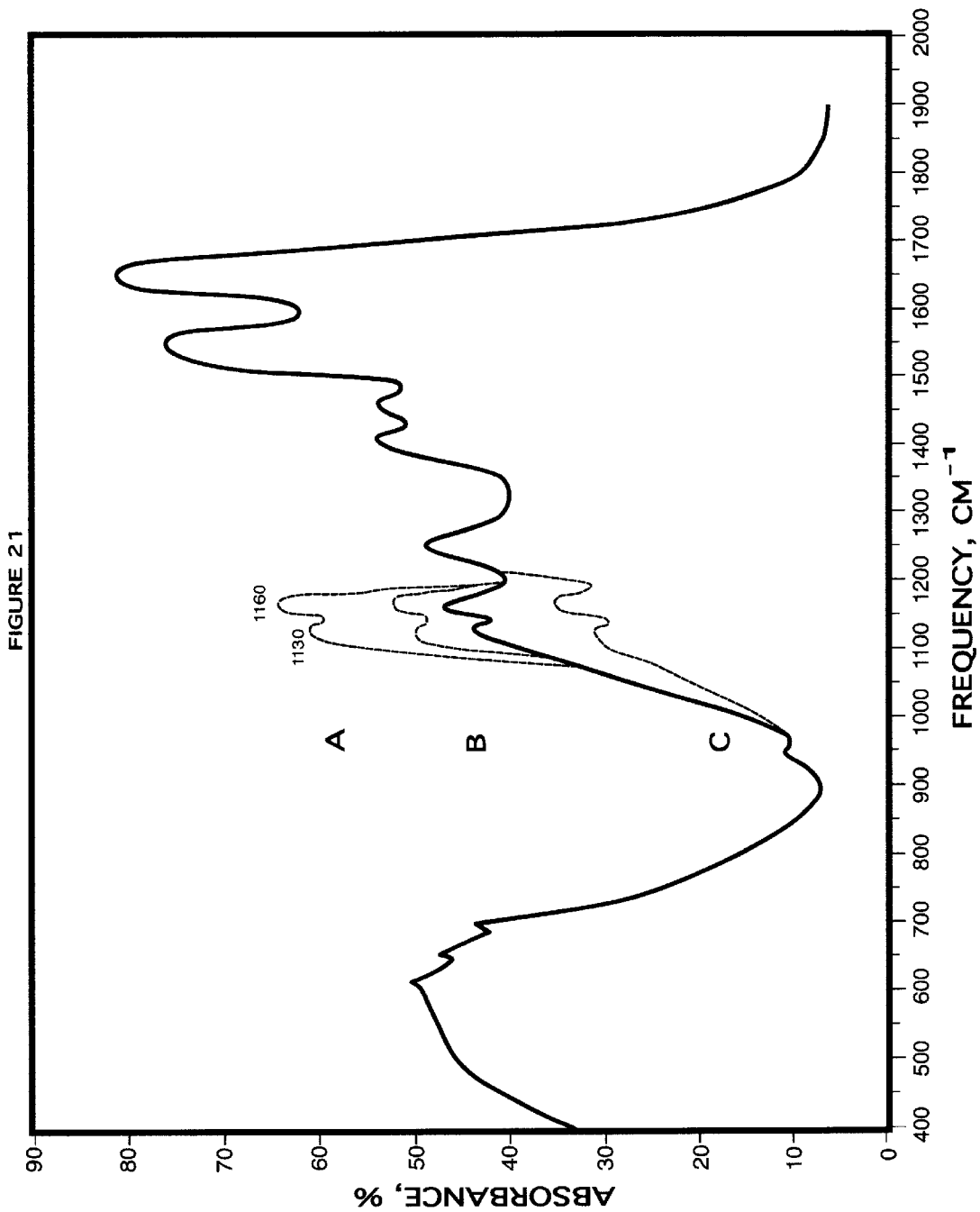
FIG. 21 is a chart illustrating the change from the normal chart (solid line) due to various other disease conditions of lungs, such as acute neonatal pneumonia, acute viral respiratory infection and resolving neonatal pneumonia (shown in dashed lines).

FIG. 21 illustrates line A as a chart in case of acute pneumonia.

It is typical to see a sharp simultaneous increase in the IR absorbance in the area of frequencies of about 1130 cm$^{-1}$ and 1160 cm$^{-1}$ with occasionally merge of these two peaks in a single large peak. Another sign of this condition is increase of the ratio of the peaks at frequencies of about 1130 cm$^{-1}$–1160 cm$^{-1}$ to a peak at a frequency of about 1250 cm$^{-1}$ to 2.6 and more (in norm—less than 1.0).

Also one can diagnose acute viral infection of upper respiratory tract (line B), if this peak ratio ranges from about 1.8 to about 2.2.

Line C indicates a significant reduction of the IR absorbance in the area of about 1130 cm$^{-1}$ and 1160 cm$^{-1}$, so that the peaks become much lower than the peak at about 1250 cm$^{-1}$, which is indicative of resolving neonatal pneumonia, but in adults can indicate other conditions.

Region 7: Frequency of 1400 CM$^{-1}$ to 1700 CM$^{-1}$

Brain and central nervous system disorders are reflected in the range of the IR absorbance spectra at about 1400 cm$^{-1}$ through 1700 cm$^{-1}$ and are illustrated on FIGS. 22 through 27.

As we mentioned above, a normal chart for this area with typical peaks at the frequencies of about 1410 cm$^{-1}$, 1460 cm$^{-1}$, 1550 cm$^{-1}$, and 1650 cm$^{-1}$ was illustrated on FIG. 1.

Whereat, the peaks at the frequencies of about 1410 cm$^{-1}$ and 1460 cm$^{-1}$ chiefly reflect early, less severe (usually, functional) damages of the brain and central nervous system (for example, minor degree of intracranial hypertension, neurosis, early stage of convulsion disorders).

Whereas the peaks at the frequencies of about 1550 cm$^{-1}$ and 1650 cm$^{-1}$ chiefly reflect more severe (usually, organic) damages of the brain and central nervous system (such as head and brain trauma, severe hypoxic encephalopathy with hemorrhage, meningitis etc.).

Figure 22:
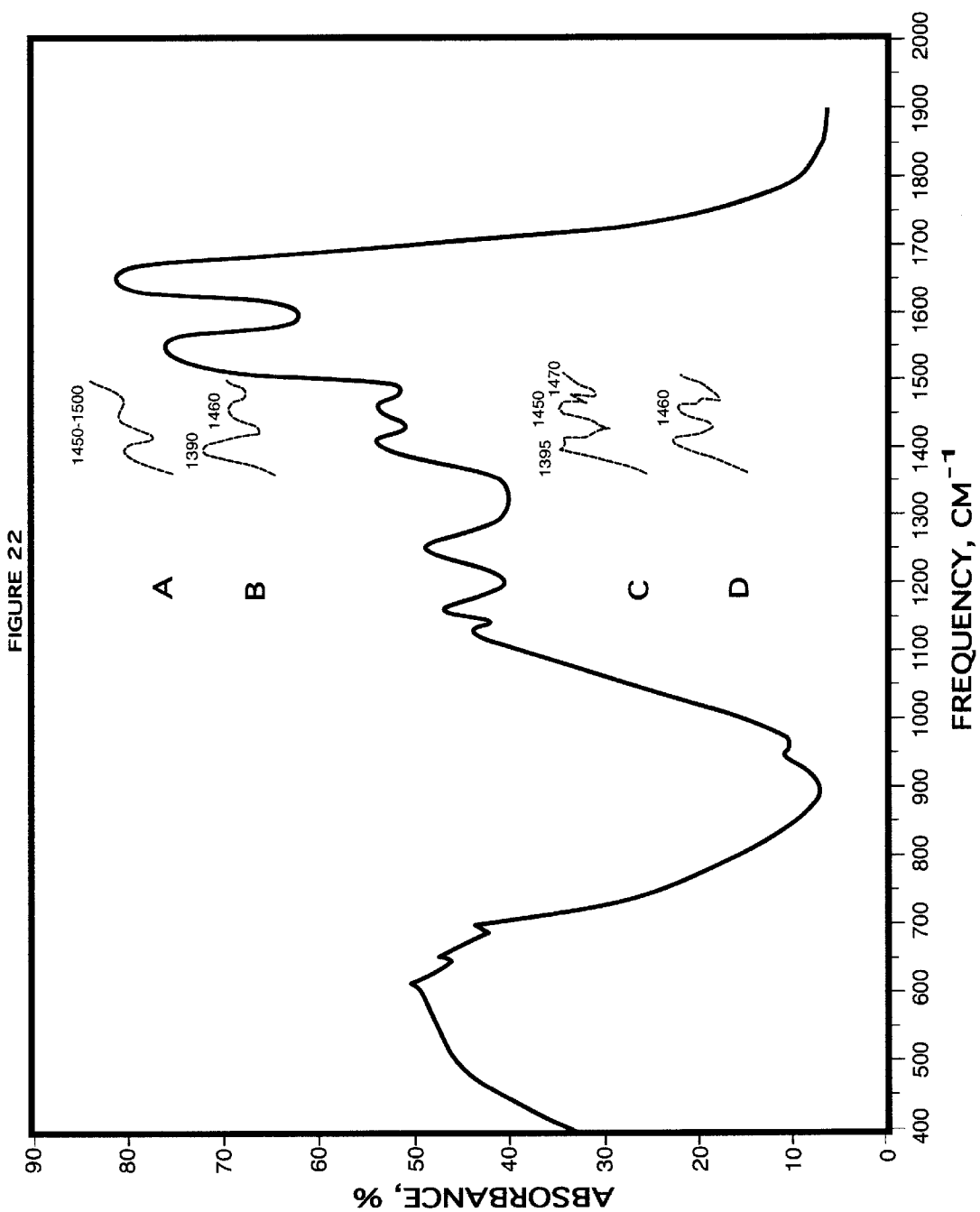
FIG. 22 is a chart illustrating the change from the normal chart (solid line) due to various specific pathologic conditions of central nervous system, such as neurosis, epilepsy and intracranial hypertension of different degree of severity (shown in dashed lines).

FIG. 22 contains examples of some diseases of the brain and central nervous system.

More specifically, line A represents a typical case of neurosis with a sharp increase in the IR absorbance in a frequency range from about 1450 cm$^{-1}$ to about 1500 cm$^{-1}$. Whereat, right descendent side of a peak at a frequency of about 1460 cm$^{-1}$ transforms into almost horizontal line.

Also, one can diagnose another kind of neurosis (not shown on the line) by a sharp increase in the IR absorbance of a peak at a frequency of about 1460 cm$^{-1}$ only. Whereat, the ratio of the peak at about 1410 cm$^{-1}$ to the peak at about 1460 cm$^{-1}$ becomes less than 1.0 (in norm-1.0).

Line B is a case of epilepsy and/or convulsion disorders. Whereat, there is a sharp decrease in the IR absorbance at a frequency of about the same point of 1460 cm$^{-1}$. One can identify a case of epilepsy, if the ratio of the peak at about 1410 cm$^{-1}$ to the peak at about 1460 cm$^{-1}$ is equal to 2.0 and more. Also a condition of convulsion disorders can be diagnosed if this peak ratio is 1.7–2.0.

Line C illustrates a condition of severe intracranial hypertension with dramatic change in the shape of a peak at about 1460 cm$^{-1}$. This peak widens to both left and right and shifts to the left to about 1450 cm$^{-1}$. Whereat, the right descent side of this peak is split by an appearance of a small peak at a frequency of about 1470 cm$^{-1}$, which is absent in norm.

At the same time the shape of a peak at a frequency of about 1410 cm$^{-1}$ also changes dramatically. This peak undergoes an increase in the height and width coupled with a cut top and shifts to the left to about 1395 cm$^{-1}$.

Line D is an example of minor intracranial hypertension in otherwise healthy men, where the only change is a little widening of the right side of a peak at a frequency of about 1460 cm$^{-1}$.

Figure 23:
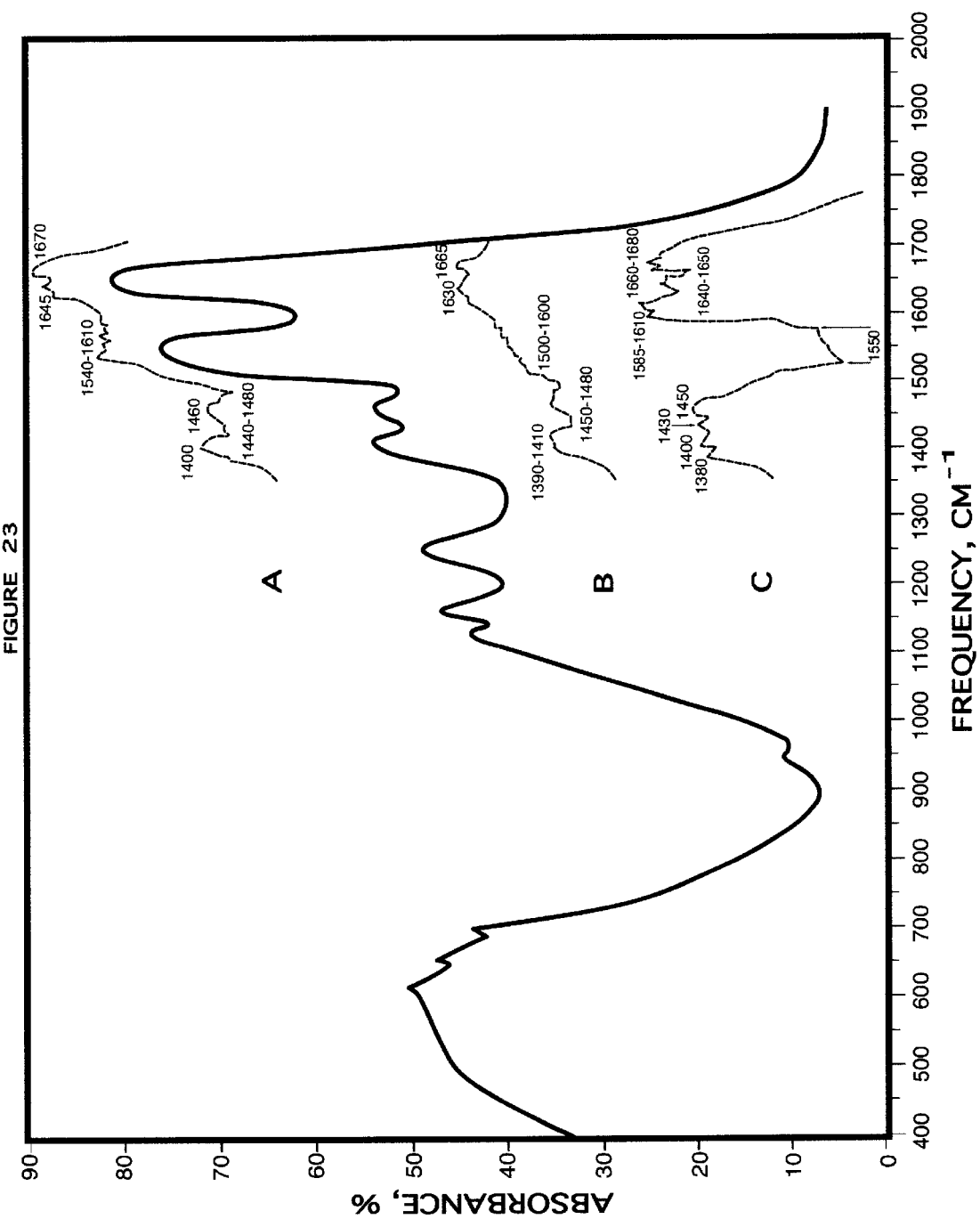
FIG. 23 is a chart illustrating the change from the normal chart (solid line) due to various other specific pathologic conditions of brain, such as perinatal encephalopathy with different degree of severity (shown in dashed lines).

FIG. 23 contains further examples of disorders of that group. Lines A, B and C are examples of ischemic perinatal encephalopathy with different degree of severity. As one can see on this figure the more pronounced the feature of the chart, the more advanced is the stage of the perinatal encephalopathy.

Line A represents a case of hypoxic ischemic perinatal encephalopathy of a mild degree. Whereat, one can identify a mild decrease in the IR absorbance at a frequency of about 1650 cm$^{-1}$ with a split into two small peaks at frequencies of about 1670 cm$^{-1}$ and 1645 cm$^{-1}$.

Also, a mild reduction in the IR absorbance in the area of the peak at a frequency of about 1550 cm$^{-1}$ with transformation into a "saw"-shaped horizontal line with a smaller peaks ranging from about 1540 cm$^{-1}$ to about 1610 cm$^{-1}$.

Then, one can see a moderate decrease in the IR absorbance in the area of a peak at a frequency of about 1460 cm$^{-1}$ with transformation into a widened and flattened peak, which is normally higher and narrower.

In addition, one should note a mild reduction in the IR absorbance of the peak at a frequency of about 1410 cm$^{-1}$, which becomes a little widened, flattened and shifts to the left to about 1400 cm$^{-1}$.

Line B is an example of hypoxic ischemic perinatal encephalopathy of a moderate degree. Here one can see a moderate decrease in the IR absorbance at a frequency of about 1650 cm$^{-1}$ with a split into two peaks at frequencies of about 1630 cm$^{-1}$ and 1665 cm$^{-1}$.

Also, a moderate decrease of the IR absorbance at about 1550 cm$^{-1}$ with a transformation into a "terrace"-shaped descendent line in a frequency range from about 1500 cm$^{-1}$ to about 1600 cm$^{-1}$.

Then, one can identify a moderate decrease of IR absorbance in the area of about 1460 cm$^{-1}$. Whereat, this peak converts into a short "trapezium"-like line with a cut top, occupying a wider range of about 1450 cm$^{31\ 1}$–1480 cm$^{-1}$.

Also, a moderate decrease in the IR absorbance occurs in the area of a peak at a frequency of about 1410 cm$^{-1}$ with a transformation into a wide "trapezium"-like line with a cut top, occupying a range of about 1390 cm$^{-1}$–1410 cm$^{-1}$.

Line C is a case of severe hypoxic ischemic perinatal encephalopathy with intracranial intraventricular hemorrage.

Here one can see a sharp decrease in the IR absorbance at a frequency of about 1650 cm$^{-1}$ with a very dramatic change in the shape. Whereat this peak widens both to the left and to the right occupying a wider range of about 1585 cm$^{-1}$–1680 cm$^{-1}$ coupled with the presence of three wide prominent peaks at frequencies of about 1585 cm$^{-1}$–1610 cm$^{-1}$, 1640 cm$^{-1}$–1650 cm$^{-1}$ and 1660 cm$^{-1}$–1680 cm$^{-1}$.

Also, an abrupt IR absorbance reduction exists in the area of about 1550 cm$^{-1}$ up until a complete disappearance of the peak in this area, which is normally present there.

In addition, one can identify a sharp absorbance decrease in the area of a peak at a frequency of about 1410 cm$^{-1}$ and a peak at a frequency of about 1460 cm$^{-1}$. Whereat, the absorbance band transforms into a "saw"-shaped line with a multitude of smaller peaks at the frequencies of about 1380 cm$^{-1}$, 1400 cm$^{-1}$, 1430 cm$^{-1}$ and 1450 cm$^{-1}$ in the area ranging from about 1380 to about 1460 cm$^{-1}$.

Figure 24:
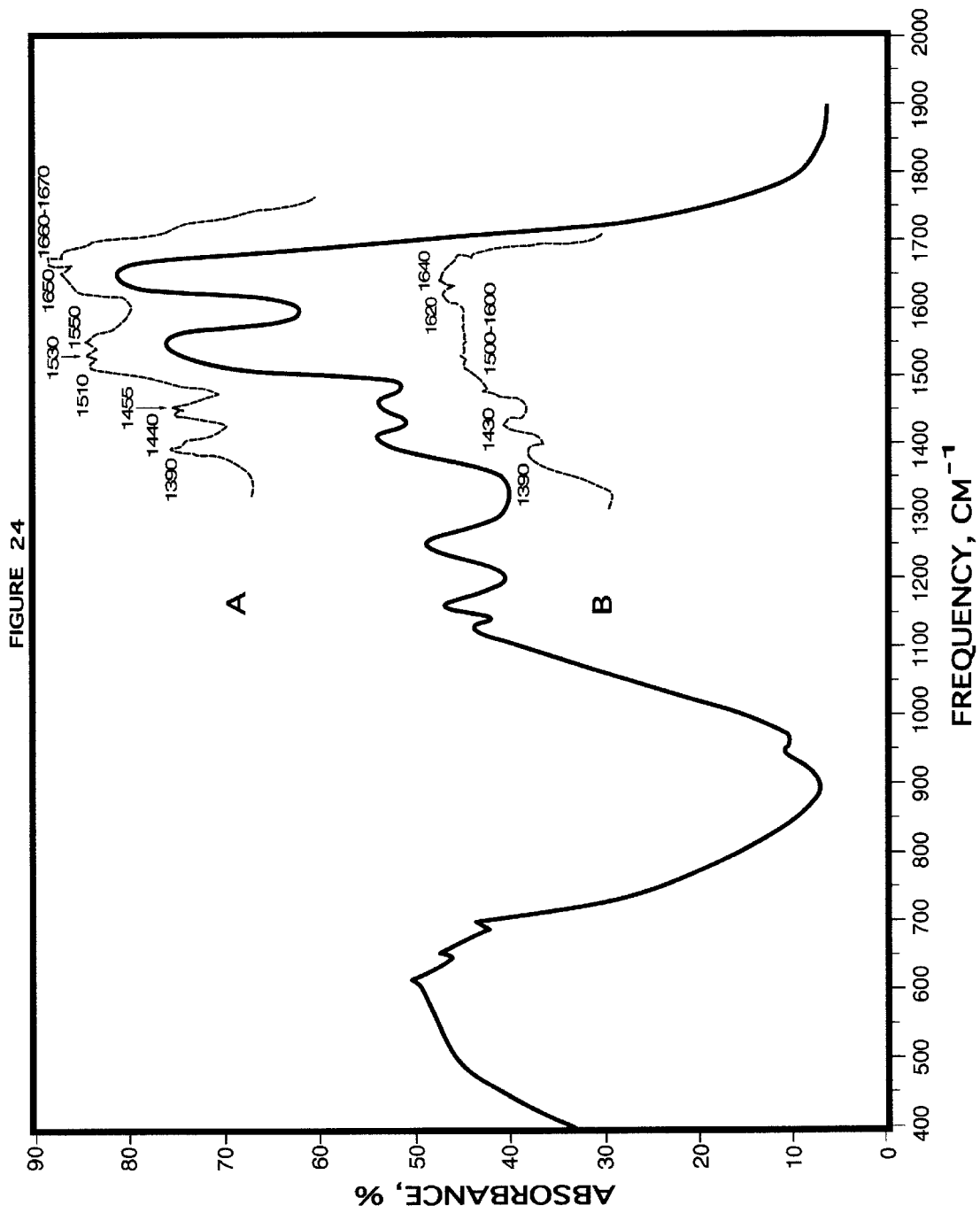
FIG. 24 is a chart illustrating the change from the normal chart (solid line) due to various conditions of brain, such as minor to moderate skull and brain injury or trauma (shown in dashed lines).

More examples are shown on FIG. 24.

Line A may be useful in diagnosis of brain injury of a minor degree. In this chart one can identify a slight decrease in the IR absorbance in the area of a peak at a frequency of about 1650 cm$^{-1}$ with a split on the top and an appearance of a small elongated "rectangular"-shaped peak at a frequency of about 1660 cm$^{-1}$–1670 cm$^{-1}$ and a small flat "tent"-like peak at a frequency of about 1650 cm$^{-1}$.

Also, a little decrease in the IR absorbance of a peak at a frequency of about 1550 cm$^{-1}$ with shift to the left to about 1510 cm$^{-1}$, occupying the area ranging from about 1510 cm$^{-1}$ to about 1550 cm$^{-1}$. Whereat this peak transforms into a "saw"-like line with three small peaks at frequencies of about 1510 cm$^{-1}$, 1530 cm$^{-1}$ and 1550 cm$^{-1}$.

Besides, one can see an increase of IR absorbance in the area of about 1460 cm$^{-1}$ with a shift to the left to about 1450 cm$^{-1}$ and a split on the top of this peak into two small peaks at frequencies of about 1440 cm$^{-1}$ and 1445 cm$^{-1}$.

In addition, it should be noted that an increase in the IR absorbance takes place in the area of a peak at a frequency of about 1410 cm$^{-1}$ with a shift to the left, occupying the area range of about 1390 cm$^{-1}$–1410 cm$^{-1}$. Also, one can identify an appearance of a small sharp peak at a frequency of about 1390 cm$^{-1}$, which is normally absent.

Line B is a case of postnatal head injury of a moderate degree.

In this situation one can identify a moderate decrease in the IR absorbance in the area of a peak at a frequency of about 1650 cm$^{-1}$ with a shift to the left, occupying the area range of about 1600 cm$^{-1}$ to about 1670 cm$^{-1}$. Whereat, there is a split at the top of this peak into two widened and flattened small peaks at frequencies of about 1620 cm$^{-1}$ and 1640 cm$^{-1}$.

Also, an abrupt reduction in the IR absorbance is observed in the area of a peak at a frequency of about 1550 cm$^{-1}$ with transformation into a "waived"-shaped horizontal line, ranging from about 1500 cm$^{-1}$ to about 1600 cm$^{-1}$.

Then, one can see that a peak at a frequency of about 1460 cm$^{-1}$ shifts to the left to about 1430 cm$^{-1}$.

In addition, one can identify a sharp decrease in the IR absorbance in the area of a peak at about 1410 cm$^{-1}$. Whereat, this peak shifts to the left to about 1390 cm$^{-1}$ and transforms into semicircle.

As a result of these changes, the ratio of the peak at about 1390 cm$^{-1}$ to the peak at about 1430 cm$^{-1}$ decreases to 0.4 (in norm-1.0).

Figure 25:
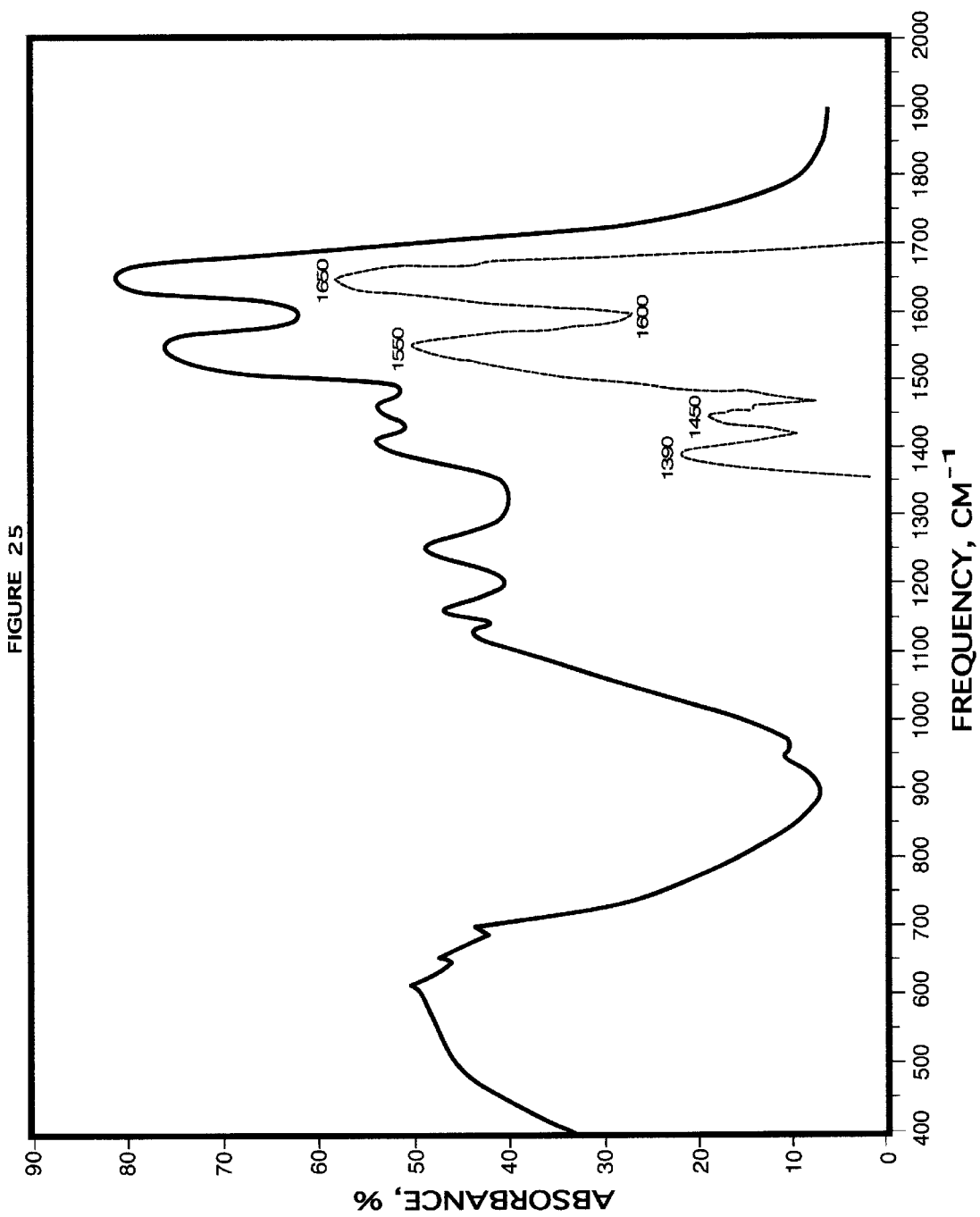
FIG. 25 is a chart illustrating the change from the normal chart (solid line) due to various other brain conditions, such as cerebral vascular atherosclerotic disease (shown in dashed lines).

Dashed line on FIG. 25 represents a condition of cerebrosclerosis.

Whereat, one can identify a sharp decrease of the IR absorbance at the frequencies of about 1500 cm$^{-1}$–1540 cm$^{-1}$, 1560 cm$^{-1}$–1640 cm$^{-1}$ and 1660 cm$^{-1}$ $^{-1700}$. As a result of this reduction the peaks at the frequencies of about 1550 cm$^{-1}$ and 1650 cm$^{-1}$ become much sharper rather than more rounded in norm.

Also, a powerful absorbance increase exists in the area of a peak at a frequency of about 1460 cm$^{-1}$ with a shift to the left to about 1450 cm$^{-1}$. The shape of this peak changes dramatically in such a way that it becomes much bigger and longer than in norm.

A similar powerful absorbance increase takes place in the area of a peak at a frequency of about 1410 cm$^{-1}$ with a shift to the left to about 1390 cm$^{-1}$. Analogously, the change in shape of this peak occurs in such a way that it also becomes much bigger and longer than in norm.

As a result of these changes, the ratio of the peak at about 1390 cm$^{-1}$ to the peak at about 1450 cm$^{-1}$ increases to 1.3 (in norm-1.0).

Figure 26:
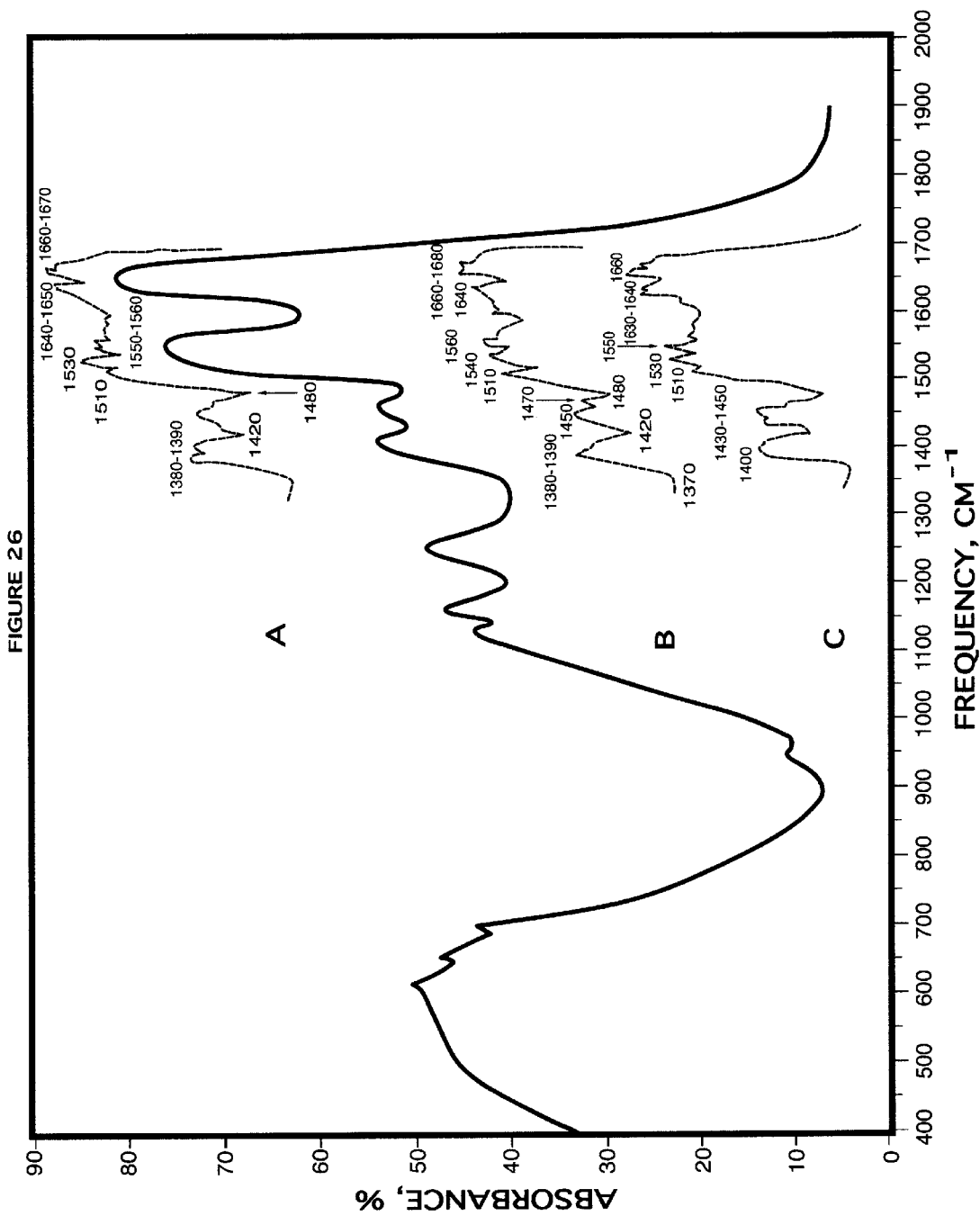
FIG. 26 is a chart illustrating the change from the normal chart (solid line) due to various more conditions of brain disease, such as meningitis with different degree of severity and arachnoiditis (shown in dashed lines).

FIG. 26 contains further examples of the diseases of central nervous system, such as the diseases of the linings of the brain, namely meningitis and arachnoiditis.

Lines A and B reflect a condition of acute bacterial meningitis. Whereat, line B represents a more severe case of this disease, although both charts are similar.

At first, one can see a split on the top of a peak at a frequency of about 1650 cm$^{-1}$ into two bulky peaks at the frequencies of about 1660 cm$^{-1}$–1670 cm$^{-1}$ and 1640 cm$^{-1}$–1650 cm$^{-1}$ (line A.).

One can identify a similar picture on line B, where there is a split on the top of a peak at a frequency of about 1650 cm$^{-1}$ into two bulky peaks at the frequencies of about 1660 cm$^{-1}$–1680 cm$^{-1}$ and 1640 cm$^{-1}$.

Whereat, a peak at a frequency of about 1650 cm$^{-1}$ transforms into an "M"-like line with pronounced peaks (compare with lines A and B on FIGS. 23 and 24).

Also, on line B there is a decrease in the IR absorbance at a frequency of about 1650 cm$^{-1}$ and a widening to both left and right, occupying the area range of about 1600 cm$^{-1}$ to about 1700 cm$^{-1}$ (compare with line A on FIG. 26).

Secondly, one can identify an increase in the IR absorbance in the area ranging from about 1570 cm$^{-1}$ to about 1630 cm$^{-1}$, especially at a frequency of about 1600 cm$^{-1}$ to be exact. Whereat, the peaks at the frequencies of about 1650 cm$^{-1}$ and 1550 cm$^{-1}$ are almost merging (compare with line A on FIGS. 23 and 24).

Also, there is a split on the top of a peak at a frequency of about 1550 cm$^{-1}$ with an appearance of three pronounced peaks at the frequencies of about 1550 cm$^{-1}$–1560 cm$^{-1}$, 1530 cm$^{-1}$ and 1510 cm$^{-1}$ (Line A). Analogously on line B these peaks take place at the frequencies of about 1560 cm$^{-1}$, 1540 cm$^{-1}$ and 1510 cm$^{-1}$. Whereat, the peaks on line B are more pronounced, than on line A, especially at a frequency of about 1510 cm$^{-1}$.

If one compares the areas at a frequency of about 1550 cm$^{-1}$ on FIG. 26 to the lines A and B on FIG. 23 and line B on FIG. 24, one will see difference. Although line A on FIG. 24 and line A on FIG. 26 look similar in this area, it is easy to differentiate them by a peak at a frequency of about 1530 cm$^{-1}$, which is higher and has another shape on FIG. 26, than on FIG. 24.

Further, one can see a powerful increase in the IR absorbance in the area of a peak at a frequency of about 1460 cm$^{-1}$ with a dramatic change in the shape. In less severe cases this peak becomes much sharper and wider (line A). In more severe cases this peak is split on the top into two peaks at the frequencies of about 1450 cm$^{-1}$ and 1470 cm$^{-1}$ (line B). In both cases there is a widening of the base of a peak at a frequency of about 1460 cm$^{-1}$ to the left and to the right in such a way that the absorbance band occupies the range of about 1420 cm$^{-1}$ to about 1480 cm$^{-1}$.

Finally, it should be also noted that a powerful increase in the IR absorbance exists in the area of a peak at a frequency of about 1410 cm$^{-1}$ (line A and line B). In this situation this peak is much sharper, wider and higher, and also shifts to the left to the area of about 1380 cm$^{-1}$–1390 cm$^{-1}$(line B), with occasional further split on the top into two smaller peaks (line A). Whereat, the base of a peak at a frequency of about 1410 cm$^{-1}$ is dramatically widened in such a way that the absorbance band occupies the range of about 1370 cm$^{-1}$ to about 1420 cm$^{-1}$.

Line C of the chart is a case of arachnoiditis, which is somewhat similar to the previous cases of meningitis.

In that case, one can see a split on the top of a peak at a frequency of about 1650 cm$^{-1}$ into two peaks at frequencies of about 1630 cm$^{-1}$–1640 cm$^{-1}$ and 1660 cm$^{-1}$, but they are less pronounced.

Also, there is a split on the top of a peak at a frequency of about 1550 cm$^{-1}$ into three peaks at frequencies of about 1510 cm$^{-1}$, 1530 cm$^{-1}$ and 1550 cm$^{-1}$, but they are less pronounced too (compare with line B).

Then, an increase in the IR absorbance takes place in the area of a peak at a frequency of about 1460 cm$^{-1}$ with a shift to the left to about 1430 cm$^{-1}$–1450 cm$^{-1}$. Whereat, this peak becomes higher and narrower, than in case of meningitis.

In addition, it should be noted that there is an increase in the IR absorbance in the area of a peak at about 1410 cm$^{-1}$ with a shift to the left to about 1400 cm$^{-1}$. This peak also becomes narrower than in case of meningitis.

As a whole, one can identify that in case of arachnoiditis there are more pronounced shifts to the left of the peaks at frequencies of about 1630 cm$^{-1}$–1640 cm$^{-1}$ and 1430 cm$^{-1}$–1450. In addition, a peak in the area of about 1430 cm$^{-1}$–1450 cm$^{-1}$ and a peak at a frequency of about 1400 cm$^{-1}$ are more stretched and not as wide as in the case of meningitis.

Figure 27:
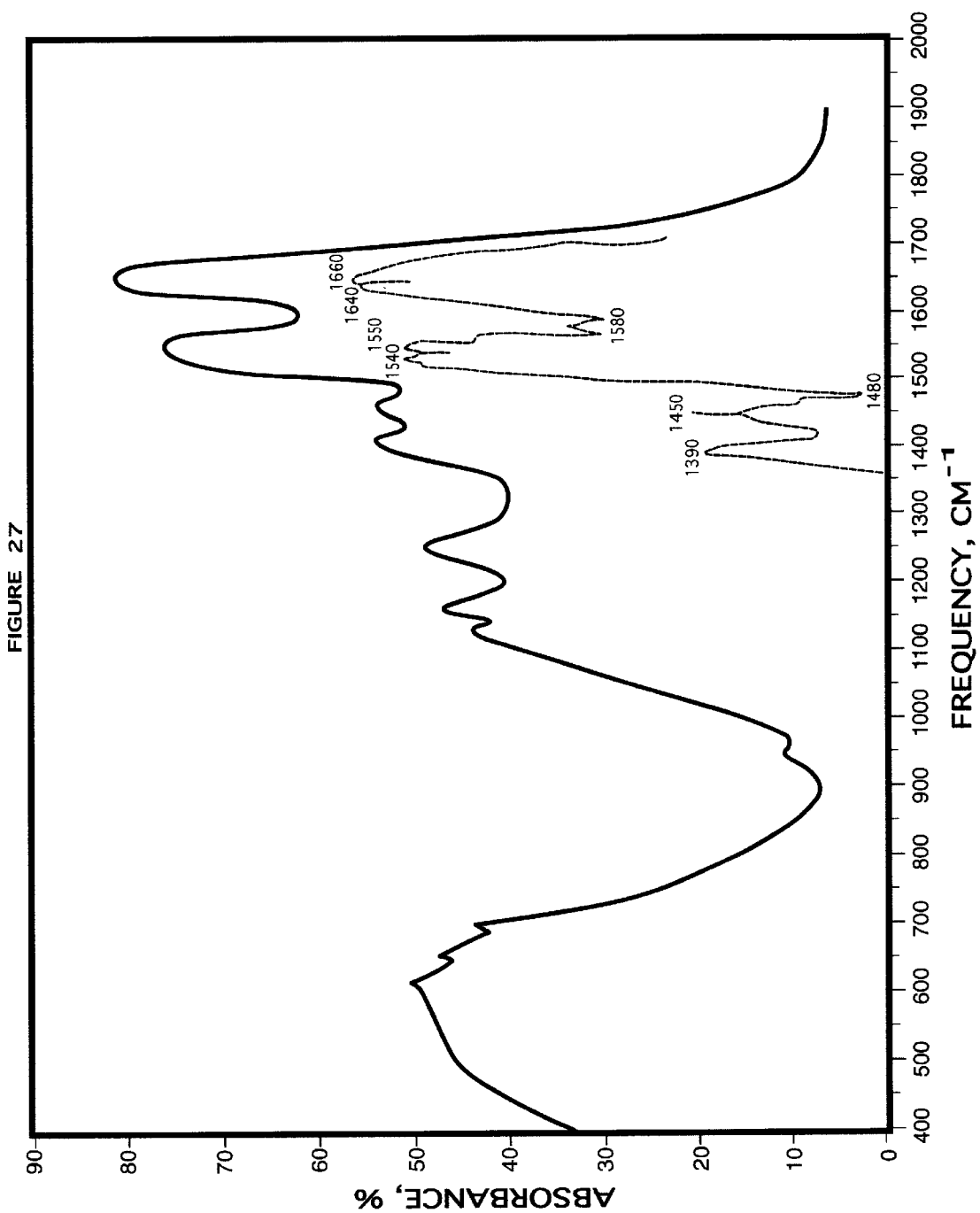
FIG. 27 is a chart illustrating the change from the normal chart (solid line) due to the central nervous system condition of rheumatic chorea (shown in dashed lines).

FIG. 27 illustrates a typical case of rheumatic chorea (dashed line) with a split without divergence on the top of a peak at a frequency of about 1650 cm$^{-1}$. Two elongated peaks at frequencies of about 1640 cm$^{-1}$ and 1660 cm$^{-1}$ appear as a result of this split.

Also, a similar split without divergence can be seen on the top of a peak at a frequency of about 1550 cm$^{-1}$. Analogously, two elongated peaks at frequencies of about 1540 cm$^{-1}$ and 1560 cm$^{-1}$ appear as a result of this split.

Then, one can see an appearance of a new peak at a frequency of about 1580 cm$^{-1}$, which is absent in norm.

Further, one can identify a powerful absorbance increase in the area of a peak at a frequency of about 1460 cm$^{-1}$. Whereat, this peak shifts to the left to about 1450 cm$^{-1}$ and becomes much bigger and longer than in norm coupled with an appearance of a vertical line on its top.

Also there is a sharp absorbance drop in the area of about 1480 cm$^{-1}$.

Finally, it should be noted that a sharp absorbance increase takes place in the area of a peak at a frequency of about 1410 cm$^{-1}$. This peak shifts to the left to the area of about 1390 cm$^{-1}$ and also becomes much bigger and longer than in norm.

As a result of this changes the ratio of the peak in the area of about 1390 cm$^{-1}$ to the peak at about 1450 cm$^{-1}$ increases to about 1.2–1.3 (in norm-1.0).

Region 8: Frequency of 3000 cm$^{-1}$ to 3100 cm$^{-1}$

Figure 28:
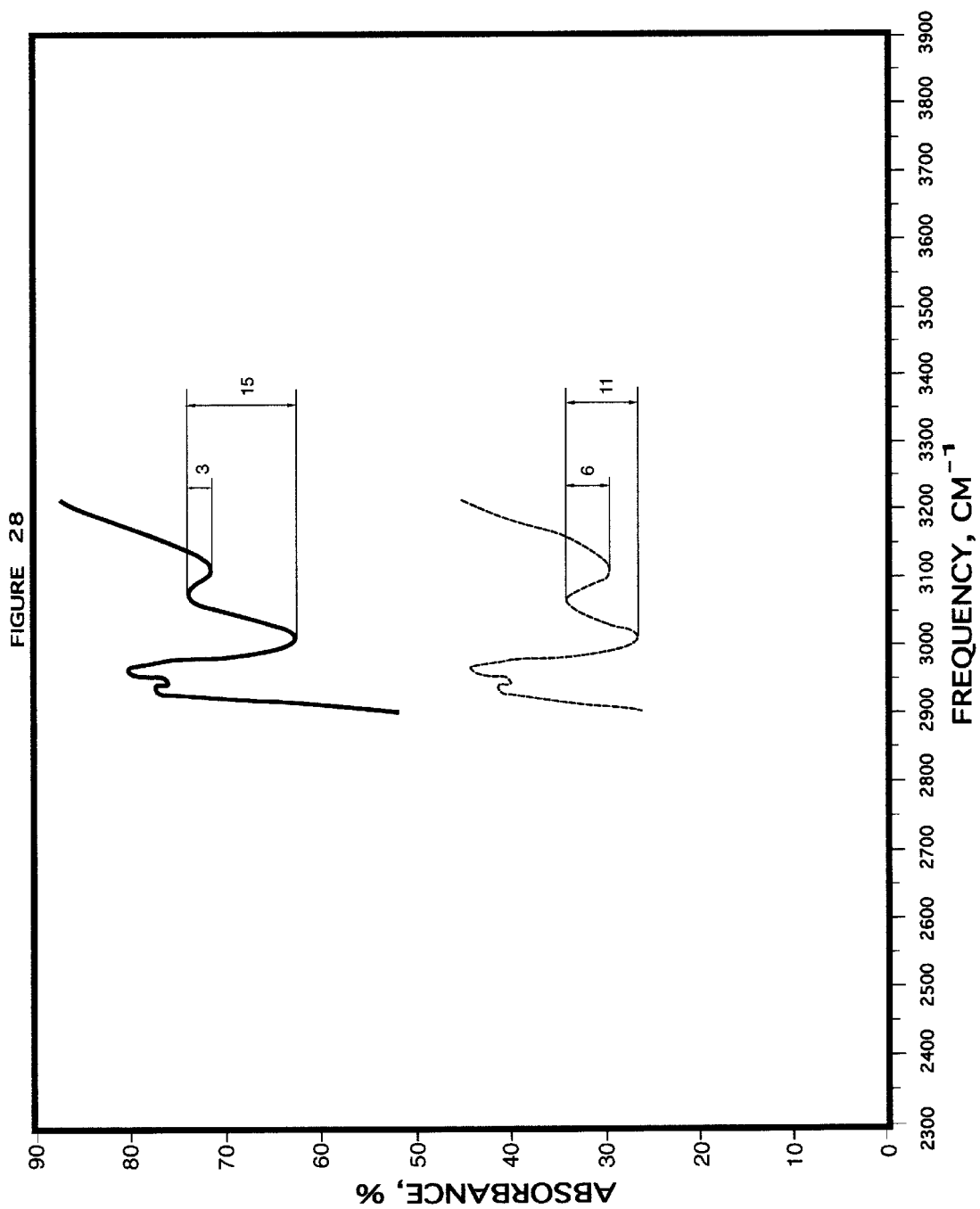
FIG. 28 is a chart illustrating the change from the normal chart (solid line) due to severe chronic infection, such as pulmonary tuberculosis (shown in dashed lines).

Final REGION 8 (FIG. 28) deserves particular attention in the area of about 3000 cm$^{-1}$–3100 cm$^{-1}$, especially a peak at a frequency of about 3060 cm$^{-1}$. This REGION can be used for diagnosis of a different degree of chronic infection, in particular, a severe chronic infection, such as pulmonary tuberculosis.

As one can see, there is a sharp IR absorbance reduction in this area and a significant change in shape of a peak at a frequency of about 3060 cm$^{-1}$ (dashed line vs. solid line). The ratio of the height for the rising line to that of a subsequent declining line of this peak for the healthy population is about 5 (15 units to 3 units on the solid line chart). While in case of a pulmonary tuberculosis it drops to about 2 (11 units to 6 units on the dashed line chart). In patients with chronic urology and gynecologic infections this ratio can be about 2.7.

In addition to certain organ specific diseases affecting a particular narrow portion of the absorbance spectra as was described in detail above, some other organ specific conditions affect the whole chart.

Figure 29:
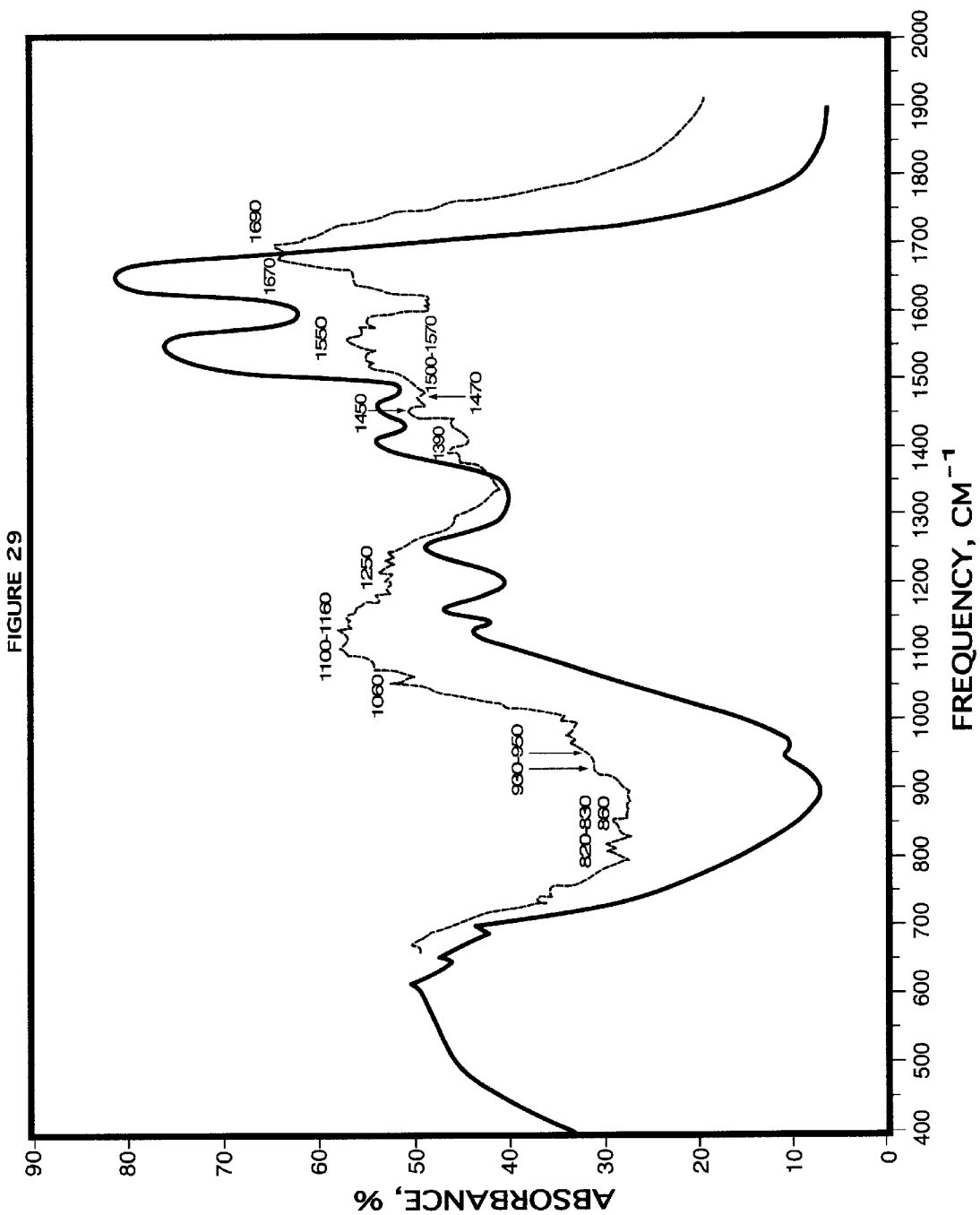
FIG. 29 is a chart illustrating the change from the normal chart (solid line) due to the condition of physical and mental retardation with damage of different systems and internal organs of the body as a result of brain damage at birth (shown in dashed lines).

An example of such condition is shown on FIG. 29, illustrating a case of severe brain damage in a developmentally disabled blind infant with physical and mental retardation, one year after a postnatal head injury. On this figure one can see a substantial and overwhelming differences and multiple deviations across the whole IR spectra in comparison to a norm. In this case the changes occur throughout many of the patient's organs and systems.

First of all, there is an abrupt reduction in the area of about 1650 cm$^{-1}$ with a sharp shift to the right and a dramatic change in the shape. Whereat, this peak transforms into a very elongated "trapezium"-like line with a hollow cut top at a frequency of about 1670 cm$^{-1}$–1690 cm$^{-1}$ with a widening of the base of "trapezium" to both left and right, occupying the range of about 1600 cm$^{-1}$ to about 1740 cm$^{-1}$.

Secondly, one can see an abrupt absorbance reduction in the area of a peak at a frequency of about 1550 cm$^{-1}$. This peak shifts to the left and transforms into a "rectangular-trapezium"-like line with a "waved"-shaped top at a frequency of about 1500 cm$^{-1}$–1570 cm$^{-1}$ with a small peak at a frequency of about 1545 cm$^{-1}$ and a wide base, occupying the range of about 1480 cm$^{-1}$ to about 1580 cm$^{-1}$.

Further, it should be noted that there is a sharp absorbance decrease in the area of a peak at a frequency of about 1460 cm$^{-1}$. Whereat, this peak shifts to both left and right and a dramatic change in the shape takes place accompanied by transformation into two peaks: a small one at a frequency of about 1450 cm$^{-1}$ and a smaller one at a frequency of about 1470 cm$^{-1}$.

Finally, one can identify an abrupt absorbance reduction in the area of a peak at a frequency of about 1410 cm$^{-1}$. This peak shifts to the left to about 1390 cm$^{-1}$ and becomes flattened and widened in such a way that the base of a peak occupies the range of about 1370 cm$^{-1}$ to about 1400 cm$^{-1}$.

As a result of these changes, the ratio of the peak in the area of about 1410 cm$^{-1}$ to the peak in the area of about 1460 cm$^{-1}$ decreases to about 0.4 (in norm −1.0).

The above picture is a result of damages of central nervous system in a developmentally disabled blind infant with physical and mental retardation (REGION 7).

Among other features one can also identify a state of pneumonia (the peak ratio in the area of about 1100 cm$^{-1}$–1160 cm$^{-1}$ to about 1250 cm$^{-1}$ is about 3.5 on MIXED REGION 6).

Then, it should be noted a state of chronic hypoacidic gastritis can be diagnosed (the lack of the peak at about 930 cm$^{-1}$–950 cm$^{-1}$ on REGION 3, Subregion 3B).

Also, one can see a state of active chronic nephritis (appearance the peak at about 850 cm$^{-1}$–860 cm$^{-1}$ on REGION 3, Subregion 3A) etc.

Figure 30:
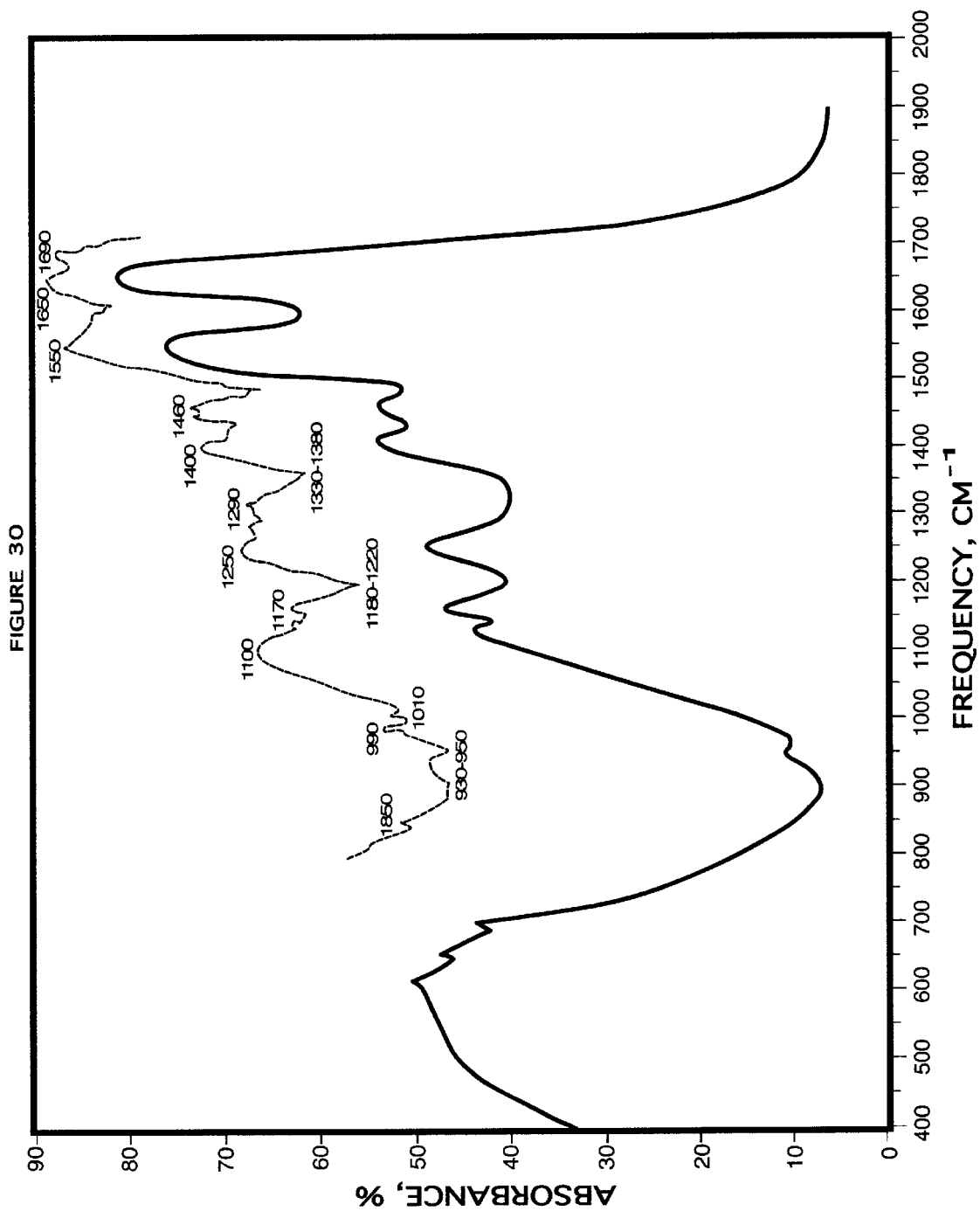
FIG. 30 is a final chart illustrating the change from the normal chart (solid line) due to epidermolysis bullosa (shown in dashed lines)—a rare congenital disorder with damage of the different systems and internal organs of the body.

Finally, an example of epidermolysis bullosa (an illness with multiple disorders of different systems) is shown on FIG. 30.

Epidermolysis bullosa is a rare congenital disease of connective tissues associated with cutaneous lesions and gastrointestinal disorders (especially esophagitis: the peak at a frequency of about 990 cm$^{-1}$). In this case, the changes are also very pronounced and affect the wide range of absorbance frequencies reflecting the profound changes caused by the disease to the whole body.

Although the present invention has been described with respect to several specific embodiments and applications, it is not limited thereto. Numerous variations and modifications readily will be appreciated by those skilled in the art such as the use of the method of the invention to diagnose various pathological conditions in animals in veterinary medicine; determining the disease conditions of plants by the IR spectra of the circulating liquids and juices, etc. These and other variations are intended to be included within the scope of the present invention, which is recited in and limited only by the following claims.

I claim:

1. A method for rapid diagnosis of an organ specific disease state of a subject, using an infrared spectroscopy of a blood sample of said subject, said method comprising the steps of:

irradiating said blood sample with an infrared light, obtaining an infrared absorbance spectra of said blood sample in a frequency ranging from about 400 $cm^{-1}$ to about 2000 $cm^{-1}$ and further from about 3000 $cm^{-1}$ to about 3100 $cm^{-1}$, comparing said infrared absorbance spectra with a normal infrared absorbance spectra correspondingly obtained from blood of known healthy subjects, identifying deviations of said infrared absorbance spectra from said normal infrared absorbance spectra in predetermined organ specific regions of said frequency range, and providing a diagnosis for an organ specific disease state based on the presence of said deviations.

2. The method as in claim 1, wherein said subject being a human subject.

3. The method as in claim 1, further including a step of determining a degree of said organ specific disease state based on intensity of said deviations.

4. The method as in claim 2, further including a step of examining a region of said infrared absorbance spectra in a frequency range from about 600 $cm^{-1}$ to about 700 $cm^{-1}$ for a presence of deviations from said normal infrared absorbance spectra, said presence indicating a state of hypoxia.

5. The method as in claim 4, further including a step of examining said region of said infrared absorbance spectra for a presence of a peak at a frequency of about 620 $cm^{-1}$, whereby such presence indicating a state of asphyxia of neonates or forceful strangling in adults.

6. The method as in claim 4, further including a step of examining said region of said infrared absorbance spectra for a presence of a peak at a frequency of about 660 $cm^{-1}$, whereby such presence indicating a state of heart failure hypoxia.

7. The method as in claim 2, further including a step of examining a region of said infrared absorbance spectra in a frequency range from about 700 $cm^{-1}$ to about 800 $cm^{-1}$ for a presence of deviations from said normal infrared absorbance spectra, said presence including a state of liver failure.

8. The method as in claim 7, further including a step of examining said region of said infrared absorbance spectra for a presence of three peaks at the frequencies of about 720 $cm^{-1}$, 740 $cm^{-1}$, and 770 $cm^{-1}$, whereby such presence indicating a state of liver failure.

9. The method as in claim 2, further including a step of examining a region of said infrared absorbance spectra in a frequency range from about 800 $cm^{-1}$ to about 900 $cm^{-1}$ for a presence of deviations from said normal infrared absorbance spectra, said presence indicating a disease state of an organ selected from a group of organs consisting of a colon, kidneys, and endocrine glands.

10. The method as in claim 9, further including a step of examining a region of said infrared absorbance spectra in a frequency range from about 850 $cm^{-1}$ to about 860 $cm^{-1}$ for a presence of deviations from said normal infrared absorbance spectra, said presence indicating a disease state of kidneys.

11. The method as in claim 10, further including a step of examining said region of said infrared absorbance spectra for a presence of a peak at a frequency of about 850 $cm^{-1}$, whereby such presence indicating a state of acute nephritis or active form of chronic nephritis.

12. The method as in claim 10, further including a step of examining said region of said infrared absorbance spectra for a presence of a rounded negative peak at a frequency of about 850 $cm^{-1}$, said presence indicating a state of inactive form of chronic nephritis, correlated with nephrolithiasis and/or urinary sand.

13. The method as in claim 9, further including a step of examining a region of said infrared absorbance spectra in a frequency range from about 850 $cm^{-1}$ to about 900 $cm^{-1}$ for a presence of deviations from said normal infrared absorbance spectra, said presence indicating a disease state of a colon.

14. The method as in claim 13, further including a step of examining said region of said infrared absorbance spectra in a frequency range from about 850 $cm^{-1}$ to about 900 $cm^{-1}$ for a presence of an increase in absorbance over said range of frequencies, said increase in comparison to said normal infrared absorbance spectra indicating a disease state of acute colitis.

15. The method as in claim 13, further including a step of examining a region of said infrared absorbance spectra in a frequency range from 850 $cm^{-1}$ to about 900 $cm^{-1}$ for a presence of reduction in absorbance over said range of frequencies, said reduction in comparison to said normal infrared absorbance spectra indicating a disease state of chronic colitis.

16. The method as in claim 9, further including a step of examining a region of said infrared absorbance spectra for a presence of deviations from said normal infrared absorbance spectra in a frequency range from about 880 $cm^{-1}$ to about 900 $cm^{-1}$, said presence indicating a disease state of endocrine glands.

17. The method as in claim 16, further including a step of examining said region of said infrared absorbance spectra for a presence of an "equilateral triangle"-shaped sharp small peak at a frequency of about 880 $cm^{-1}$, said presence indicating a state of mild endocrine disorders correlated with a disease state of diencephalic syndrome and obesity.

18. The method as in claim 16, further including a step of examining said region of said infrared absorbance spectra for a presence of an elongated rounded peak at a frequency range from about 880 $cm^{-1}$ to about 890 $cm^{-1}$ coupled with "elliptical"-like line at a frequency of about 865 $cm^{-1}$, whereby such presence indicating a state of severe endocrine disorder correlated with a disease state of pituitary dwarfism.

19. The method as in claim 16, further including a step of examining said region of said infrared absorbance spectra for a presence of a bulky "trapezium"-like peak with a flat top at a frequency range from about 880 $cm^{-1}$ to about 890 $cm^{-1}$ coupled with a "V"-shaped line at a frequency of about 870 $cm^{-1}$, said presence indicating a state of very severe endocrine disorder correlated with a disease state of congenital pigmented nevi.

20. The method as in claim 16, further including a step of examining said region of said infrared absorbance spectra for a presence of a slightly rounded negative peak at a frequency of about 890 $cm^{-1}$, whereby such presence indicating a state of thyroid gland disorders correlated with a disease state of hyperthyroidism.

21. The method as in claim 2, further including a step of examining a region of said infrared absorbance spectra in a frequency range from about 900 $cm^{-1}$ to about 1000 $cm^{-1}$ for a presence of deviations from said normal infrared absorbance spectra, said presence indicating a disease state of an organ selected from a group of organs consisting of a stomach, a pancreas, a duodenum, an jejunum, an ileum, an appendix, and also different tumors associated with immunodeficiency disorders.

22. The method as in claim 21, further including a step of examining said region of said infrared absorbance spectra in a frequency range from about 930 cm$^{-1}$ to about 950 cm$^{-1}$ for a presence of deviations in absorbance (over said range of frequencies) from said normal infrared absorbance spectra, said presence indicating a state of stomach disease.

23. The method as in claim 22, further including a step of examining said region of said infrared absorbance spectra for a presence of a large rounded peak at a frequency from about 930 cm$^{-1}$ to about 950 cm$^{-1}$, which is much higher and wider than in normal condition, whereby such presence indicating a disease state of acute gastritis.

24. The method as in claim 22, further including a step of examining said region of said infrared absorbance spectra for a presence of a large "trapezium"-like peak at a frequency range from about 930 cm$^{-1}$ to about 950 cm$^{-1}$, which is higher and wider than in normal condition, said presence indicating a disease state of chronic hypertrophic gastritis.

25. The method as in claim 22, further including a step of examining said region of said infrared absorbance spectra for a presence of a large "trapezium"-shaped peak with a "terrace"-like descent of both sides at a frequency range from about 930 cm$^{-1}$ to about 950 cm$^{-1}$, which is higher and wider than in normal condition, whereby such presence indicating a disease state of chronic atrophic gastritis.

26. The method as in claim 22, further including a step of examining said region of said infrared absorbance spectra for a presence of a reduced peak which transforms into a straight line at a frequency range from about 930 cm$^{-1}$ to about 950 cm$^{-1}$, said presence indicating a disease state of chronic hypoacidic gastritis.

27. The method as in claim 21, further including a step of examining said region of said infrared absorbance spectra for a presence of a sharp peak at a frequency of about 940 cm$^{-1}$ over the enlarged rounded peak at a frequency range from about 930 cm$^{-1}$ to about 950 cm$^{-1}$, whereby such presence indicating a disease state of pancreatitis.

28. The method as in claim 21, further including a step of examining a region of said infrared absorbance spectra in a frequency range from about 950 cm$^{-1}$ to about 970 cm$^{-1}$ for a presence of deviations from said normal infrared absorbance spectra, said presence indicating a state of a duodenum disease.

29. The method as in claim 28, further including a step of examining said region of said infrared absorbance spectra for a presence of a small rounded peak at a frequency range from about 950 cm$^{-1}$ to about 970 cm$^{-1}$, said presence indicating a disease state of acute duodenitis.

30. The method as in claim 28, further including a step of examining said region of said infrared absorbance spectra for a presence of a straight line or a rounded (or sharp) negative peak at a frequency range from about 950 cm$^{-1}$ to about 970 cm$^{-1}$, whereby such presence indicating a disease state of chronic duodenitis.

31. The method as in claim 21, further including a step of examining a region of said infrared absorbance spectra in a frequency range from about 970 cm$^{-1}$ to about 1000 cm$^{-1}$ for a presence of deviations from said normal infrared absorbance spectra, said presence indicating a disease state of an jejunum and an ileum.

32. The method as in claim 31, further including a step of examining said region of said infrared absorbance spectra in a frequency range from about 970 cm$^{-1}$ to about 1000 cm$^{-1}$ for a presence of a reduction in absorbance over said range of frequencies and flattening the absorbance band of the same height as the stomach portion of the chart, said reduction in comparison to said normal infrared absorbance spectra, indicating a disease state of enteritis with terminal ileitis.

33. The method as in claim 21, further including a step of examining said region of said infrared absorbance spectra for a presence of a "V"-shaped line at a frequency of about 960 cm$^{-1}$ and a "trapezium"-like peak with a squint cut top at a frequency range from about 910 cm$^{-1}$ to about 930 cm$^{-1}$, whereby such presence indicating a disease state of acute catarrhous appendicitis.

34. The method as in claim 21, further including a step of examining said region of said infrared absorbance spectra for a presence of an ascendent "step"-shaped line with a first step at a frequency range from about 935 cm$^{-1}$ to about 970 cm$^{-1}$ and a second step at a frequency range from about 970 cm$^{-1}$ to about 1000 cm$^{-1}$ coupled with a little peak at a frequency of about 930 cm$^{-1}$, whereby such presence indicating a disease state of acute phlegmonous appendicitis.

35. The method as in claim 21, further including a step of examining a region of said infrared absorbance spectra at a frequency of about 908 cm$^{-1}$ for a presence of deviations from said normal infrared absorbance spectra, said presence indicating a state of some tumor diseases associated with immunodeficiency disorders.

36. The method as in claim 35, further including a step of examining said region of said infrared absorbance spectra for a presence of a big peak at a frequency of about 908 cm$^{-1}$ with a wide base at a frequency range from about 880 cm$^{-1}$ to about 930 cm$^{-1}$ coupled with the lack of a peak at a frequency range from about 930 cm$^{-1}$ to about 950 cm$^{-1}$, which is normally presented, whereby such presence indicating a state of a malignant tumor disease known as retroperitoneal lymphoma.

37. The method as in claim 35, further including a step of examining said region of said infrared absorbance spectra for a presence of a little peak at a frequency of about 908 cm$^{-1}$ coupled with a descendent "step"-like line with a first step at a frequency range from about 930 cm$^{-1}$ to about 950 cm$^{-1}$ and a second step at a frequency range from about 960 cm$^{-1}$ to about 980 cm$^{-1}$, instead of a normally presented peak at a frequency range from about 930 cm$^{-1}$ to about 950 cm$^{-1}$, said presence indicating a state of a benign tumor disease known as congenital pigmented nevi.

38. The method as in claims 13 or 31, further including a step of examining said region of said infrared absorbance spectra for a presence of a significant reduction in the infrared absorbance in the frequency range from about 850 cm$^{-1}$ to about 1000 cm$^{-1}$ coupled with a large elliptical peak with a wide base at a frequency of about 930 cm$^{-1}$, occupying the range from about 900 cm$^{-1}$ to about 950 cm$^{-1}$, whereby such presence indicating a disease state of insufficiency of ileocecal valve.

39. The method as in claims 13 or 31, further including a step of examining said region of said infrared absorbance spectra for a presence of a powerful decrease in the infrared absorbance in a frequency range of about 800 cm$^{-1}$ to about 1000 cm$^{-1}$ coupled with a "trough"-shaped line with a wide hollow at a frequency range from about 860 cm$^{-1}$ to about 950 cm$^{-1}$, said presence indicating a disease state of celiac sprue.

40. The method as in claims 13 or 31, further including a step of examining said region of said infrared absorbance spectra for a presence of a "large broken wave"-shaped line in the area ranging from about 850 cm$^{-1}$ to about 1000 cm$^{-1}$, instead a normally presented absorbance band in this area, whereby such presence indicating a state of acute brucellosis with primarily gastrointestinal complications (acute colitis and acute enteritis).

41. The method as in claims 13 or 31, further including a step of examining said region of said infrared absorbance spectra for a presence of a peak at a frequency of about 980 cm$^{-1}$ of the same elevation as the stomach portion of the chart, coupled with a more sharp angle at a frequency of about 900 cm$^{-1}$ (instead normally presented more rounded elliptic angle), said presence indicating a state of lambliasis.

42. The method as in claims 13 or 31, further including a step of examining said region of said infrared absorbance spectra for a presence of a sharp peak at a frequency of about 980 cm$^{-1}$, which is higher than the stomach portion of the chart, and simultaneous turn into the opposite side of the absorbance band in a frequency range from about 850 cm$^{-1}$ to about 900 cm$^{-1}$, whereby such presence indicating a state of enterobiasis.

43. The method as in claim 13 or 31, further including a step of examining said region of said infrared absorbance spectra for a presence of a powerful increase in the infrared absorbance in a frequency range from about 720 cm$^{-1}$ to about 1000 cm$^{-1}$ with a shift to the right and a turn into the opposite side, said presence indicating a state of dolichocolon (or extreme elongated colon).

44. The method as in claim 2, further including a step of examining a region of said infrared absorbance spectra in a frequency range from about 1000 cm$^{-1}$ to about 1130 cm$^{-1}$ for a presence of deviations from said normal infrared absorbance spectra, said presence indicating a disease state of an organ selected from a group of organs, consisting of a liver and immune system.

45. The method as in claim 44, further including a step of examining said region of said infrared absorbance spectra for a presence of two sharp elongated peaks at the frequencies of about 1030 cm$^{-1}$ and 1060 cm$^{-1}$, having a "M"-shaped line, whereby such presence indicating a state of very severe immunodeficiency, correlated with malignant tumor, such as retroperitoneal lymphoma.

46. The method as in claim 44, further including a step of examining said region of said infrared absorbance spectra for a presence of two pronounced wide peaks at the frequencies of about 1050 cm$^{-1}$ and 1080 cm$^{-1}$, having a "M"-shaped bending line, said presence indicating a state of severe immunodeficiency, correlated with benign tumor, such as congenital pigmented nevi.

47. The method as in claim 44, further including a step of examining said region of said infrared absorbance spectra for a presence of a small peak at a frequency of about 1050 cm$^{-1}$ and a large rounded peak with a wide base at a frequency of about 1090 cm$^{-1}$, whereby such presence indicating a state of moderate immunodeficiency and allergy, correlated with Wiskott-Aldrich syndrome.

48. The method as in claim 44, further including a step of examining said region of said infrared absorbance spectra for a presence of a big large rounded peak at a frequency range from about 1080 cm$^{-1}$ to about 1100 cm$^{-1}$, said presence indicating a state of allergy, correlated with bronchial asthma.

49. The method as in claim 44, further including a step of examining said region of said infrared absorbance spectra for a presence of a sharp peak at a frequency of about 1100 cm$^{-1}$, whereby such presence indicating a state of acute cholecystitis.

50. The method as in claim 44, further including a step of examining said region of said infrared absorbance spectra for a presence of a peak with a "long broken and almost horizontal line"-shaped top at a frequency range from about 1030 cm$^{-1}$ to about 1110 cm$^{-1}$, said presence indicating a state of acute viral hepatitis.

51. The method as in claim 2, further including a step of examining a region of said infrared absorbance spectra in a frequency range from about 1100 cm$^{-1}$ to about 1200 cm$^{-1}$, especially the peaks at the frequencies of about 1130 cm$^{-1}$ and 1160 cm$^{-1}$, for a presence of simultaneous deviations from said normal infrared absorbance spectra, said presence indicating a disease state of upper respiratory tract and lungs.

52. The method as in claim 51, further including a step of examining a region of said infrared absorbance spectra for a presence of a sharp simultaneous increase in the infrared absorbance in a frequency range from about 1100 cm$^{-1}$ to about 1200 cm$^{-1}$, especially a peak at a frequency of about 1130 cm$^{-1}$ and a peak at a frequency of about 1160 cm$^{-1}$ (which can occasionally merging into a single large peak), whereby such presence indicating a state of acute pneumonia, if the ratio of the peaks at about 1130 cm$^{-1}$–1160 cm$^{-1}$ to the peak at about 1250 cm$^{-1}$ is about 2.6 or more, or acute viral respiratory infection, if the above peak ratio ranging from about 1.8 to about 2.2. (in norm-0.8).

53. The method as in claim 51, further including a step of examining said region of said infrared absorbance spectra for a presence of a sharp simultaneous reduction in the infrared absorbance in a frequency range from about 1100 cm$^{-1}$ to about 1200 cm$^{-1}$, especially the peaks at the frequencies of about 1130 cm$^{-1}$ and 1160 cm$^{-1}$, said reduction in comparison to said normal infrared absorbance spectra indicating a state of resolving neonatal pneumonia, if the ratio of the peaks at a frequency of about 1130 cm$^{-1}$–1160 cm$^{-1}$ and at a frequency of about 1250 cm$^{-1}$ is about 0.7 or less. (in norm-0.8).

54. The method as in claim 2, further including a step of examining a region of said infrared absorbance spectra in a frequency range from about 1160 cm$^{-1}$ to about 1350 cm$^{-1}$ for a presence of deviations from said normal infrared absorbance spectra, said presence indicating a disease state of a heart.

55. The method as in claim 54, further including a step of examining a region of said infrared absorbance spectra in the area of a peak at a frequency of about 1160 cm$^{-1}$ for a presence of deviations from said normal infrared absorbance spectra, said presence indicating a disease state of a myocardium.

56. The method as in claim 55, further including a step of examining said region of said infrared absorbance spectra for a presence of a pronounced elongated "trapezium"-like peak with a cut top at a frequency of about 1160 cm$^{-1}$, which is higher and narrower than in normal condition, whereby such presence indicating a state of acute myocarditis.

57. The method as in claim 55, further including a step of examining said region of said infrared absorbance spectra for a presence of a widened flattened peak at a frequency range from about 1140 cm$^{-1}$ to about 1160 cm$^{-1}$, with a split widened top at a frequency of about 1150 cm$^{-1}$, which is wider and flatter than in normal condition, whereby such presence indicating a state of cardiomyopathy.

58. The method as in claim 55, further including a step of examining said region of said infrared absorbance spectra for a presence of a peak at a frequency of about 1160 cm$^{-1}$, the lack of said presence indicating a state of myocardial infarction.

59. The method as in claim 54, further including a step of examining a region of said infrared absorbance spectra for a presence of an increase in the infrared absorbance in a frequency range from about 1180 cm$^{-1}$ to about 1200 cm$^{-1}$, said increase in comparison to said normal infrared absorbance spectra indicating a state of heart insufficiency or heart failure.

60. The method as in claim 59, further including a step of examining said region of said infrared absorbance spectra for a presence of a "semi-moon" clipping in a frequency range from about 1180 cm$^{-1}$ to about 1200 cm$^{-1}$, whereby such presence indicating a state of functional murmur.

61. The method as in claim 59, further including a step of examining said region of said infrared absorbance spectra for a presence of a "broken curve" line in a frequency range from about 1180 cm$^{-1}$ to about 1200 cm$^{-1}$, said presence indicating a state of mitral valve prolapse.

62. The method as in claim 59, further including a step of examining said region of said infrared absorbance spectra for a presence of an ascendent "step"-like line with a first step at a frequency range from about 1180 cm$^{-1}$ to about 1189 cm$^{-1}$ and a second high, slanting step at a frequency range from about 1190 cm$^{-1}$ to about 1200 cm$^{-1}$, whereby such presence indicating a state of congenital atrial and ventricular septal defect.

63. The method as in claims 55 or 59, further including a step of examining said region of said infrared absorbance spectra for a presence of a "crown (mitra)"-shaped peak at a frequency of about 1192 cm$^{-1}$ with a wide curve base ranging from about 1180 cm$^{-1}$ to about 1200 cm$^{-1}$ coupled with an elliptical rounded peak at a frequency of about 1150 cm$^{-1}$–1170 cm$^{-1}$, which is smaller than in normal condition, said presence indicating a state of rheumatic mitral regurgitation.

64. The method as in claims 55 or 59, further including a step of examining said region of said infrared absorbance spectra for a presence of a "turned-over equilateral triangle"-like peak at a frequency range from about 1180 cm$^{-1}$ to about 1200 cm$^{-1}$ coupled with a "femur head"-shaped elongated peak at a frequency of about 1150 cm$^{-1}$–1170 cm$^{-1}$, which is longer than in normal condition, whereby such presence indicating a state of aortic stenosis.

65. The method as in claims 55 or 59, further including a step of examining said region of said infrared absorbance spectra for a presence of a "high step"-shaped peak at a frequency range from about 1190 cm$^{-1}$ to about 1200 cm$^{-1}$ coupled with a wide "trapezium"-like peak at a frequency range from about 1160 cm$^{-1}$ to about 1180 cm$^{-1}$, which is smaller than in normal condition, said presence indicating a state of myocardial ischemia.

66. The method as in claim 54, further including a step of examining a region of said infrared absorbance spectra in a frequency range from about 1200 cm$^{-1}$ to about 1350 cm$^{-1}$ for a presence of deviations from said normal infrared absorbance spectra, said presence indicating a disease state of a heart conductive system.

67. The method as in claim 66, further including a step of examining said region of said infrared absorbance spectra for a presence of a peak at a frequency of about 1230 cm$^{-1}$, which is smaller than in normal condition, coupled with three small peaks at the frequencies of about 1270 cm$^{-1}$, 1300 cm$^{-1}$ and 1330 cm$^{-1}$, whereby such presence indicating a state of severe cardiac arrhythmia.

68. The method as in claim 2, further including a step of examining a region of said infrared absorbance spectra in a frequency range from about 1400 cm$^{-1}$ to about 1700 cm$^{-1}$ for a presence of deviations from said normal infrared absorbance spectra, said presence indicating a disease state of brain and central nervous system.

69. The method as in claim 68, further including a step of examining a region of said infrared absorbance spectra for a presence of deviations in a frequency range from about 1400 cm$^{-1}$ to about 1500 cm$^{-1}$, including peaks at the frequencies of about 1410 cm$^{-1}$ and 1460 cm$^{-1}$, said presence indicating a state of less severe functional damages of brain and central nervous system, such as neurosis, minor degree of intracranial hypertension, early stage of convulsion disorders, etc.

70. The method as in claim 68, further including a step of examining a region of said infrared absorbance spectra for a presence of deviations in a frequency range from about 1500 cm$^{-1}$ to about 1700 cm$^{-1}$, including peaks at the frequencies of about 1550 cm$^{-1}$ and 1650 cm$^{-1}$, said presence indicating a state of more severe (organic, anatomic or inflammatory) damages of brain and central nervous system, like head trauma, severe hypoxic ischemic perinatal encephalopathy with intracranial intraventricular hemorrhage, meningitis, cerebrosclerosis, etc.

71. The method as in claim 68, further including a step of examining said region of said infrared absorbance spectra for a sharp increase in the infrared absorbance at a frequency of about 1460 cm$^{-1}$ in such a way that the ratio of the peak at about 1410 cm$^{-1}$ to the peak at about 1460 cm$^{-1}$ becomes less than 1.0 (in norm-1.0) or a presence of an almost horizontal line in a frequency range from about 1450 cm$^{-1}$ to about 1500 cm$^{-1}$ (instead a normally presented peak at a frequency of about 1460 cm$^{-1}$), whereby such presence indicating a state of neurosis.

72. The method as in claim 68, further including a step of examining said region of said infrared absorbance spectra for a sharp decrease in the infrared absorbance at a frequency of about 1460 cm$^{-1}$, whereby such presence indicating a state of epilepsy, if the ratio of the peak at about 1410 cm$^{-1}$ to the peak at about 1460 cm$^{-1}$ is equal 2.0 and more or a state of convulsion disorders, if the above peak ratio is in the range from about 1.7 to about 2.0 (in norm-1.0).

73. The method as in claim 68, further including a step of examining said region of said infrared absorbance spectra for a presence of a large elongated "trapezium"-like peak with a cut top at a frequency of about 1395 cm$^{-1}$ (which is normally smaller and located at a frequency of about 1410 cm$^{-1}$) coupled with an enlarged and widened peak at a frequency of about 1450 cm$^{-1}$ which splits at the right lower side with an appearance of a new little peak at a frequency of about 1470 cm$^{-1}$ (normally there is only one peak at a frequency of about 1460 cm$^{-1}$), whereby such presence indicating a state of severe intracranial hypertension.

74. The method as in claim 68, further including a step of examining said region of said infrared absorbance spectra for only one change, namely a little widening of the right lower side of a peak at a frequency of about 1460 cm$^{-1}$, whereby such presence indicating a state of minor degree of intracranial hypertension in otherwise healthy men.

75. The method as in claim 68, further including a step of examining said region of said infrared absorbance spectra for the presence of:

three large peaks at the frequencies of about 1590 cm$^{-1}$–1610 cm$^{-1}$, 1640 cm$^{-1}$–1650 cm$^{-1}$ and 1660 cm$^{-1}$–1680 cm$^{-1}$ on the top of a big peak at a frequency of about 1650 cm$^{-1}$ (instead a normally presented peak at a frequency of about 1650 cm$^{-1}$), total lack of a peak at a frequency of about 1550 cm$^{-1}$ (instead a normally presented peak at a frequency of about 1550 cm$^{-1}$), the lack of peaks at the frequencies of about 1460 cm$^{-1}$ and 1410 cm$^{-1}$ with transformation into a "saw"-shaped line with a multitude of smaller peaks in a frequency range from about 1380 cm$^{-1}$ to about 1460 cm$^{-1}$ (instead the normally presented peaks at the frequencies of about 1460 cm$^{-1}$ and 1410 cm$^-$), whereby such presence indicating a state of severe hypoxic ischemic perinatal enceplopathy with intracranial intraventricular hemorrhage.

76. The method as in claim 68, further including a step of examining said region of said infrared absorbance spectra for the presence of:

two small peaks of the same elevation at the frequencies of about 1630 cm$^{-1}$ and 1665 cm$^{-1}$ on the top of a big peak at a frequency of about 1650 cm$^{-1}$ (instead a normally presented peak at a frequency of about 1650 cm$^{-1}$), a "terrace"-like descendent line in a frequency range from about 1500 cm$^{-1}$ to about 1600 cm$^{-1}$ (instead a normally presented peak at a frequency of about 1550 cm$^{-1}$), a short and wide "trapezium"-like peak with a cut top at a frequency range from about 1450 cm$^{-1}$ to about 1480 cm$^{-1}$ (instead a normally presented peak at a frequency of about 1460 cm$^{-1}$), a short and wide "trapezium"-shaped peak with a cut top at a frequency range from about 1390 cm$^{-1}$ to about 1410 cm$^{-1}$ (instead a normally presented peak at a frequency of about 1410 cm$^{-1}$), whereby such presence indicating a state of hypoxic ischemic perinatal encephalopathy of a moderate degree.

77. The method as in claim 68, further including a step of examining said region of said infrared absorbance spectra for the presence of:

two small peaks with different elevation: a higher peak at a frequency of about 1670 cm$^{-1}$ and a lower peak at a frequency of about 1645 cm$^{-1}$ on the top of a big peak at a frequency of about 1650 cm$^{-1}$ (instead a normally presented peak at a frequency of about 1650 cm$^{-1}$), a "saw"-like horizontal line with a multitude of smaller peaks in a frequency range from about 1540 cm$^{-1}$ to about 1610 cm$^{-1}$ (instead a normally presented peak at a frequency of about 1550 cm$^{-1}$), a widened and flattened peak at a frequency of about 1460 cm$^{-1}$, which is normally higher and narrower, a slightly widened and flattened peak at a frequency of about 1400 cm$^{-1}$, whereby such presence indicating a state of hypoxic ischemic perinatal encephalopathy of a mild degree.

78. The method as in claim 68, further including a step of examining said region of said infrared absorbance spectra for the presence of:

a small elongated "rectangular"-shaped peak at a frequency range from about 1660 cm$^{-1}$ to about 1670 cm$^{-1}$ and a small flat "tent"-like peak at a frequency of about 1650 cm$^{-1}$ on the top of a big peak at a frequency of about 1650 cm$^{-1}$ (instead a normally presented peak at a frequency of about 1650 cm$^{-1}$), three small peaks at the same elevation at the frequencies of about 1510 cm$^{-1}$, 1530 cm$^{-1}$ and 1550 cm$^{-1}$ on the top of a big peak at a frequency of about 1550 cm$^{-1}$ (instead a normally presented peak at a frequency of about 1650 cm$^{-1}$), an elongated peak at a frequency of about 1450 cm$^{-1}$ which splits on the top into two smaller peaks at frequencies of about 1440 cm$^{-1}$ and 1455 cm$^{-1}$, an elongated peak at a frequency range from about 1390 cm$^{-1}$ to about 1410 cm$^{-1}$ with a little sharp peak on the top at a frequency of about 1390 cm$^{-1}$, whereby such presence indicating a state of brain injury of a minor degree.

79. The method as in claim 68, further including a step of examining said region of said infrared absorbance spectra for the presence of:

two large widened and flattened peaks at the frequencies of about 1620 cm$^{-1}$ and 1640 cm$^{-1}$ on the top of a big peak at a frequency of about 1650 cm$^{-1}$ (instead a normally presented peak at a frequency of about 1650 cm$^{-1}$), a "wave"-like horizontal line in a frequency range from about 1510 cm$^{-1}$ to about 1600 cm$^{-1}$ (instead a normally presented peak at a frequency of about 1550 cm$^{-1}$), a peak at a frequency of about 1430 cm$^{-1}$ (instead a normally presented peak at a frequency of about 1460 cm$^{-1}$), a flattened rounded peak at a frequency of about 1390 cm$^{-1}$ (instead a normally presented peak at a frequency of about 1410 cm$^{-1}$), reduction of the ratio of the peak at about 1390 cm$^{-1}$ to the peak at about 1430 cm$^{-1}$ to about 0.4 (in norm-1.0), whereby such presence indicating a state of postnatal head injury of a moderate degree.

80. The method as in claim 68, further including a step of examining said region of said infrared absorbance spectra for the presence of:

two bulky peaks (on the top of a big peak at a frequency of about 1650 cm$^{-1}$) at the frequencies of about 1640 cm$^{-1}$ and 1660 cm$^{-1}$–1680 cm$^{-1}$, three pronounced peaks of the different elevation (on the top of a big peak at a frequency of about 1550 cm$^{-1}$) at the frequencies of about 1510 cm$^{-1}$, 1530 cm$^{-1}$–1540 cm$^{-1}$ and 1560 cm$^{-1}$, two peaks at the frequencies of about 1450 cm$^{-1}$ and 1470 cm$^{-1}$ (instead a normally presented peak at a frequency of about 1460 cm$^{-1}$), a dramatically enlarged peak at a frequency of about 1390 cm$^{-1}$ (instead a normally presented a peak at a frequency of about 1410 cm$^{-1}$), whereby such presence indicating a state of severe acute bacterial meningitis.

81. The method as in claim 68, further including a step of examining said region of said infrared absorbance spectra for the presence of:

a dramatically enlarged and much sharper than the more rounded in norm peaks at the frequencies of about 1650 cm$^{-1}$, 1550 cm$^{-1}$, 1450 cm$^{-1}$ and 1390 cm$^{-1}$, increase of the ratio of the peak at about 1390 cm$^{-1}$ to the peak at about 1450 cm$^{-1}$ up to about 1.2–1.3 (in norm-1.0), whereby such presence indicating a state of cerebrosclerosis.

82. The method as in claim 68, further including a step of examining said region of said infrared absorbance spectra for the presence of:

a split without divergence on the top of a peak at a frequency of about 1650 cm$^{-1}$ with a transformation into two elongated peaks at frequencies of about 1640 cm$^{-1}$ and 1660 cm$^{-1}$, a similar split without divergence on the top of a peak at a frequency of about 1550 cm$^{-1}$ with a transformation into two elongated peaks at frequencies of about 1540 $cm^{-1}$ and 1560 $cm^{-1}$, a new peak at a frequency of about 1580 $cm^{-1}$, which is absent in norm, a dramatically enlarged peak at a frequency of about 1450 $cm^{-1}$ with a vertical line on the top (instead a normally presented peak at a frequency of about 1460 $cm^{-1}$), a sharp absorbance drop at a frequency of about 1480 $cm^{-1}$, a dramatically elongated peak at a frequency of about 1390 $cm^{-1}$ (instead a normally presented peak at a frequency of about 1410 $cm^{-1}$), whereby such presence indicating a state of rheumatic chorea.

83. The method as in claim 68, further including a step of examining said region of said infrared absorbance spectra for the presence of:

a very elongated "trapezium"-like peak with a hollow cut top at a frequency range from about 1670 $cm^{-1}$ to about 1690 $cm^{-1}$ with a widened base, occupying the range from about 1600 $cm^{-1}$ to about 1740 $cm^{-1}$, a wide "rectangular-trapezium"-like peak with a "wave"-shaped top at a frequency range from about 1500 $cm^{-1}$ to about 1570 $cm^{-1}$ with a small peak on the top at a frequency of about 1545 $cm^{-1}$ and a wide base, occupying the range from about 1480 $cm^{-1}$ to about 1580 $cm^{-1}$, a small peak at a frequency of about 1450 $cm^{-1}$ and a little peak at a frequency of about 1470 $cm^{-1}$ (instead a normally presented peak at a frequency of about 1460 $cm^{-1}$), a flattened and widened peak at a frequency of about 1390 $cm^{-1}$ with a wide base, occupying the range from about 1390 $cm^{-1}$ to about 1400 $cm^{-1}$, a reduction of the ratio of the peak at about 1390 $cm^{-1}$ to the peak at about 1460 $cm^{-1}$ to about 0.4 (in norm-1.0), whereby such presence indicating a state of severe brain damage in a developmentally disabled blind infant with physical and mental retardation in one year after a postnatal head injury.

84. The method as in claim 2, further including a step of examining a region of said infrared absorbance spectra in a frequency range from about 3000 $cm^{-1}$ to about 3100 $cm^{-1}$, especially of a peak at a frequency of about 3060 $cm^{-1}$, for a presence of deviations from said normal infrared absorbance spectra, said presence indicating a state of chronic infection.

85. The method as in claim 84, further including a step of examining said region of said infrared absorbance spectra for a presence of reduction in the infrared absorbance in the range from about 3000 $cm^{-1}$ to about 3100 $cm^{-1}$, especially of a peak at a frequency of about 3060 $cm^{-1}$, in such a way that the ratio of the height for the rising line to that of a subsequently declining line drops to about 2 (in norm-5; for other chronic infections 2.5–4.5), whereby such reduction indicating a state of pulmonary tuberculosis.

* * * * *